United States Patent
Simon et al.

(10) Patent No.: US 11,389,103 B2
(45) Date of Patent: Jul. 19, 2022

(54) DEVICES AND METHODS FOR MONITORING NON-INVASIVE VAGUS NERVE STIMULATION

(71) Applicant: ElectroCore, Inc., Basking Ridge, NJ (US)

(72) Inventors: Bruce J. Simon, Mountain Lakes, NJ (US); Joseph P. Errico, Warren, NJ (US)

(73) Assignee: ELECTROCORE, INC, Basking Rridge, NJ (US)

( * ) Notice: Subject to any disclaimer, the term of this patent is extended or adjusted under 35 U.S.C. 154(b) by 164 days.

(21) Appl. No.: 16/459,391

(22) Filed: Jul. 1, 2019

(65) Prior Publication Data

US 2019/0321633 A1 Oct. 24, 2019

Related U.S. Application Data

(60) Continuation of application No. 15/018,805, filed on Feb. 8, 2016, now Pat. No. 10,335,593, which is a
(Continued)

(51) Int. Cl.
*A61B 5/394* (2021.01)
*A61N 1/36* (2006.01)
(Continued)

(52) U.S. Cl.
CPC ............ *A61B 5/394* (2021.01); *A61B 5/4035* (2013.01); *A61B 5/4041* (2013.01);
(Continued)

(58) Field of Classification Search
CPC ............ A61N 1/36014; A61N 1/36114; A61N 1/0456
(Continued)

(56) References Cited

U.S. PATENT DOCUMENTS

| 3,590,810 A | 7/1971 | Kopecky |
| 4,196,737 A | 4/1980 | Bevilacqua |

(Continued)

FOREIGN PATENT DOCUMENTS

| EP | 1967226 | 9/2008 |
| EP | 1967226 | 10/2008 |

(Continued)

OTHER PUBLICATIONS

Greicius et al., Functional connectivity in the resting brain: A network analysis of the default mode hypothesis, PNAS, Jan. 2003, vol. 100, No. 1, pp. 253-258.

(Continued)

*Primary Examiner* — Amanda K Hulbert
*Assistant Examiner* — Philip C Edwards
(74) *Attorney, Agent, or Firm* — Farber LLC

(57) ABSTRACT

Devices and methods are disclosed that treat a medical condition, such as migraine headache, by electrically stimulating a nerve noninvasively, which may be a vagus nerve situated within a patient's neck. Preferred embodiments allow a patient to self-treat his or her condition. Disclosed methods assure that the device is being positioned correctly on the neck and that the amplitude and other parameters of the stimulation actually stimulate the vagus nerve with a therapeutic waveform. Those methods comprise measuring properties of the patient's larynx, pupil diameters, blood flow within an eye, electrodermal activity and/or heart rate variability.

19 Claims, 10 Drawing Sheets

Related U.S. Application Data division of application No. 13/872,116, filed on Apr. 28, 2013, now Pat. No. 9,254,383, which is a continuation-in-part of application No. 13/858,114, filed on Apr. 8, 2013, now Pat. No. 9,248,286, which is a continuation-in-part of application No. 13/603,799, filed on Sep. 5, 2012, now Pat. No. 8,918,178, which is a continuation-in-part of application No. 13/279,437, filed on Oct. 24, 2011, now Pat. No. 9,174,045, and a continuation-in-part of application No. 13/222,087, filed on Aug. 31, 2011, now Pat. No. 9,174,066, which is a continuation-in-part of application No. 13/183,765, filed on Jul. 15, 2011, now Pat. No. 8,874,227, which is a continuation-in-part of application No. 13/183,721, filed on Jul. 15, 2011, now Pat. No. 8,676,324, which is a continuation of application No. 13/109,250, filed on May 17, 2011, now Pat. No. 8,676,330, which is a continuation-in-part of application No. 13/075,746, filed on Mar. 30, 2011, now Pat. No. 8,874,205, which is a continuation-in-part of application No. 13/005,005, filed on Jan. 12, 2011, now Pat. No. 8,868,177, which is a continuation-in-part of application No. 12/964,050, filed on Dec. 9, 2010, now abandoned, which is a continuation of application No. 12/859,568, filed on Aug. 19, 2010, now Pat. No. 9,037,247, which is a continuation-in-part of application No. 12/612,177, filed on Nov. 4, 2009, now Pat. No. 8,041,428, and a continuation-in-part of application No. 12/408,131, filed on Mar. 20, 2009, now Pat. No. 8,812,112.

(60) Provisional application No. 61/752,895, filed on Jan. 15, 2013, provisional application No. 61/488,208, filed on May 20, 2011, provisional application No. 61/487,439, filed on May 18, 2011, provisional application No. 61/471,405, filed on Apr. 4, 2011, provisional application No. 61/451,259, filed on Mar. 10, 2011, provisional application No. 61/415,469, filed on Nov. 19, 2010.

(51) Int. Cl.
*A61B 5/00* (2006.01)
*A61B 5/024* (2006.01)
*A61B 90/00* (2016.01)
*A61N 1/40* (2006.01)

(52) U.S. Cl.
CPC .......... *A61B 5/4803* (2013.01); *A61B 5/4836* (2013.01); *A61B 5/7264* (2013.01); *A61B 5/7267* (2013.01); *A61N 1/36021* (2013.01); *A61N 1/36031* (2017.08); *A61N 1/36034* (2017.08); *A61B 5/02405* (2013.01); *A61B 5/687* (2013.01); *A61B 2090/3941* (2016.02); *A61N 1/40* (2013.01)

(58) Field of Classification Search
USPC ...................................................... 607/115
See application file for complete search history.

(56) References Cited

U.S. PATENT DOCUMENTS

| | | |
|---|---|---|
| 4,989,605 A | 2/1991 | Rossen |
| 5,109,847 A | 5/1992 | Liss et al. |
| 5,458,141 A | 10/1995 | Neil |
| 5,487,759 A | 1/1996 | Bastyr et al. |
| 5,782,874 A | 7/1998 | Loos |
| 5,899,922 A | 5/1999 | Loos |
| 5,983,131 A | 11/1999 | Weaver et al. |
| 6,341,236 B1 | 1/2002 | Osorio et al. |
| 6,463,327 B1 | 10/2002 | Lurie et al. |
| 6,587,719 B1 | 7/2003 | Barrett et al. |
| 6,610,713 B2 | 8/2003 | Tracey |
| 6,631,297 B1 | 10/2003 | Mo |
| 7,254,444 B2 | 8/2007 | Moore |
| 7,734,340 B2 | 6/2010 | De Ridder |
| 7,797,041 B2 | 9/2010 | Libbus et al. |
| 2002/0099417 A1 | 7/2002 | Naritoku et al. |
| 2002/0183237 A1 | 12/2002 | Puskas |
| 2002/0183804 A1 | 12/2002 | Malaney et al. |
| 2003/0212311 A1 | 11/2003 | Nova et al. |
| 2004/0073271 A1 | 4/2004 | Harry et al. |
| 2004/0243182 A1 | 12/2004 | Cohen et al. |
| 2004/0249416 A1 | 12/2004 | Yun et al. |
| 2005/0021092 A1 | 1/2005 | Yun et al. |
| 2005/0065574 A1 | 3/2005 | Rezai |
| 2005/0113630 A1 | 5/2005 | Fox et al. |
| 2005/0137644 A1 | 6/2005 | Boveja et al. |
| 2005/0165458 A1 | 7/2005 | Boveja |
| 2005/0187590 A1 | 8/2005 | Boveja et al. |
| 2005/0216062 A1 | 9/2005 | Herbst |
| 2005/0267544 A1 | 12/2005 | Lee et al. |
| 2006/0074284 A1 | 4/2006 | Juola et al. |
| 2006/0074450 A1 | 4/2006 | Boveja et al. |
| 2006/0100668 A1 | 5/2006 | Ben-David et al. |
| 2006/0100671 A1 | 5/2006 | Ridder |
| 2006/0173510 A1 | 8/2006 | Besio et al. |
| 2006/0178703 A1 | 8/2006 | Huston et al. |
| 2007/0027496 A1 | 2/2007 | Parnis et al. |
| 2007/0038264 A1 | 2/2007 | Jaax et al. |
| 2007/0106337 A1 | 5/2007 | Errico et al. |
| 2007/0123952 A1 | 5/2007 | Strother et al. |
| 2007/0142886 A1 | 6/2007 | Fischell et al. |
| 2007/0150006 A1* | 6/2007 | Libbus ................ A61N 1/3611 607/2 |
| 2007/0156182 A1 | 7/2007 | Castel et al. |
| 2007/0276449 A1 | 11/2007 | Gunter et al. |
| 2008/0021512 A1 | 1/2008 | Knudson et al. |
| 2008/0027513 A1 | 1/2008 | Carbunaru |
| 2008/0045776 A1 | 2/2008 | Fischell et al. |
| 2008/0077192 A1 | 3/2008 | Harry et al. |
| 2008/0114199 A1 | 5/2008 | Riehl et al. |
| 2008/0132964 A1 | 6/2008 | Cohen et al. |
| 2008/0177190 A1 | 7/2008 | Libbus et al. |
| 2008/0208266 A1* | 8/2008 | Lesser ................ A61N 1/3606 607/2 |
| 2008/0306325 A1 | 12/2008 | Burnett et al. |
| 2009/0036945 A1 | 2/2009 | Chancellor |
| 2009/0099622 A1 | 4/2009 | Fowler |
| 2009/0112283 A1 | 4/2009 | Kriksunov et al. |
| 2009/0132018 A1 | 5/2009 | DiUbaldi et al. |
| 2009/0157149 A1* | 6/2009 | Wahlgren ............ A61N 1/0492 607/66 |
| 2009/0234417 A1 | 9/2009 | Pastena et al. |
| 2009/0234419 A1 | 9/2009 | Maschino et al. |
| 2009/0240297 A1 | 9/2009 | Shavit et al. |
| 2009/0287035 A1 | 11/2009 | Dietrich et al. |
| 2010/0030299 A1 | 2/2010 | Covalin |
| 2010/0152794 A1 | 6/2010 | Radivojevic et al. |
| 2010/0286553 A1 | 11/2010 | Feler et al. |
| 2011/0046432 A1 | 2/2011 | Simon et al. |
| 2011/0152967 A1 | 6/2011 | Simon et al. |
| 2011/0213295 A1 | 9/2011 | Henley et al. |
| 2011/0224749 A1 | 9/2011 | Ben-David et al. |
| 2011/0230701 A1 | 9/2011 | Simon et al. |
| 2012/0029601 A1 | 2/2012 | Simon et al. |
| 2012/0283697 A1 | 11/2012 | Kim et al. |
| 2012/0303080 A1 | 11/2012 | Ben-David et al. |
| 2013/0006322 A1 | 1/2013 | Tai |
| 2013/0060304 A1 | 3/2013 | LaTendresse et al. |
| 2013/0245486 A1 | 9/2013 | Simon et al. |
| 2014/0005743 A1 | 1/2014 | Giuffrida et al. |
| 2014/0172041 A1 | 6/2014 | Draghici |
| 2014/0222102 A1 | 8/2014 | Lemus |
| 2014/0236040 A1 | 8/2014 | Moon |

(56) References Cited

U.S. PATENT DOCUMENTS

2014/0031895 A1 10/2014 Rahimi
2015/0165226 A1 6/2015 Simon et al.
2015/0190637 A1 7/2015 Simon et al.

FOREIGN PATENT DOCUMENTS

| | | |
|---|---|---|
| EP | 2777764 | 8/2015 |
| JP | 2006-515192 | 11/2006 |
| JP | 2009-125263 | 6/2009 |
| JP | 2012-52385 | 9/2013 |
| JP | 2014-510586 | 5/2014 |
| KR | 10-1242190 | 3/2013 |
| KR | 101242190 | 3/2013 |
| WO | WO1993/01862 | 2/1993 |
| WO | WO2005/007120 | 1/2005 |
| WO | WO2007/092062 | 8/2007 |
| WO | WO2008/042902 | 4/2008 |
| WO | WO2007/058780 | 5/2008 |
| WO | WO2009/021080 | 2/2009 |
| WO | WO2009/064641 | 5/2009 |
| WO | WO2009/135693 | 11/2009 |
| WO | WO2012/121750 | 9/2012 |
| WO | WO 2012/174330 | 12/2012 |
| WO | WO2013/066135 | 5/2013 |

OTHER PUBLICATIONS

Heneka et al., Locus ceruleus controls Alzheimer's disease pathology by modulating microglial functions through norepinephrine, PNAS, Mar. 2010, vol. 107, No. 13, pp. 6058-6063.

Lee et al., Clustering of Resting State Networks, PLoS One, Jul. 2012, vol. 7, Issue 7, pp. 1-12.

International Search Report and Written Opinion dated Aug. 25, 2015 in related Application No. PCT/US15/31847 filed May 20, 2015 (10 pages).

International Search Report and Written Opinion dated May 8, 2007 in related PCT Application No. PCT/US2006/042823 filed Nov. 2, 2006 (5 pages).

International Search Report and Written Opinion dated Sep. 17, 2007 in related PCT Application No. PCT/US2006/042828 filed Nov. 2, 2006 (5 pages).

International Search Report and Written Opinion dated Mar. 26, 2008 in related PCT Application No. PCT/US2006/042752 filed Nov. 1, 2006 (7 pages).

International Search Report and Written Opinion dated Dec. 22, 2011 in related PCT Application No. PCT/US2011/049844 filed Aug. 31, 2011 (9 pages).

KR101242190 dated Mar. 25, 2013, Espacenet computer generated English translation (11 pages).

International Search Report and Written Opinion dated Apr. 30, 2013 in related PCT Application No. PCT/US2013/023014 filed Jan. 24, 2013 (7 pages).

International Search Report and Written Opinion dated Dec. 11, 2013 in related PCT Application No. PCT/US2013/058079 filed Sep. 4, 2013 (8 pages).

International Search Report and Written Opinion dated Jan. 29, 2014 in related PCT Application No. PCT/US2013/068804 filed Nov. 6, 2013 (10 pages).

Europe Office Action dated Apr. 24, 2018 in related Application No. 15796247.3 filed May 20, 2015 (6 pages).

Europe Office Action dated Jul. 26, 2018 in related Application No. 11818591.7 filed Aug. 12, 2011 (8 pages).

\* cited by examiner

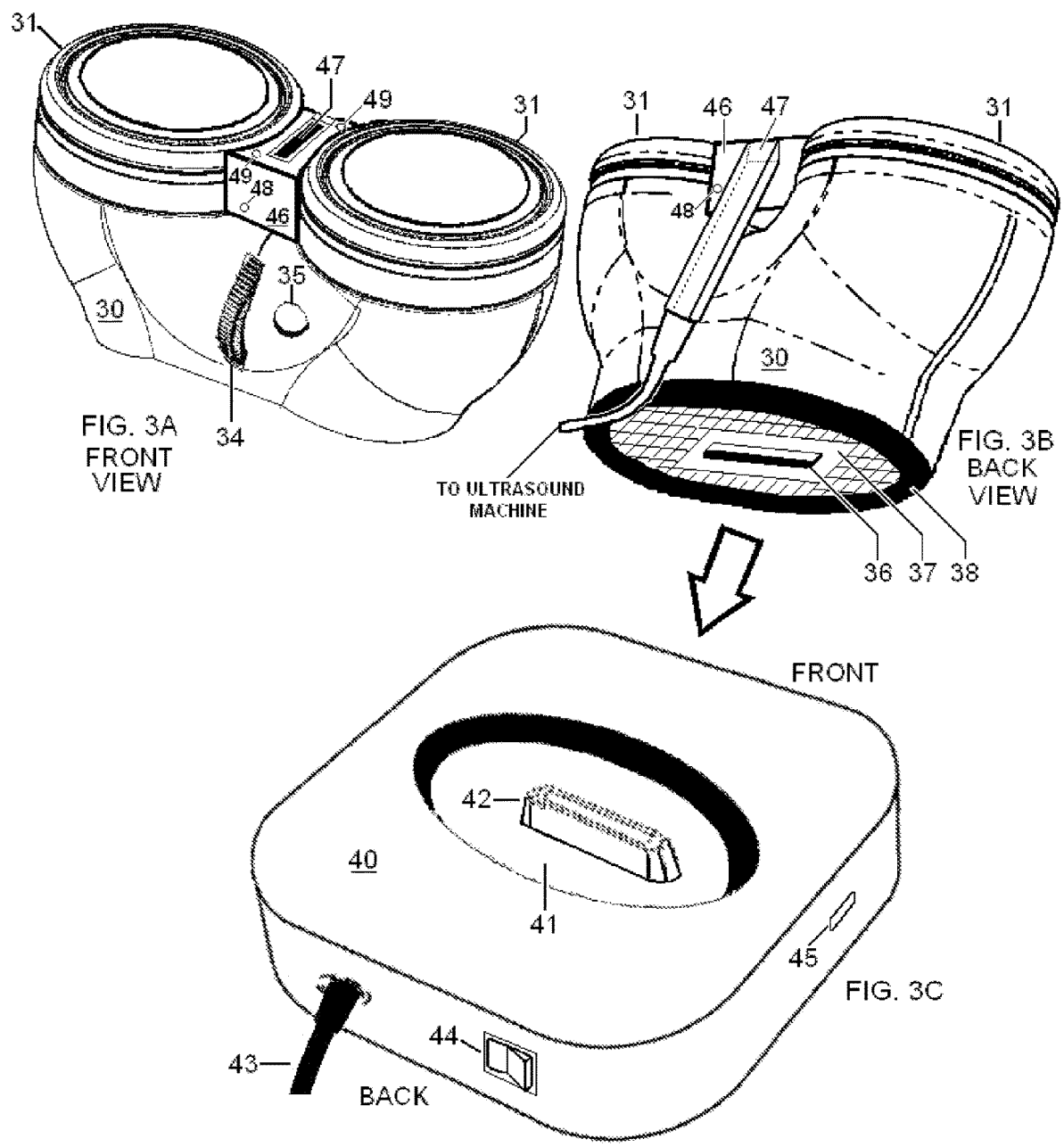

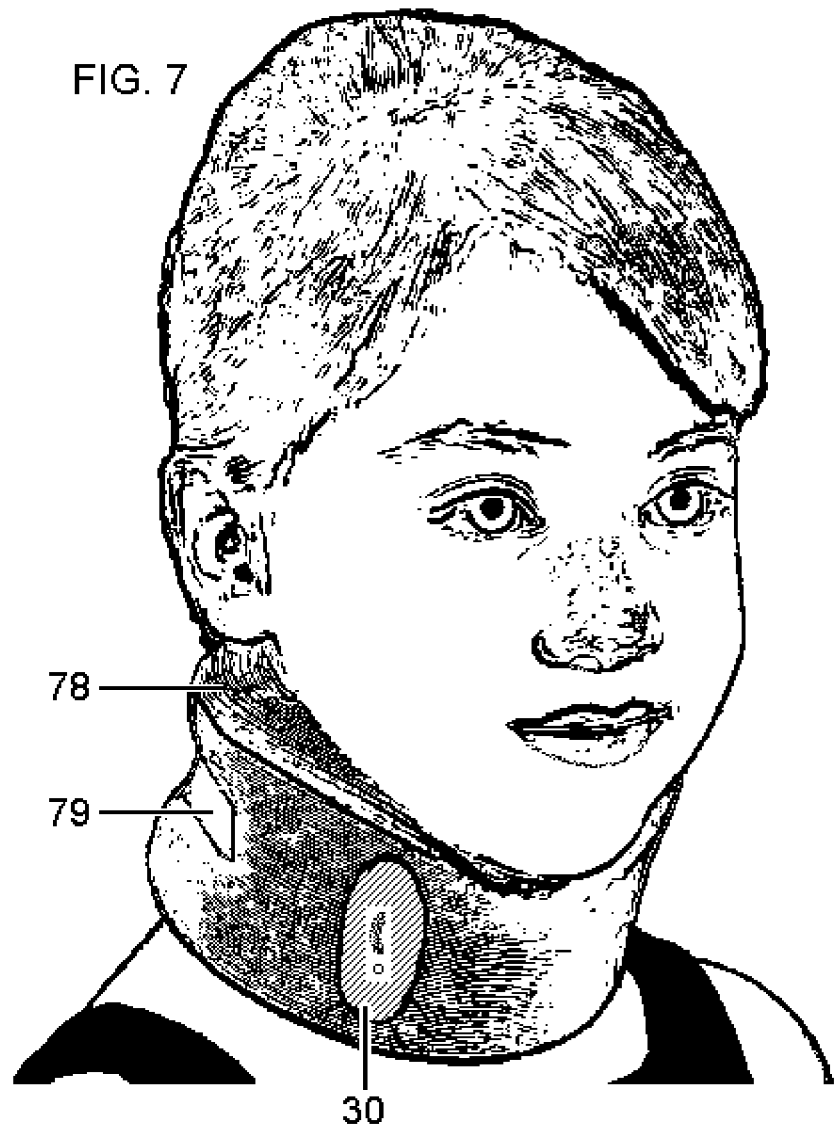

DEVICES AND METHODS FOR MONITORING NON-INVASIVE VAGUS NERVE STIMULATION

CROSS REFERENCE TO RELATED APPLICATIONS

The present application is a continuation of U.S. Nonprovisional application Ser. No. 15/018,805 filed Feb. 8, 2016, which is a divisional of U.S. Nonprovisional application Ser. No. 13/872,116 filed Apr. 28, 2013 now U.S. Pat. No. 9,254,383 issued Feb. 9, 2016, which is a continuation-in-part of U.S. Nonprovisional application Ser. No. 13/858,114 filed Apr. 8, 2013 now U.S. Pat. No. 9,248,286 issued Feb. 2, 2016, which (1) claims the benefit of U.S. Provisional Application Ser. No. 61/752,895 filed Jan. 15, 2013, and (2) is a continuation-in-part of U.S. Nonprovisional application Ser. No. 13/603,799 filed Sep. 5, 2012 now U.S. Pat. No. 8,918,178 issued Dec. 23, 2014, which (a) is a continuation-in-part of U.S. Nonprovisional application Ser. No. 13/279,437 filed Oct. 24, 2011 now U.S. Pat. No. 9,174,045 issued Nov. 3, 2015, and (b) is a continuation-in-part of U.S. Nonprovisional Application Ser. No. 13/222,087 filed Aug. 31, 2011 now U.S. Pat. No. 9,174,066 issued Nov. 3, 2015, which is a continuation-in-part of U.S. Nonprovisional application Ser. No. 13/183,765 filed Jul. 15, 2011 now U.S. Pat. No. 8,874,227 issued Mar. 18, 2014, which (i) claims the benefit of priority of U.S. Provisional Application Ser. No. 61/488,208 filed May 20, 2011, and (ii) is a continuation-in-part of U.S. Nonprovisional application Ser. No. 13/183,721 filed Jul. 15, 2011 now U.S. Pat. No. 8,676,324 issued Mar. 18, 2014, which (A) claims the benefit of priority of U.S. Provisional Application Ser. No. 61/487,439 filed May 18, 2011, and (B) is a continuation-in-part of U.S. Nonprovisional application Ser. No. 13/109,250 filed May 17, 2011 now U.S. Pat. No. 8,676,330, issued Mar. 18, 2014, which (I) claims the benefit of priority of U.S. Provisional Application Ser. No. 61/471,405 filed Apr. 4, 2011, and (II) is a continuation-in-part of U.S. Nonprovisional application Ser. No. 13/075,746 filed Mar. 30, 2011 now U.S. Pat. No. 8,874,205 issued Oct. 28, 2014, which 1) claims the benefit of priority of U.S. Provisional Application 61/451,259 filed Mar. 10, 2011, and 2) is a continuation-in-part of U.S. Nonprovisional application Ser. No. 13/005,005 filed Jan. 12, 2011 now U.S. Pat. No. 8,868,177 issued Oct. 21, 2014, which is a continuation-in-part of U.S. Nonprovisional application Ser. No. 12/964,050 filed Dec. 9, 2010, which a) claims the benefit of priority of U.S. Provisional Application Ser. No. 61/415,469 filed Nov. 19, 2010, and b) is a continuation-in-part of U.S. Nonprovisional Application Ser. No. 12/859,568 filed Aug. 19, 2010 now U.S. Pat. No. 9,037,247 issued May 19, 2015, which i) is a continuation-in-part application of U.S. Nonprovisional Application Ser. No. 12/612,177 filed Nov. 4, 2009 now U.S. Pat. No. 8,041,428 issued Oct. 18, 2011, and ii) is a continuation-in-part of U.S. Nonprovisional application Ser. No. 12/408,131 filed Mar. 20, 2009 now U.S. Pat. No. 8,812,112 issued Aug. 19, 2014; each of which is incorporated herein by reference in its entirety.

BACKGROUND OF THE INVENTION

The field of the present invention relates to the delivery of energy impulses (and/or fields) to bodily tissues for therapeutic purposes, for example, for treating medical conditions such as migraine headaches. The energy impulses (and/or fields) that are used to treat such conditions comprise electrical and/or electromagnetic energy, delivered non-invasively to the patient, particularly to a vagus nerve of the patient. During the course of such treatment, a caregiver and/or the patient uses the disclosed devices and methods to monitor whether the treatment is being applied safely and effectively.

The use of electrical stimulation for treatment of medical conditions is well known. One of the most successful applications of modern understanding of the electrophysiological relationship between muscle and nerves is the cardiac pacemaker. Although origins of the cardiac pacemaker extend back into the 1800's, it was not until 1950 that the first practical, albeit external and bulky, pacemaker was developed. The first truly functional, wearable pacemaker appeared in 1957, and in 1960, the first fully implantable pacemaker was developed.

Around this time, it was also found that electrical leads could be connected to the heart through veins, which eliminated the need to open the chest cavity and attach the lead to the heart wall. In 1975 the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat. No. 6,738,667 to DENO, et al., the disclosure of which is incorporated herein by reference). Because the leads are implanted within the patient, the pacemaker is an example of an implantable medical device.

Another such example is electrical stimulation of the brain with implanted electrodes (deep brain stimulation), which has been approved for use in the treatment of various conditions, including pain and movement disorders such as essential tremor and Parkinson's disease [Joel S. PERLMUTTER and Jonathan W. Mink. Deep brain stimulation. Annu. Rev. Neurosci 29 (2006):229-257].

Another application of electrical stimulation of nerves is the treatment of radiating pain in the lower extremities by stimulating the sacral nerve roots at the bottom of the spinal cord [Paul F. WHITE, shitong Li and Jen W. Chiu. Electroanalgesia: Its Role in Acute and Chronic Pain Management. Anesth Analg 92 (2001):505-513; U.S. Pat. No. 6,871,099, entitled Fully implantable microstimulator for spinal cord stimulation as a therapy for chronic pain, to WHITEHURST, et al].

The form of electrical stimulation that is most relevant to the present invention is vagus nerve stimulation (VNS, also known as vagal nerve stimulation). It was developed initially for the treatment of partial onset epilepsy and was subsequently developed for the treatment of depression and other disorders. The left vagus nerve is ordinarily stimulated at a location within the neck by first surgically implanting an electrode there and then connecting the electrode to an electrical stimulator [U.S. Pat. No. 4,702,254 entitled Neurocybernetic prosthesis, to ZABARA; U.S. Pat. No. 6,341,236 entitled Vagal nerve stimulation techniques for treatment of epileptic seizures, to OSORIO et al; U.S. Pat. No. 5,299,569 entitled Treatment of neuropsychiatric disorders by nerve stimulation, to WERNICKE et al; G. C. ALBERT, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009):1042-1060; GROVES D A, Brown V J. Vagal nerve stimulation: a review of its applications and potential mechanisms that mediate its clinical effects. Neurosci Biobehav Rev 29 (2005):493-500; Reese TERRY, Jr. Vagus nerve stimulation: a proven therapy for treatment of epilepsy strives to improve efficacy and expand applications. Conf Proc IEEE Eng Med Biol Soc. 2009; 2009:4631-4634; Timothy B. MAPSTONE. Vagus nerve stimulation: current concepts. Neurosurg Focus 25 (3, 2008):E9, pp. 1-4; ANDREWS, R. J. Neuromodulation. I. Techniques-deep brain stimulation, vagus nerve stimulation, and transcranial magnetic stimulation. Ann. N.Y. Acad. Sci. 993 (2003):1-13; LABINER, D. M., Ahern, G. L. Vagus nerve stimulation therapy in depression and epilepsy: therapeutic parameter settings. Acta. Neurol. Scand. 115 (2007):23-33; AMAR, A. P., Levy, M. L., Liu, C. Y., Apuzzo, M. L. J. Vagus nerve stimulation. Proceedings of the IEEE 96(7, 2008)1142-1151].

Many such therapeutic applications of electrical stimulation involve the surgical implantation of electrodes within a patient. In contrast, devices used for the procedures that are disclosed here do not involve surgery, i.e., they are not implantable medical devices. Instead, the present devices and methods stimulate nerves by transmitting energy to nerves and tissue non-invasively. A medical procedure is defined as being non-invasive when no break in the skin (or other surface of the body, such as a wound bed) is created through use of the method, and when there is no contact with an internal body cavity beyond a body orifice (e.g., beyond the mouth or beyond the external auditory meatus of the ear). Such non-invasive procedures are distinguished from invasive procedures (including minimally invasive procedures) in that the invasive procedures insert a substance or device into or through the skin (or other surface of the body, such as a wound bed) or into an internal body cavity beyond a body orifice.

For example, transcutaneous electrical stimulation of a nerve is non-invasive because it involves attaching electrodes to the skin, or otherwise stimulating at or beyond the surface of the skin or using a form-fitting conductive garment, without breaking the skin [Thierry KELLER and Andreas Kuhn. Electrodes for transcutaneous (surface) electrical stimulation. Journal of Automatic Control, University of Belgrade 18(2, 2008):35-45; Mark R. PRAUSNITZ. The effects of electric current applied to skin: A review for transdermal drug delivery. Advanced Drug Delivery Reviews 18 (1996) 395-425]. In contrast, percutaneous electrical stimulation of a nerve is minimally invasive because it involves the introduction of an electrode under the skin, via needle-puncture of the skin.

Another form of non-invasive electrical stimulation is magnetic stimulation. It involves the induction, by a time-varying magnetic field, of electrical fields and current within tissue, in accordance with Faraday's law of induction. Magnetic stimulation is non-invasive because the magnetic field is produced by passing a time-varying current through a coil positioned outside the body. An electric field is induced at a distance, causing electric current to flow within electrically conducting bodily tissue. The electrical circuits for magnetic stimulators are generally complex and expensive and use a high current impulse generator that may produce discharge currents of 5,000 amps or more, which is passed through the stimulator coil to produce a magnetic pulse. The principles of electrical nerve stimulation using a magnetic stimulator, along with descriptions of medical applications of magnetic stimulation, are reviewed in: Chris HOVEY and Reza Jalinous, The Guide to Magnetic Stimulation, The Magstim Company Ltd, Spring Gardens, Whitland, Carmarthenshire, SA34 0HR, United Kingdom, 2006. In contrast, the magnetic stimulators that have been disclosed by the present Applicant are relatively simpler devices that use considerably smaller currents within the stimulator coils. Accordingly, they are intended to satisfy the need for simple-to-use and less expensive non-invasive magnetic stimulation devices.

Potential advantages of such non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures are generally painless and may be performed without the dangers and costs of surgery. They are ordinarily performed even without the need for local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace. Furthermore, the cost of non-invasive procedures may be significantly reduced relative to comparable invasive procedures.

In co-pending, commonly assigned patent applications, Applicant disclosed noninvasive electrical and magnetic vagus nerve stimulation devices, which are adapted, and for certain applications improved, in the present disclosure [application Ser. No. 13/183,765 and Publication US2011/0276112, entitled Devices and methods for non-invasive capacitive electrical stimulation and their use for vagus nerve stimulation on the neck of a patient, to SIMON et al.; application Ser. No. 12/964,050 and Publication US2011/0125203, entitled Magnetic Stimulation Devices and Methods of Therapy, to SIMON et al.; and other co-pending commonly assigned applications that are cited herein, which are incorporated by reference]. The present disclosure elaborates on the electrical stimulation device, rather than the magnetic stimulation device that has similar functionality, with the understanding that unless it is otherwise indicated, the elaboration could apply to either the electrical or the magnetic nerve stimulation device.

The non-invasive nerve stimulator may be applied to the patient by a trained healthcare provider or by the patient himself or herself, after having been evaluated and trained in its use by the healthcare provider. The primary advantage of the self-stimulation therapy is that it can be administered more or less immediately when symptoms occur, rather than having to visit the healthcare provider at a clinic or emergency room. The need for such a visit would only compound the aggravation that the patient is already experiencing. Another advantage of the self-stimulation therapy is the convenience of providing the therapy in the patient's home or workplace, which eliminates scheduling difficulties, for example, when the nerve stimulation is being administered for prophylactic reasons at odd hours of the day. Furthermore, the cost of the treatment may be reduced by not requiring the involvement of a trained healthcare provider.

However, a disadvantage of having patients apply the therapy to themselves is that the patient may not always perform the therapy in an optimal fashion, despite having been trained by the caregiver to do so. Furthermore, individual patients may vary in their responsiveness to the therapy, even if it is performed in an optimal fashion. Even the same patient may exhibit day-to-day variations in responsiveness to the therapy. Accordingly, there is need in the art for devices and methods that aid the caregiver and the patient in assuring that the therapy is being administered in an optimal fashion, such that the therapy will be maximally effective and yet have minimum undesirable side-effects. In particular, there is a need for methods to assure that the stimulation is always being performed at an optimal anatomical location on the patient, that the therapy is unambiguously stimulating the target nerve (e.g., vagus nerve), and that the level of stimulation is therapeutically appropriate, as explained in more detail below.

Electrical stimulation by the disclosed methods and devices may be used to treat many medical conditions, including the conditions that are described in the cited co-pending, commonly assigned patent applications. An exemplary teaching of the present invention is the treatment of migraine and other primary headaches such as cluster headaches, including sinus symptoms ("sinus" headaches) irrespective of whether those symptoms arise from an allergy that is co-morbid with the headache. Background information concerning the treatment of migraine headaches by noninvasive vagus nerve stimulation will now be summarized. For more detailed background information on the use of such stimulation to treat migraine/sinus headaches, please refer to co-pending, commonly assigned application number U.S. Ser. No. 13/109,250 with publication number US20110230701, entitled Electrical and magnetic stimulators used to treat migraine/sinus headache and comorbid disorders to SIMON et al; and application number U.S. Ser. No. 13/183,721 with publication number US20110276107, entitled Electrical and magnetic stimulators used to treat migraine/sinus headache, rhinitis, sinusitis, rhinosinusitis, and comorbid disorders, to SIMON et al, which are incorporated by reference.

Chronic daily headache by definition occurs with a frequency of at least 15 headache days per month for greater than 3 months duration. Chronic migraine sufferers comprise a subset of the population of chronic headache sufferers, as do those who suffer other primary headache disorders such as chronic tension-type headache [Bert B. VARGAS, David W. Dodick. The Face of Chronic Migraine: Epidemiology, Demographics, and Treatment Strategies. Neurol Clin 27 (2009) 467-479; Peter J. GOADSBY, Richard B. Lipton, Michel D. Ferrari. Migraine—Current understanding and treatment. N Engl J Med 346 (4, 2002): 257-270; Stephen D SILBERSTEIN. Migraine. LANCET 363 (2004):381-391].

A migraine headache typically passes through the following stages: prodromal, aura, headache pain, and postdromal. All these phases do not necessarily occur, and there is not necessarily a distinct onset or end of each stage, with the possible exception of the aura. An interictal period follows the postdromal, unless the postrome of one migraine attack overlaps the prodrome of the next migraine attack.

The prodrome stage comprises triggering events followed by premonitory symptoms. The prodrome is often characterized by fatigue, sleepiness, elation, food cravings, depression, and irritability, among other symptoms. Triggers (also called precipitating factors) such as excessive stress or sensory barrage usually precede the attack by less than 48 h. The average duration of the prodrome is 6 to 10 hours, but in half of migraine attacks, the prodrome is less than two hours (or absent), and in approximately 15% of migraine attacks, the prodrome lasts for 12 hours to 2 days.

The aura is due to cortical spreading depression within the brain. Approximately 20-30% of migraine sufferers experience an aura, ordinarily a visual aura, which is perceived by the patient as a scintillating scotoma (zig-zag line) that moves within the patient's visual field for typically half an hour. However, aura symptoms, regardless of their form, vary to a great extent in duration and severity from patient to patient, and also within the same individual.

Although the headache phase can begin at any hour, it most commonly begins as mild pain when the patient awakens in the morning. It then gradually builds at variable rates to reach a peak at which the pain is usually described as moderate to severe. Migraine headaches often occur on both sides of the head in children, but an adult pattern of unilateral pain often emerges in adolescence. The pain is often reported as starting in the occipital/neck regions, later becoming frontotemporal. It is throbbing and aggravated by physical effort, with all stimuli tending to accentuate the headache. The pain phase lasts 4-72 h in adults and 1-72 h in children, with a mean duration generally of less than 1 day. The pain intensity usually follows a smooth curve with a crescendo with a diminuendo. After the headache has resolved, many patients are left with a postdrome that lingers for one to two days. The main complaints during the prodrome are cognitive difficulties, such as mental tiredness.

For the present medical applications, an electrical stimulator device is ordinarily applied to the patient's neck. In a preferred embodiment of the invention, the stimulator comprises two electrodes that lie side-by-side within separate stimulator heads, wherein the electrodes are separated by electrically insulating material. Each electrode and the patient's skin are connected electrically through an electrically conducting medium that extends from the skin to the electrode. The level of stimulation power may be adjusted with a wheel or other control feature that also serves as an on/off switch.

The position and angular orientation of the device are adjusted about a location on the neck until the patient perceives stimulation when current is passed through the stimulator electrodes. An objective of the present invention is to assure that the position of the stimulator on the neck is therapeutically optimal. The following related issue also arises. Although the stimulator is designed to be robust against very small variations in position of the stimulator relative to the vagus nerve, fluctuating movement of the stimulator relative to the nerve being stimulated is to some extent unavoidable, due for example to neck muscle contractions that accompany breathing. Such unavoidable movement of the device makes it difficult to assure that the patient is receiving exactly the prescribed stimulation dose in each stimulation session. Accordingly, an objective of the invention is to measure such movement and compensate for it.

The applied current is then increased gradually, first to a level wherein the patient feels sensation from the stimulation. The power is then further increased, but is set to a level that is less than one at which the patient first indicates any discomfort. Another objective of the present invention is to assure that the target nerve (e.g. vagus nerve) is being stimulated, such that the sensation that the patient experiences is not simply due to electrical current passing through the skin and muscle beneath the stimulator heads.

The electrical stimulation is then typically applied for 5 to 30 minutes, which is often sufficient to at least partially relieve headache pain within 5 minutes. The treatment then causes patients to experience a very rapid relief from headache pain, as well as a rapid opening of the nasal passages within approximately 20 minutes. Effects of the treatment may last for 4 to 5 hours or longer. However, for some patients the stimulation is performed for prophylactic purposes, i.e., to prevent a headache from occurring, such that the patient cannot use prompt relief of headache pain as an indication of whether the stimulation was being performed optimally. Furthermore, when the patient is being instructed in the use of the stimulator by a caregiver, such instruction may take place when no headache is in progress. Accordingly, another objective of the present invention is to assure that the stimulation parameters are being set in an optimal fashion during a therapeutic session, without necessarily relying on the prompt relief of symptoms as a guide for whether the parameter selection was appropriate (e.g., selection of stimulation amplitude).

Despite the advantages of having a patient administer the nerve stimulation by himself or herself, such self-stimulation also presents certain risks and difficulties relating to safety. In some situations, the vagus nerve stimulator should be applied to the left or to the right vagus nerve, but not vice versa. In some situations, it would be beneficial to apply the stimulator to both sides of the neck in a prescribed order. On the other hand, in some situations the stimulation may actually be most beneficial if applied to the right vagus nerve, and it may be relatively less effective if applied to the left vagus nerve. Therefore, if the patient is using the vagus nerve stimulator by himself or herself, it would be useful for the device be designed so that it can be used only on the prescribed side of the neck. The present invention discloses several methods for preventing inadvertent stimulation on the side of the neck that is not prescribed.

Another problem is that the patient may wish to stop the stimulation session based only on some subjective assessment of whether the stimulation has sufficiently relieved the symptoms. However, there may be a diminishing effectiveness if the stimulation session is too long, for the following reason. Let the numerical value of the accumulated effects of vagus nerve stimulation be denoted as S(t). It may for present exemplary purposes be represented as a function that increases at a rate proportional to the stimulation voltage V in the vicinity of the nerve and decays with a time constant $\tau_P$, such that after prolonged stimulation, the accumulated stimulation effectiveness may saturate at a value equal to the product of V and $\tau_p$. Thus, if $T_p$ is the duration of a vagus nerve stimulation in a particular treatment session, then for time t<$T_p$, $S(t)=V\tau[1-\exp(-t/\tau_p)]+S_0 \exp(-t/\tau_p)$, and for t>$T_p$, $S(t)=S(T_p)\exp(-[t-T_p]/\tau_p)$, where the time t is measured from the start of a stimulus, and $S_0$ is the value of S when t=0. The optimal duration of a stimulation session may be different from patient to patient, because the decay time constant tip may vary from patient to patient. To the extent that the stimulation protocol is designed to treat each patient individually, such that subsequent treatment sessions are designed in view of the effectiveness of previous treatment sessions, it is would be useful for the stimulation amplitude V be as constant as possible, and the treatment session should take into account the above-mentioned principle of diminishing returns. At a minimum, the average stimulation amplitude in a session should be estimated or evaluated, despite movement of the stimulator relative to the nerve and despite any amplitude adjustment by the patient. The present invention discloses methods and devices for doing so.

SUMMARY OF THE INVENTION

Devices are disclosed that are used to treat a medical condition, such as migraine headache, by electrically stimulating a nerve noninvasively, wherein electrodes are placed against the skin of the patient. In preferred embodiments of the invention, the nerve is a vagus nerve that lies under the skin of the patient's neck. Preferred embodiments of the devices and methods allow a patient to self-treat his or her condition, after having been trained by a caregiver. Methods are disclosed that assure that the device is positioned optimally on the neck and that the amplitude and other stimulation parameters result in therapeutic stimulation of a vagus nerve.

The system comprises a dual-electrode stimulator housing that is applied to the surface of the patient's neck, and it may also include a docking station that is used to charge a rechargeable battery within the stimulator housing. The docking station and stimulator housing also transmit data to one another regarding the status of a stimulation session, prior to and after the session and possibly also during the session. They also transmit data to and from a computer program in a patient interface device, such as a mobile phone or nearby computer. Such data transmission to and from the patient interface device is preferably wireless, but wired communication between devices is also contemplated. The interface device, and possibly the stimulator or docking station, in turn communicates with other computers containing medical record and billing databases, via the internet. Methods are described wherein medical records are used and updated during the course of a stimulation session, and wherein payment for a treatment session is made.

The system is designed to address problems that may arise during self-treatment, when a medical professional is not present. The most significant problem is to assure that the patient is in fact stimulating a vagus nerve. Failure to do so may be because the stimulator is positioned incorrectly on the neck, or because the amplitude or other stimulation parameters are inappropriate. Other potential problems that the invention addresses are that the patient may attempt to stimulate a vagus nerve on the wrong side of the neck (left or right), minimizing or documenting motion of the stimulator, documenting the patient's adjustment of the stimulation amplitude, and controlling the amount of energy that can be delivered to the patient during a stimulation session.

The optimal stimulation position on the neck is initially determined by a caregiver, using ultrasound imaging of the vagus nerve and other criteria. That position is "tattoo"-marked on the patient's skin, using fluorescent dyes that are essentially invisible unless illuminated with ultraviolet or infrared light. When the patient later performs self-stimulation using the device, the device uses internal optical instrumentation to determine that the device is aligned with the "tattoo"-marks.

The parameters for the protocol of each stimulation session are transmitted via the docking station to the stimulator device from a physician-controlled computer, which provides authorization for the charging of the stimulator device's batteries by the docking station. Parameters of the stimulation protocol may be varied in response to heterogeneity in the symptoms of patients. Different stimulation parameters may also be selected as the course of the patient's medical condition changes. In preferred embodiments, the disclosed stimulation methods and devices do not produce clinically significant side effects, such as agitation or anxiety, or changes in heart rate or blood pressure.

In a preferred embodiment of the invention, the stimulator housing comprises a rechargeable source of electrical power and two or more remote electrodes that are configured to stimulate a deep nerve. The stimulator may comprise two electrodes that lie side-by-side within a hand-held housing, wherein the electrodes are separated by electrically insulating material. Each electrode is in continuous contact with an electrically conducting medium that extends from the patient-interface element of the stimulator to the electrode. The interface element contacts the patient's skin when the device is in operation.

Current passing through an electrode may be about 0 to 40 mA, with voltage across the electrodes of about 0 to 30 volts. The current is passed through the electrodes in bursts of pulses. There may be 1 to 20 pulses per burst, preferably five pulses. Each pulse within a burst has a duration of about 20 to 1000 microseconds, preferably 200 microseconds. A burst followed by a silent inter-burst interval repeats at 1 to 5000 bursts per second (bps, similar to Hz), preferably at 15-50 bps, and even more preferably at 25 bps. The preferred shape of each pulse is a full sinusoidal wave.

A source of power supplies a pulse of electric charge to the electrodes, such that the electrodes produce an electric current and/or an electric field within the patient. The electrical stimulator is configured to induce a peak pulse voltage sufficient to produce an electric field in the vicinity of a nerve such as a vagus nerve, to cause the nerve to depolarize and reach a threshold for action potential propagation. By way of example, the threshold electric field for stimulation of the nerve may be about 8 V/m at 1000 Hz. For example, the device may produce an electric field within the patient of about 10 to 600 V/m (preferably less than 100 V/m) and an electrical field gradient of greater than 2 V/m/mm. Electric fields that are produced at the vagus nerve are generally sufficient to excite all myelinated A and B fibers, but not necessarily the unmyelinated C fibers. However, by using a reduced amplitude of stimulation, excitation of A-delta and B fibers may also be avoided.

The preferred stimulator shapes an elongated electric field of effect that can be oriented parallel to a long nerve, such as a vagus. By selecting a suitable waveform to stimulate the nerve, along with suitable parameters such as current, voltage, pulse width, pulses per burst, inter-burst interval, etc., the stimulator produces a correspondingly selective physiological response in an individual patient. Such a suitable waveform and parameters are simultaneously selected to avoid substantially stimulating nerves and tissue other than the target nerve, particularly avoiding the stimulation of nerves in the skin that produce pain.

Demonstration that a vagus nerve is in fact being stimulated is initially undertaken by the caregiver, who marks the optimal stimulation site on the patient's skin with a fluorescent dye. Verification that the vagus nerve is being stimulated is also undertaken later by the patient during self-treatment. Methods used by the caregiver to verify stimulation may make use of ultrasound, radiological imaging, autonomic testing and other equipment that is not available to the patient at home. However, other methods for verifying vagus nerve stimulation, such as analysis of the patient's speech or monitoring the diameter of a pupil of the patient's eye, may be implemented for home use, for example, in a mobile phone app.

The following methods for verifying and monitoring stimulation of the vagus nerve rely on the stimulated vagus nerve causing some physiological response that can be measured, such as some change in the patient's voice (by virtue of stimulation of a recurrent laryngeal nerve, which is a branch of the vagus nerve), autonomic nervous system, evoked potential, chemistry of the blood, or blood flow within the brain.

One method for demonstrating stimulation of a vagus nerve is to measure an increased vagal artery blood flow, preferably using ultrasound contrast agents.

A method involving laryngeal electromography is as follows. Surface electrode arrays are placed symmetrically on both sides of the larynx. Before the vagus nerve is stimulated electrically, but when speech is uttered by the patient, correspondence is made between particular array elements in the left and right arrays, based on the similarity of their signals. Then, as vagus stimulation is applied and its amplitude is increased, the signals from corresponding array elements in the two arrays become increasingly asymmetric during speech or other laryngeal activity, by virtue of the fact that the vagus nerve stimulation preferentially modulates the activity of laryngeal muscles only on one side of the neck.

Acoustic methods for demonstrating vagus nerve stimulation are based on an analysis of the patient's speech, as follows. The patient performs a monotonous pitch raise (continuous glissando), in which he or she phonates a vowel such as /a/ from a low pitch up to a much higher one, spanning multiple voice registers. The speech is transduced by a microphone and is digitized at about 20 to 40 kHz at 16 bits. The resulting time-series is broken into many time segments; and classical and nonlinear acoustic indices are calculated for each of them (e.g., fundamental frequency, jitter, shimmer, relative power in the first five individual harmonic frequencies, Lyapunov exponent).

This set of acoustic data may be supplemented with simultaneously acquired electroglottographic data and/or indices of laryngeal electromyographic asymmetry. Such data with and without vagus nerve stimulation are presented to a support vector machine which, after training, is able to predict from test acoustic data (and/or electroglottographic data and/or electromyographic asymmetry data) whether or not the vagus nerve is being stimulated. One feature that the support vector machine is likely to use in making the classification is as follows. As the patient raises his or her pitch slowly, the larynx shifts from one vocal mode to another at particular frequencies, analogous to an automobile shifting gears. According to the present invention, the frequencies at which those transitions occur may change, depending on the amplitude of vagus nerve stimulation.

The present invention may also make use of autonomic nervous system measurements, which may be used individually or as part of a set of data that is provided to a support vector machine for deciding whether the vagus nerve is being stimulated. The autonomic indices that are preferably measured involve electrodermal activity, heart rate variability, and responses related to the control of pupil diameter and blood flow to the eye, as a function of the amplitude of vagus nerve stimulation.

Additional measurements may be made to assess the existence of effects of vagus nerve stimulation on the autonomic nervous system, comparing data before, during and after the nerve stimulation. They include peripheral blood flow measured with laser Doppler flow meters, simultaneous heart rate and blood pressure variability analysis, valsalva maneuver, deep metronomic breathing, a sustained handgrip test, a cold pressor test, a cold face test, active and passive orthostatic challenge maneuvers, blood pressure response to a mental arithmetic test, pharmacological baroreflex testing, a thermoregulatory sweat test, and a quantitative sudomotor axon reflex test.

Imaging of cerebral blood flow may also be performed to demonstrate the existence of effects of vagus nerve stimulation, comparing the location and magnitude of blood flow before, during and after the nerve stimulation. The imaging may comprise positron emission tomography, functional magnetic resonance imaging (fMRI), and single-photon emission computed tomography (SPECT).

Additional tests for whether the vagus nerve is being stimulated may involve evaluation of electroencephalography (EEG) waveforms and/or the measurement of visual, audio and somatosensory evoked potentials. Changes in absolute vital sign values may also be used to demonstrate that the vagus nerve has been stimulated (absolute heart rate, respiration rate, blood pressure), although if such changes are observed, it might also be concluded that the parameters of the stimulation may best be changed so as not to stimulate vagal C fibers.

Other tests for whether the vagus nerve is being stimulated include changes in pain threshold, changes in balance or sway, and changes in the chemistry of blood or other bodily fluids, as a function of the amplitude of vagus nerve stimulation. The blood chemistry tests involve the measurement of such chemicals as TNF-alpha, other cytokines, serotonin, gastrin, and/or norepinephrine.

Treating a medical condition such as migraine headache may be implemented within the context of control theory. A controller comprising, for example, the disclosed nerve stimulator, a PID, and a feedback or feedforward model, provides input to the patient via stimulation of one or both of the patient's vagus nerves. The signals used to control the stimulation comprise physiological or environmental variables that are measured with sensors. In one embodiment, the vagus nerve stimulation is varied as a function of motion of the stimulator, which is measured using accelerometers.

The novel systems, devices and methods for treating medical condition such as migraine headache are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 3A is a perspective view of a dual-electrode stimulator according to an embodiment of the present invention;

FIG. 3B is a perspective view of the other side of the dual-electrode stimulator shown in FIG. 3A;

FIG. 3C illustrates an exemplary docking station for the dual-electrode stimulator of FIG. 3A;

FIG. 7 illustrates the approximate position of the housing of the stimulator in a neck collar according one embodiment of the present invention, when used to stimulate the right vagus nerve in the neck of a child.

DETAILED DESCRIPTION OF THE PREFERRED EMBODIMENTS

In the present invention, electrodes applied to the skin of the patient generate currents within the tissue of the patient. An objective of the invention is to produce and apply the electrical impulses so as to interact with the signals of one or more nerves, in order to achieve the therapeutic result. Much of the disclosure will be directed specifically to treatment of a patient by electromagnetic stimulation in or around a vagus nerve, with devices positioned non-invasively on or near a patient's neck. However, it will also be appreciated that the devices and methods of the present invention can be applied to other tissues and nerves of the body, including but not limited to other parasympathetic nerves, sympathetic nerves, spinal or cranial nerves.

Description of the Nerve Stimulating/Modulating Devices

Devices of the invention that are used to stimulate a vagus nerve will now be described.

Figure 1:
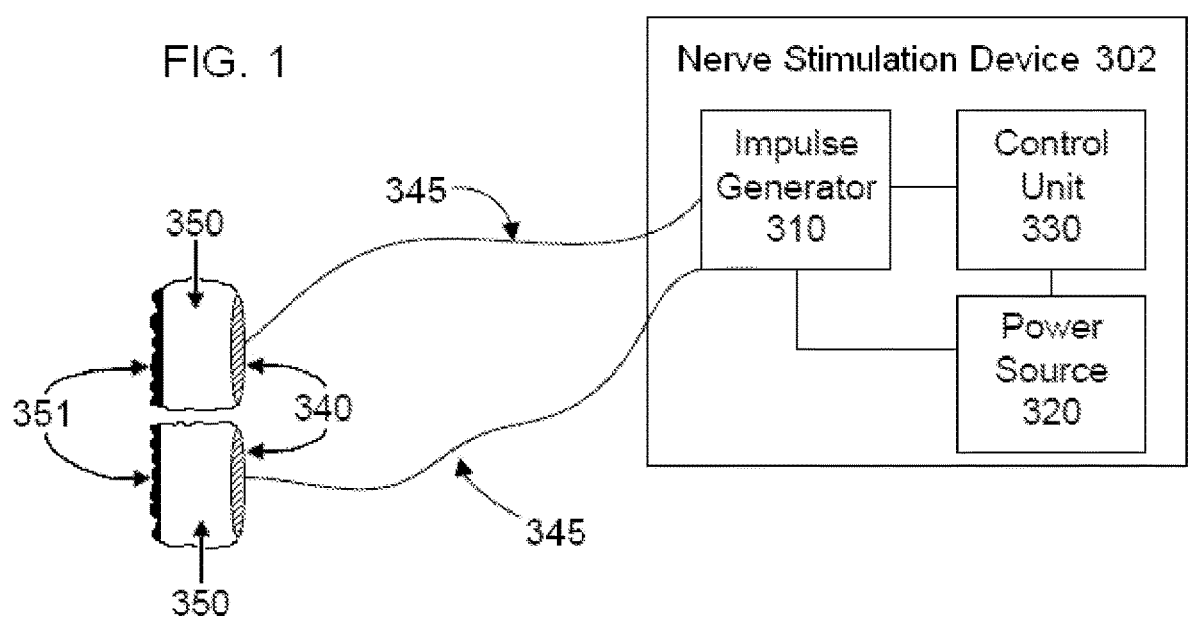
FIG. 1 is a schematic view of nerve modulating devices according to the present invention, which supply controlled pulses of electrical current to surface electrodes.

An embodiment of the present invention is shown in FIG. 1, which is a schematic diagram of an electrode-based nerve stimulating/modulating device 302 for delivering impulses of energy to nerves for the treatment of medical conditions. As shown, device 302 may include an impulse generator 310; a power source 320 coupled to the impulse generator 310; a control unit 330 in communication with the impulse generator 310 and coupled to the power source 320; and electrodes 340 coupled via wires 345 to impulse generator 310. In a preferred embodiment, the same impulse generator 310, power source 320, and control unit 330 may be used for either a magnetic stimulator or the electrode-based stimulator 302, allowing the user to change parameter settings depending on whether magnetic coils or the electrodes 340 are attached. Although a pair of electrodes 340 is shown in FIG. 1, in practice the electrodes may also comprise three or more distinct electrode elements, each of which is connected in series or in parallel to the impulse generator 310. Thus, the electrodes 340 that are shown in FIG. 1 represent all electrodes of the device collectively.

The item labeled in FIG. 1 as 350 is a volume, contiguous with an electrode 340, that is filled with electrically conducting medium. The conducting medium in which the electrode 340 is embedded need not completely surround an electrode. The volume 350 is electrically connected to the patient at a target skin surface in order to shape the current density passed through an electrode 340 that is needed to accomplish stimulation of the patient's nerve or tissue. The electrical connection to the patient's skin surface is through an interface 351. In one embodiment, the interface is made of an electrically insulating (dielectric) material, such as a thin sheet of Mylar. In that case, electrical coupling of the stimulator to the patient is capacitive. In other embodiments, the interface comprises electrically conducting material, such as the electrically conducting medium 350 itself, or an electrically conducting or permeable membrane. In that case, electrical coupling of the stimulator to the patient is ohmic. As shown, the interface may be deformable such that it is form-fitting when applied to the surface of the body. Thus, the sinuousness or curvature shown at the outer surface of the interface 351 corresponds also to sinuousness or curvature on the surface of the body, against which the interface 351 is applied, so as to make the interface and body surface contiguous.

The control unit 330 controls the impulse generator 310 to generate a signal for each of the device's coils or electrodes. The signals are selected to be suitable for amelioration of a particular medical condition, when the signals are applied non-invasively to a target nerve or tissue via the electrodes 340. It is noted that nerve stimulating/modulating device 302 may be referred to by its function as a pulse generator. Patent application publications US2005/0075701 and US2005/0075702, both to SHAFER, contain descriptions of pulse generators that may be applicable to the present invention. By way of example, a pulse generator is also commercially available, such as Agilent 33522A Function/Arbitrary Waveform Generator, Agilent Technologies, Inc., 5301 Stevens Creek Blvd Santa Clara Calif. 95051.

The control unit 330 may also comprise a general purpose computer, comprising one or more CPU, computer memories for the storage of executable computer programs (including the system's operating system) and the storage and retrieval of data, disk storage devices, communication devices (such as serial and USB ports) for accepting external signals from the system's keyboard, computer mouse, and touchscreen, as well as any externally supplied physiological signals (see FIG. 9), analog-to-digital converters for digitizing externally supplied analog signals (see FIG. 9), communication devices for the transmission and receipt of data to and from external devices such as printers and modems that comprise part of the system, hardware for generating the display of information on monitors that comprise part of the system, and busses to interconnect the above-mentioned components. Thus, the user may operate the system by typing instructions for the control unit 330 at a device such as a keyboard and view the results on a device such as the system's computer monitor, or direct the results to a printer, modem, and/or storage disk. Control of the system may be based upon feedback measured from externally supplied physiological or environmental signals. Alternatively, the control unit 330 may have a compact and simple structure, for example, wherein the user may operate the system using only an on/off switch and power control wheel or knob. In a section below, a preferred embodiment is described wherein the stimulator housing has a simple structure, but other components of the control unit 330 are distributed into other devices (see FIG. 5).

Parameters for the nerve or tissue stimulation include power level, frequency and train duration (or pulse number). The stimulation characteristics of each pulse, such as depth of penetration, strength and selectivity, depend on the rise time and peak electrical energy transferred to the electrodes, as well as the spatial distribution of the electric field that is produced by the electrodes. The rise time and peak energy are governed by the electrical characteristics of the stimulator and electrodes, as well as by the anatomy of the region of current flow within the patient. In one embodiment of the invention, pulse parameters are set in such as way as to account for the detailed anatomy surrounding the nerve that is being stimulated [Bartosz SAWICKI, Robert Szmuro, Przemyslaw Ponecki, Jacek Starzy ski, Stanisaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, 105 Press, 2008]. Pulses may be monophasic, biphasic or polyphasic. Embodiments of the invention include those that are fixed frequency, where each pulse in a train has the same inter-stimulus interval, and those that have modulated frequency, where the intervals between each pulse in a train can be varied.

Figure 2A:
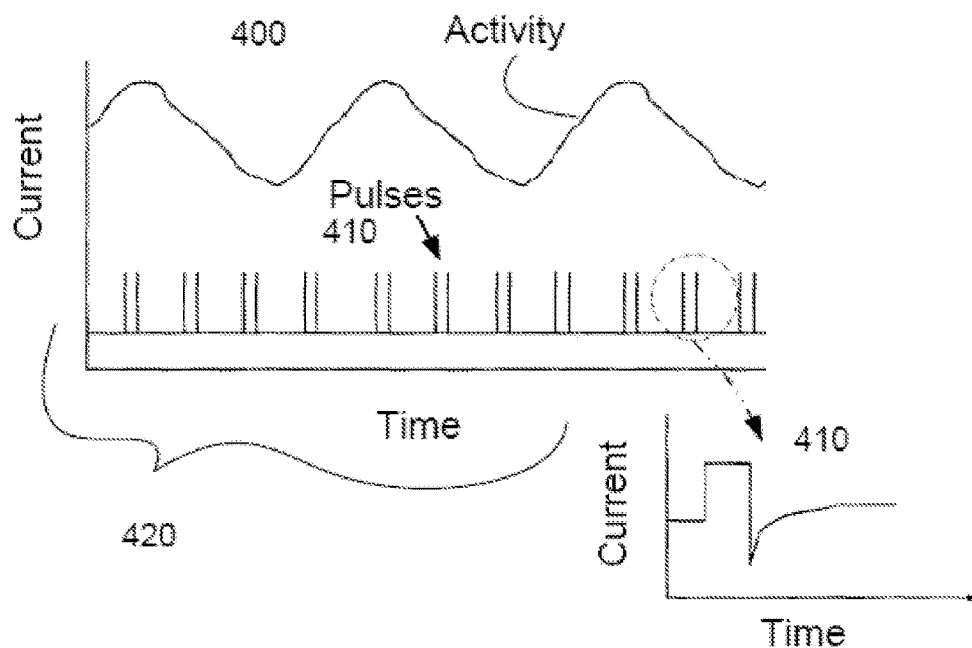
FIG. 2A illustrates an exemplary electrical voltage/current profile for stimulating and/or modulating impulses that are applied to a nerve according to the present invention.

FIG. 2A illustrates an exemplary electrical voltage/current profile for a stimulating, blocking and/or modulating impulse applied to a portion or portions of selected nerves in accordance with an embodiment of the present invention. For the preferred embodiment, the voltage and current refer to those that are non-invasively produced within the patient by the stimulator coils or electrodes. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the electrodes 340 that deliver the stimulating, blocking and/or modulating impulse 410 to the nerve. Nerve stimulating/modulating device 302 may be externally powered and/or recharged or may have its own power source 320. The parameters of the modulation signal 400, such as the frequency, amplitude, duty cycle, pulse width, pulse shape, etc., are preferably programmable. An external communication device may modify the pulse generator programming to improve treatment.

In addition, or as an alternative to the devices to implement the modulation unit for producing the electrical voltage/current profile of the stimulating, blocking and/or modulating impulse to the electrodes, the device disclosed in patent publication No. US2005/0216062 may be employed. That patent publication discloses a multifunctional electrical stimulation (ES) system adapted to yield output signals for effecting electromagnetic or other forms of electrical stimulation for a broad spectrum of different biological and biomedical applications, which produce an electric field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated, as well as the outputs of various sensors which sense prevailing conditions prevailing in this substance, whereby the user of the system can manually adjust the signal, or have it automatically adjusted by feedback, to provide an electrical stimulation signal of whatever type the user wishes, who can then observe the effect of this signal on a substance being treated.

The stimulating and/or modulating impulse signal 410 preferably has a frequency, an amplitude, a duty cycle, a pulse width, a pulse shape, etc. selected to influence the therapeutic result, namely, stimulating and/or modulating some or all of the transmission of the selected nerve. For example, the frequency may be about 1 Hz or greater, such as between about 15 Hz to 100 Hz, more preferably around 25 Hz. The modulation signal may have a pulse width selected to influence the therapeutic result, such as about 1 microseconds to about 1000 microseconds. For example, the electric field induced or produced by the device within tissue in the vicinity of a nerve may be about 5 to 600 V/m, preferably less than 100 V/m, and even more preferably less than 30 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz. The modulation signal may have a peak voltage amplitude selected to influence the therapeutic result, such as about 0.2 volts or greater, such as about 0.2 volts to about 40 volts.

An objective of the disclosed stimulators is to provide both nerve fiber selectivity and spatial selectivity. Spatial selectivity may be achieved in part through the design of the electrode configuration, and nerve fiber selectivity may be achieved in part through the design of the stimulus waveform, but designs for the two types of selectivity are intertwined. This is because, for example, a waveform may selectively stimulate only one of two nerves whether they lie close to one another or not, obviating the need to focus the stimulating signal onto only one of the nerves [GRILL W and Mortimer J T. Stimulus waveforms for selective neural stimulation. IEEE Eng. Med. Biol. 14 (1995): 375-385]. These methods complement others that are used to achieve selective nerve stimulation, such as the use of local anesthetic, application of pressure, inducement of ischemia, cooling, use of ultrasound, graded increases in stimulus intensity, exploiting the absolute refractory period of axons, and the application of stimulus blocks [John E. SWETT and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-295].

To date, the selection of stimulation waveform parameters for nerve stimulation has been highly empirical, in which the parameters are varied about some initially successful set of parameters, in an effort to find an improved set of parameters for each patient. A more efficient approach to selecting stimulation parameters might be to select a stimulation waveform that mimics electrical activity in the anatomical regions that one is attempting stimulate indirectly, in an effort to entrain the naturally occurring electrical waveform, as suggested in patent number U.S. Pat. No. 6,234,953, entitled Electrotherapy device using low frequency magnetic pulses, to THOMAS et al. and application number US20090299435, entitled Systems and methods for enhancing or affecting neural stimulation efficiency and/or efficacy, to GLINER et al. One may also vary stimulation parameters iteratively, in search of an optimal setting [U.S. Pat. No. 7,869,885, entitled Threshold optimization for tissue stimulation therapy, to BEGNAUD et al]. However, some stimulation waveforms, such as those described herein, are discovered by trial and error, and then deliberately improved upon.

Invasive nerve stimulation typically uses square wave pulse signals. However, Applicant found that square waveforms are not ideal for non-invasive stimulation as they may produce excessive pain. Prepulses and similar waveform modifications have been suggested as methods to improve selectivity of nerve stimulation waveforms, but Applicant did not find them ideal [Aleksandra VUCKOVIC, Marco Tosato and Johannes J. Struijk. A comparative study of three techniques for diameter selective fiber activation in the vagal nerve: anodal block, depolarizing prepulses and slowly rising pulses. J. Neural Eng. 5 (2008): 275-286; Aleksandra VUCKOVIC, Nico J. M. Rijkhoff, and Johannes J. Struijk. Different Pulse Shapes to Obtain Small Fiber Selective Activation by Anodal Blocking-A Simulation Study. IEEE Transactions on Biomedical Engineering 51(5, 2004):698-706; Kristian HENNINGS. Selective Electrical Stimulation of Peripheral Nerve Fibers: Accommodation Based Methods. Ph.D. Thesis, Center for Sensory-Motor Interaction, Aalborg University, Aalborg, Denmark, 2004].

Figure 2B:
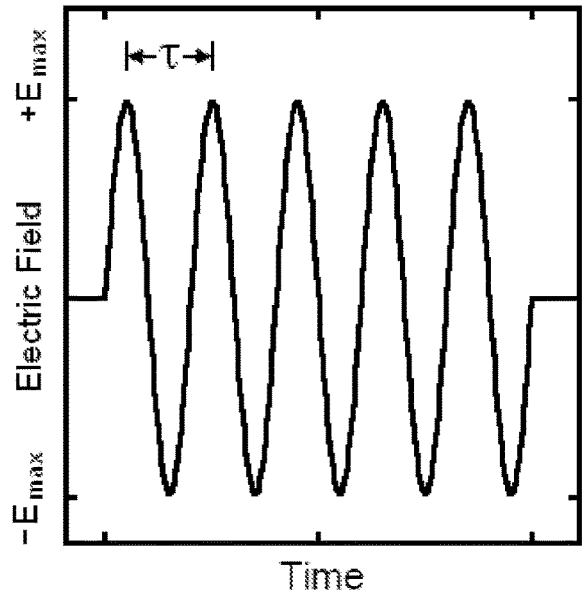
FIG. 2B illustrates an exemplary electrical waveform for stimulating and/or modulating impulses that are applied to a nerve according to the present invention.
Figure 2C:
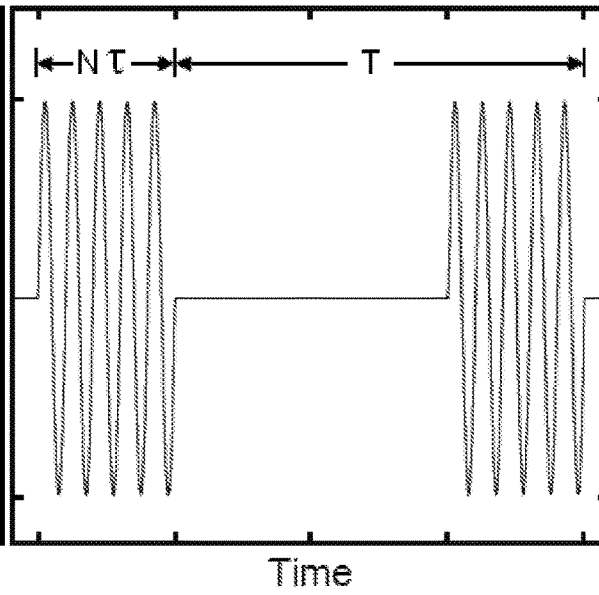
FIG. 2C illustrates a larger portion of the electrical waveform shown in FIG. 2B.

Applicant also found that stimulation waveforms consisting of bursts of square pulses are not ideal for non-invasive stimulation [M. I. JOHNSON, C. H. Ashton, D. R. Bousfield and J. W. Thompson. Analgesic effects of different pulse patterns of transcutaneous electrical nerve stimulation on cold-induced pain in normal subjects. Journal of Psychosomatic Research 35 (2/3, 1991):313-321; U.S. Pat. No. 7,734,340, entitled Stimulation design for neuromodulation, to De Ridder]. However, bursts of sinusoidal pulses are a preferred stimulation waveform, as shown in FIGS. 2B and 2C. As seen there, individual sinusoidal pulses have a period of $\tau$, and a burst consists of N such pulses. This is followed by a period with no signal (the inter-burst period). The pattern of a burst followed by silent inter-burst period repeats itself with a period of T. For example, the sinusoidal period $\tau$ may be 200 microseconds; the number of pulses per burst may be N=5; and the whole pattern of burst followed by silent inter-burst period may have a period of T=40000 microseconds, which is comparable to 25 Hz stimulation (a much smaller value of T is shown in FIG. 2C to make the bursts discernable).

When these exemplary values are used for T and $\tau$, the waveform contains significant Fourier components at higher frequencies (1/200 microseconds=5000/sec), as compared with those contained in transcutaneous nerve stimulation waveforms, as currently practiced.

Applicant is unaware of such a waveform having been used with vagus nerve stimulation, but a similar waveform has been used to stimulate muscle as a means of increasing muscle strength in elite athletes. However, for the muscle strengthening application, the currents used (200 mA) may be very painful and two orders of magnitude larger than what are disclosed herein. Furthermore, the signal used for muscle strengthening may be other than sinusoidal (e.g., triangular), and the parameters $\tau$, N, and T may also be dissimilar from the values exemplified above [A. DELITTO, M. Brown, M. J. Strube, S. J. Rose, and R. C. Lehman. Electrical stimulation of the quadriceps femoris in an elite weight lifter: a single subject experiment. Int J Sports Med 10 (1989):187-191; Alex R WARD, Nataliya Shkuratova. Russian Electrical Stimulation The Early Experiments. Physical Therapy 82 (10, 2002): 1019-1030; Yocheved LAUFER and Michal Elboim. Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88 (10, 2008):1167-1176; Alex R WARD. Electrical Stimulation Using Kilohertz-Frequency Alternating Current. Physical Therapy 89 (2, 2009):181-190; J. PETROFSKY, M. Laymon, M. Prowse, S. Gunda, and J. Batt. The transfer of current through skin and muscle during electrical stimulation with sine, square, Russian and interferential waveforms. Journal of Medical Engineering and Technology 33 (2, 2009): 170-181; U.S. Pat. No. 4,177,819, entitled Muscle stimulating apparatus, to KOFSKY et al]. Burst stimulation has also been disclosed in connection with implantable pulse generators, but wherein the bursting is characteristic of the neuronal firing pattern itself [U.S. Pat. No. 7,734,340 to DE RIDDER, entitled Stimulation design for neuromodulation; application US20110184486 to DE RIDDER, entitled Combination of tonic and burst stimulations to treat neurological disorders]. By way of example, the electric field shown in FIGS. 2B and 2C may have an $E_{max}$ value of 17 V/m, which is sufficient to stimulate the nerve but is significantly lower than the threshold needed to stimulate surrounding muscle.

High frequency electrical stimulation is also known in the treatment of back pain at the spine [Patent application US20120197369, entitled Selective high frequency spinal cord modulation for inhibiting pain with reduced side effects and associated systems and methods, to ALATARIS et al.; Adrian A L KAISY, Iris Smet, and Jean-Pierre Van Buyten. Analgeia of axial low back pain with novel spinal neuromodulation. Poster presentation #202 at the 2011 meeting of The American Academy of Pain Medicine, held in National Harbor, Md., Mar. 24-27, 2011]. Those methods involve high-frequency modulation in the range of from about 1.5 KHz to about 50 KHz, which is applied to the patient's spinal cord region. However, such methods are different from the present invention because, for example, they is invasive; they do not involve a bursting waveform, as in the present invention; they necessarily involve A-delta and C nerve fibers and the pain that those fibers produce, whereas the present invention does not; they may involve a conduction block applied at the dorsal root level, whereas the present invention may stimulate action potentials without blocking of such action potentials; and/or they involve an increased ability of high frequency modulation to penetrate through the cerebral spinal fluid, which is not relevant to the present invention. In fact, a likely explanation for the reduced back pain that is produced by their use of frequencies from 10 to 50 KHz is that the applied electrical stimulus at those frequencies causes permanent damage to the pain-causing nerves, whereas the present invention involves only reversible effects [LEE R C, Zhang D, Hannig J. Biophysical injury mechanisms in electrical shock trauma. Annu Rev Biomed Eng 2 (2000):477-509].

Consider now which nerve fibers may be stimulated by the non-invasive vagus nerve stimulation. The vagus nerve (tenth cranial nerve, paired left and right) is composed of motor and sensory fibers. The vagus nerve leaves the cranium, passes down the neck within the carotid sheath to the root of the neck, then passes to the chest and abdomen, where it contributes to the innervation of the viscera.

A vagus nerve in man consists of over 100,000 nerve fibers (axons), mostly organized into groups. The groups are contained within fascicles of varying sizes, which branch and converge along the nerve. Under normal physiological conditions, each fiber conducts electrical impulses only in one direction, which is defined to be the orthodromic direction, and which is opposite the antidromic direction. However, external electrical stimulation of the nerve may produce action potentials that propagate in orthodromic and antidromic directions. Besides efferent output fibers that convey signals to the various organs in the body from the central nervous system, the vagus nerve conveys sensory (afferent) information about the state of the body's organs back to the central nervous system. Some 80-90% of the nerve fibers in the vagus nerve are afferent (sensory) nerves, communicating the state of the viscera to the central nervous system.

The largest nerve fibers within a left or right vagus nerve are approximately 20 μm in diameter and are heavily myelinated, whereas only the smallest nerve fibers of less than about 1 μm in diameter are completely unmyelinated. When the distal part of a nerve is electrically stimulated, a compound action potential may be recorded by an electrode located more proximally. A compound action potential contains several peaks or waves of activity that represent the summated response of multiple fibers having similar conduction velocities. The waves in a compound action potential represent different types of nerve fibers that are classified into corresponding functional categories, with approximate diameters as follows: A-alpha fibers (afferent or efferent fibers, 12-20 μm diameter), A-beta fibers (afferent or efferent fibers, 5-12 μm), A-gamma fibers (efferent fibers, 3-7 μm), A-delta fibers (afferent fibers, 2-5 μm), B fibers (1-3 μm) and C fibers (unmyelinated, 0.4-1.2 μm). The diameters of group A and group B fibers include the thickness of the myelin sheaths. It is understood that the anatomy of the vagus nerve is developing in newborns and infants, which accounts in part for the maturation of autonomic reflexes. Accordingly, it is also understood that the parameters of vagus nerve stimulation in the present invention are chosen in such a way as to account for this age-related maturation [PEREYRA P M, Zhang W, Schmidt M, Becker L E. Development of myelinated and unmyelinated fibers of human vagus nerve during the first year of life. J Neurol Sci 110(1-2, 1992)107-113].

The waveforms disclosed in FIGS. 2A and 2B contain significant Fourier components at high frequencies (e.g., 1/200 microseconds=5000/sec), even if the waveform also has components at lower frequencies (e.g., 25/sec). Transcutaneously, A-beta, A-delta, and C fibers are typically excited at 2000 Hz, 250 Hz, and 5 Hz, respectively, i.e., the 2000 Hz stimulus is described as being specific for measuring the response of A-beta fibers, the 250 Hz for A-delta fibers, and the 5 Hz for type C fibers [George D. BAQUIS et al. TECHNOLOGY REVIEW: THE NEUROMETER CURRENT PERCEPTION THRESHOLD (CPT). Muscle Nerve 22(Supplement 8, 1999): S247-S259]. Therefore, the high frequency component of the noninvasive stimulation waveform will preferentially stimulate the A-alpha and A-beta fibers, and the C fibers will be largely unstimulated.

However, the threshold for activation of fiber types also depends on the amplitude of the stimulation, and for a given stimulation frequency, the threshold increases as the fiber size decreases. The threshold for generating an action potential in nerve fibers that are impaled with electrodes is traditionally described by Lapicque or Weiss equations, which describe how together the width and amplitude of stimulus pulses determine the threshold, along with parameters that characterize the fiber (the chronaxy and rheobase). For nerve fibers that are stimulated by electric fields that are applied externally to the fiber, as is the case here, characterizing the threshold as a function of pulse amplitude and frequency is more complicated, which ordinarily involves the numerical solution of model differential equations or a case-by-case experimental evaluation [David BOINAGROV, Jim Loudin and Daniel Palanker. Strength-Duration Relationship for Extracellular Neural Stimulation: Numerical and Analytical Models. J Neurophysiol 104 (2010):2236-2248].

For example, REILLY describes a model (the spatially extended nonlinear nodal model or SENN model) that may be used to calculate minimum stimulus thresholds for nerve fibers having different diameters [J. Patrick REILLY. Electrical models for neural excitation studies. Johns Hopkins APL Technical Digest 9(1, 1988): 44-59]. According to REILLY's analysis, the minimum threshold for excitation of myelinated A fibers is 6.2 V/m for a 20 µm diameter fiber, 12.3 V/m for a 10 µm fiber, and 24.6 V/m for a 5 µm diameter fiber, assuming a pulse width that is within the contemplated range of the present invention (1 ms). It is understood that these thresholds may differ slightly from those produced by the waveform of the present invention as illustrated by REILLY's figures, for example, because the present invention prefers to use sinusoidal rather than square pulses. Thresholds for B and C fibers are respectively 2 to 3 and 10 to 100 times greater than those for A fibers [Mark A. CASTORO, Paul B. Yoo, Juan G. Hincapie, Jason J. Hamann, Stephen B. Ruble, Patrick D. Wolf, Warren M. Grill. Excitation properties of the right cervical vagus nerve in adult dogs. Experimental Neurology 227 (2011): 62-68]. If we assume an average A fiber threshold of 15 V/m, then B fibers would have thresholds of 30 to 45 V/m and C fibers would have thresholds of 150 to 1500 V/m. The present invention produces electric fields at the vagus nerve in the range of about 6 to 100 V/m, which is therefore generally sufficient to excite all myelinated A and B fibers, but not the unmyelinated C fibers. In contrast, invasive vagus nerve stimulators that have been used for the treatment of epilepsy have been reported to excite C fibers in some patients [EVANS M S, Verma-Ahuja S, Naritoku D K, Espinosa J A. Intraoperative human vagus nerve compound action potentials. Acta Neurol Scand 110 (2004): 232-238].

It is understood that although devices of the present invention may stimulate A and B nerve fibers, in practice they may also be used so as not to stimulate the largest A fibers (A-delta) and B fibers. In particular, if the stimulator amplitude has been increased to the point at which unwanted side effects begin to occur, the operator of the device may simply reduce the amplitude to avoid those effects. For example, vagal efferent fibers responsible for bronchoconstriction have been observed to have conduction velocities in the range of those of B fibers. In those experiments, bronchoconstriction was only produced when B fibers were activated, and became maximal before C fibers had been recruited [R. M. McALLEN and K. M. Spyer. Two types of vagal preganglionic motoneurones projecting to the heart and lungs. J. Physiol. 282 (1978): 353-364]. Because proper stimulation with the disclosed devices does not result in the side-effect of bronchoconstriction, evidently the bronchoconstrictive B-fibers are possibly not being activated when the amplitude is properly set. Also, the absence of bradycardia or prolongation of PR interval suggests that cardiac efferent B-fibers are not stimulated. Similarly, A-delta afferents may behave physiologically like C fibers. Because stimulation with the disclosed devices does not produce nociceptive effects that would be produced by jugular A-delta fibers or C fibers, evidently the A-delta fibers may not be stimulated when the amplitude is properly set.

Figure 9:
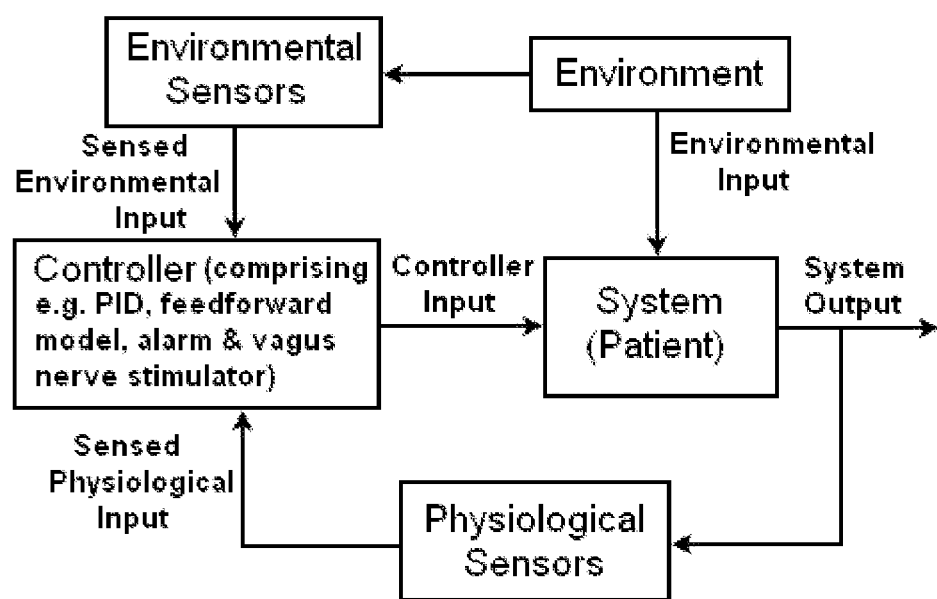
FIG. 9 illustrates connections between the controller and controlled system according to the present invention, their input and output signals, and external signals from the environment.

The use of feedback to generate the modulation signal 400 may result in a signal that is not periodic, particularly if the feedback is produced from sensors that measure naturally occurring, time-varying aperiodic physiological signals from the patient (see FIG. 9). In fact, the absence of significant fluctuation in naturally occurring physiological signals from a patient is ordinarily considered to be an indication that the patient is in ill health. This is because a pathological control system that regulates the patient's physiological variables may have become trapped around only one of two or more possible steady states and is therefore unable to respond normally to external and internal stresses. Accordingly, even if feedback is not used to generate the modulation signal 400, it may be useful to artificially modulate the signal in an aperiodic fashion, in such a way as to simulate fluctuations that would occur naturally in a healthy individual. Thus, the noisy modulation of the stimulation signal may cause a pathological physiological control system to be reset or undergo a non-linear phase transition, through a mechanism known as stochastic resonance [B. SUKI, A. Alencar, M. K. Sujeer, K. R. Lutchen, J. J. Collins, J. S. Andrade, E. P. Ingenito, S. Zapperi, H. E. Stanley, Life-support system benefits from noise, Nature 393 (1998) 127-128; W Alan C MUTCH, M Ruth Graham, Linda G Girling and John F Brewster. Fractal ventilation enhances respiratory sinus arrhythmia. Respiratory Research 2005, 6:41, pp. 1-9].

So, in one embodiment of the present invention, the modulation signal 400, with or without feedback, will stimulate the selected nerve fibers in such a way that one or more of the stimulation parameters (power, frequency, and others mentioned herein) are varied by sampling a statistical distribution having a mean corresponding to a selected, or to a most recent running-averaged value of the parameter, and then setting the value of the parameter to the randomly sampled value. The sampled statistical distributions will comprise Gaussian and 1/f, obtained from recorded naturally occurring random time series or by calculated formula. Parameter values will be so changed periodically, or at time intervals that are themselves selected randomly by sampling another statistical distribution, having a selected mean and coefficient of variation, where the sampled distributions comprise Gaussian and exponential, obtained from recorded naturally occurring random time series or by calculated formula.

In another embodiment, devices in accordance with the present invention are provided in a "pacemaker" type form, in which electrical impulses 410 are generated to a selected region of the nerve by a stimulator device on an intermittent basis, to create in the patient a lower reactivity of the nerve.

Preferred Dual-Electrode Embodiment of the Electrode-Based Stimulator

The electrodes of the invention are applied to the surface of the neck, or to some other surface of the body, and are used to deliver electrical energy non-invasively to a nerve. The vagus nerve has been stimulated previously non-invasively using electrodes applied via leads to the surface of the skin. It has also been stimulated non-electrically through the use of mechanical vibration [HUSTON J M, Gallowitsch-Puerta M, Ochani M, Ochani K, Yuan R, Rosas-Ballina M et al (2007). Transcutaneous vagus nerve stimulation reduces serum high mobility group box 1 levels and improves survival in murine sepsis. Crit Care Med35: 2762-2768; GEORGE M S, Aston-Jones G. Noninvasive techniques for probing neurocircuitry and treating illness: vagus nerve stimulation (VNS), transcranial magnetic stimulation (TMS) and transcranial direct current stimulation (tDCS). Neuropsychopharmacology 35(1, 2010):301-316]. However, no such reported uses of noninvasive vagus nerve stimulation were directed to the treatment of headache sufferers. U.S. Pat. No. 7,340,299, entitled Methods of indirectly stimulating the vagus nerve to achieve controlled asystole, to John D. PUSKAS, discloses the stimulation of the vagus nerve using electrodes placed on the neck of the patient, but that patent is unrelated to the treatment of headache sufferers. Non-invasive electrical stimulation of the vagus nerve has also been described in Japanese patent application JP2009233024A with a filing date of Mar. 26, 2008, entitled Vagus Nerve Stimulation System, to Fukui YOSHIHOTO, in which a body surface electrode is applied to the neck to stimulate the vagus nerve electrically. However, that application pertains to the control of heart rate and is unrelated to the treatment of headache sufferers. In patent publication US20080208266, entitled System and method for treating nausea and vomiting by vagus nerve stimulation, to LESSER et al., electrodes are used to stimulate the vagus nerve in the neck to reduce nausea and vomiting, but this too is unrelated to the treatment of headache sufferers.

Patent application US2010/0057154, entitled Device and method for the transdermal stimulation of a nerve of the human body, to DIETRICH et al., discloses a non-invasive transcutaneous/transdermal method for stimulating the vagus nerve, at an anatomical location where the vagus nerve has paths in the skin of the external auditory canal. Their non-invasive method involves performing electrical stimulation at that location, using surface stimulators that are similar to those used for peripheral nerve and muscle stimulation for treatment of pain (transdermal electrical nerve stimulation), muscle training (electrical muscle stimulation) and electroacupuncture of defined meridian points. The method used in that application is similar to the ones used in U.S. Pat. No. 4,319,584, entitled Electrical pulse acupressure system, to McCALL, for electroacupuncture; U.S. Pat. No. 5,514,175 entitled Auricular electrical stimulator, to KIM et al., for the treatment of pain; and U.S. Pat. No. 4,966,164, entitled Combined sound generating device and electrical acupuncture device and method for using the same, to COLSEN et al., for combined sound/electroacupuncture. A related application is US2006/0122675, entitled Stimulator for auricular branch of vagus nerve, to LIBBUS et al. Similarly, U.S. Pat. No. 7,386,347, entitled Electric stimulator for alpha-wave derivation, to CHUNG et al., described electrical stimulation of the vagus nerve at the ear. Patent application US2008/0288016, entitled Systems and Methods for Stimulating Neural Targets, to AMURTHUR et al., also discloses electrical stimulation of the vagus nerve at the ear. U.S. Pat. No. 4,865,048, entitled Method and apparatus for drug free neurostimulation, to ECKERSON, teaches electrical stimulation of a branch of the vagus nerve behind the ear on the mastoid processes, in order to treat symptoms of drug withdrawal. KRAUS et al described similar methods of stimulation at the ear [KRAUS T, Hosl K, Kiess O, Schanze A, Kornhuber J, Forster C (2007). BOLD fMRI deactivation of limbic and temporal brain structures and mood enhancing effect by transcutaneous vagus nerve stimulation. J Neural Transm 114: 1485-1493]. However, none of the disclosures in these patents or patent applications for electrical stimulation of the vagus nerve at the ear are used to treat headache sufferers.

Embodiments of the present invention may differ with regard to the number of electrodes that are used, the distance between electrodes, and whether disk or ring electrodes are used. In preferred embodiments of the method, one selects the electrode configuration for individual patients, in such a way as to optimally focus electric fields and currents onto the selected nerve, without generating excessive currents on the surface of the skin. This tradeoff between focality and surface currents is described by DATTA et al. [Abhishek DATTA, Maged Elwassif, Fortunato Battaglia and Marom Bikson. Transcranial current stimulation focality using disc and ring electrode configurations: FEM analysis. J. Neural Eng. 5 (2008): 163-174]. Although DATTA et al. are addressing the selection of electrode configuration specifically for transcranial current stimulation, the principles that they describe are applicable to peripheral nerves as well [RATTAY F. Analysis of models for extracellular fiber stimulation. IEEE Trans. Biomed. Eng. 36 (1989): 676-682].

A preferred embodiment of an electrode-based stimulator is shown in FIG. 3. As shown in FIGS. 3A and 3B, the stimulator (30) comprises two heads (31) and a connecting part that joins them. Each head (31) contains a stimulating electrode. The connecting part of the stimulator contains the electronic components and battery (not shown) that are used to generate the signals that drive the electrodes. However, in other embodiments of the invention, the electronic components that generate the signals that are applied to the electrodes may be separate, but connected to the electrode head (31) using wires or wireless communication with the heads. Furthermore, other embodiments of the invention may contain a single such head or more than two heads.

Heads of the stimulator (31) are applied to a surface of the patient's body, during which time the stimulator may be held in place by straps or frames or collars, or the stimulator may be held against the patient's body by hand. In any case, the level of stimulation power may be adjusted with a wheel (34) that also serves as an on/off switch. A light (35) is illuminated when power is being supplied to the stimulator. An optional cap may be provided to cover each of the stimulator heads (31), to protect the device when not in use, to avoid accidental stimulation, and to prevent material within the head from leaking or drying. Thus, in this embodiment of the invention, mechanical and electronic components of the stimulator (impulse generator, control unit, and power source) are compact, portable, and simple to operate.

Details of preferred embodiments of the stimulator heads are described in co-pending, commonly assigned applications that were cited above. As described in those applications, the stimulator designs situate the electrodes of the stimulator (340 in FIG. 1) remotely from the surface of the skin within a chamber, with conducting material (350 in FIG. 1) placed in a chamber between the electrode and the exterior component of the stimulator head that contacts the skin (351 in FIG. 1). One of the novelties of this design is that the stimulator, along with a correspondingly suitable stimulation waveform (see FIGS. 2A and 2B), shapes the electric field, producing a selective physiological response by stimulating that nerve, but avoiding substantial stimulation of nerves and tissue other than the target nerve, particularly avoiding the stimulation of nerves that produce pain. The term "shape an electric field" as used herein means to create an electric field or its gradient that is generally not radially symmetric at a given depth of stimulation in the patient, especially a field that is characterized as being elongated or finger-like, and especially also a field in which the magnitude of the field in some direction may exhibit more than one spatial maximum (i.e. may be bimodal or multimodal) such that the tissue between the maxima may contain an area across which current flow is restricted. Shaping of the electric field refers both to the circumscribing of regions within which there is a significant electric field and to configuring the directions of the electric field within those regions. Our invention does so by configuring elements that are present within equations that were disclosed in the commonly assigned co-pending application US20110230938 (application Ser. No. 13/075,746), entitled Device and methods for non-invasive electrical stimulation and their use for vagal nerve stimulation, to SIMON et al, which is hereby incorporated by reference.

FIG. 3A and FIG. 3B also shows a centerpiece 46 between the stimulator heads 31, the outer surfaces of which all lie in a single plane, along which the stimulator contacts the skin of the patient. Two versions of the centerpiece 46 are used. The version shown in FIGS. 3A and 3B contains an ultrasound transducer/probe 47 for imaging the patient's vagus nerve (or other target structure). The transducer/probe shown there is a "hockey stick" style of probe, so-called because of its shape, which is commercially available from most ultrasound machine manufacturers. Thus, the ultrasound transducer that contacts the patient lies on the foot of the short end of the probe (its head), which is shown as the dark strip in 47 in FIG. 3A. The longer handle of the probe 47 is show as protruding from the centerpiece 46 in the back view shown in FIG. 3B. The handle in turn connects to the ultrasound machine that displays the anatomical structures that lie under the transducer. The head of the "hockey stick" style transducer/probe inserts securely into a groove within the centerpiece 46, so as to make the linear transducer flat against the patient's skin and so as to lie within the plane of the surface of the center of the electrode heads 31. By way of example, the Hitachi Aloka UST-536 19 mm Hockey Stick style Transducer for superficial viewing has a frequency range of 6-13 MHz, a scan angle of 90 degrees, and a scan width of 19 mm (Hitachi Aloka Medical America, 10 Fairfield Boulevard, Wallingford Conn. 06492).

When a cervical vagus nerve is to be stimulated, the ultrasound transducer/probe 47 in the centerpiece 46 is used to determine the optimum location to place the stimulator on the patient's neck. Once that location has been found, spots are marked on the patient's neck to preserve knowledge of the location, with the aid of "wormhole" ducts that are situated within the centerpiece 46. One such duct is shown having an entrance port 48 on the side of the centerpiece and an exit port 49 that lies above the entrance port, on the top surface of the centerpiece. When the stimulator is in its ideal position, a piece of cotton attached to a flexible wire is dipped into a fluorescent dye solution, which is then inserted into the entrance port and advanced through the duct until it reaches the exit port 49. At that point, the dye solution marks the location of the exit port by staining the skin of the patient. Preferably there are two or more such ducts within the centerpiece 46. One of the exit ports 49 in FIG. 3A has a corresponding entrance port 48 that is shown in FIG. 3B.

Figure 3D:
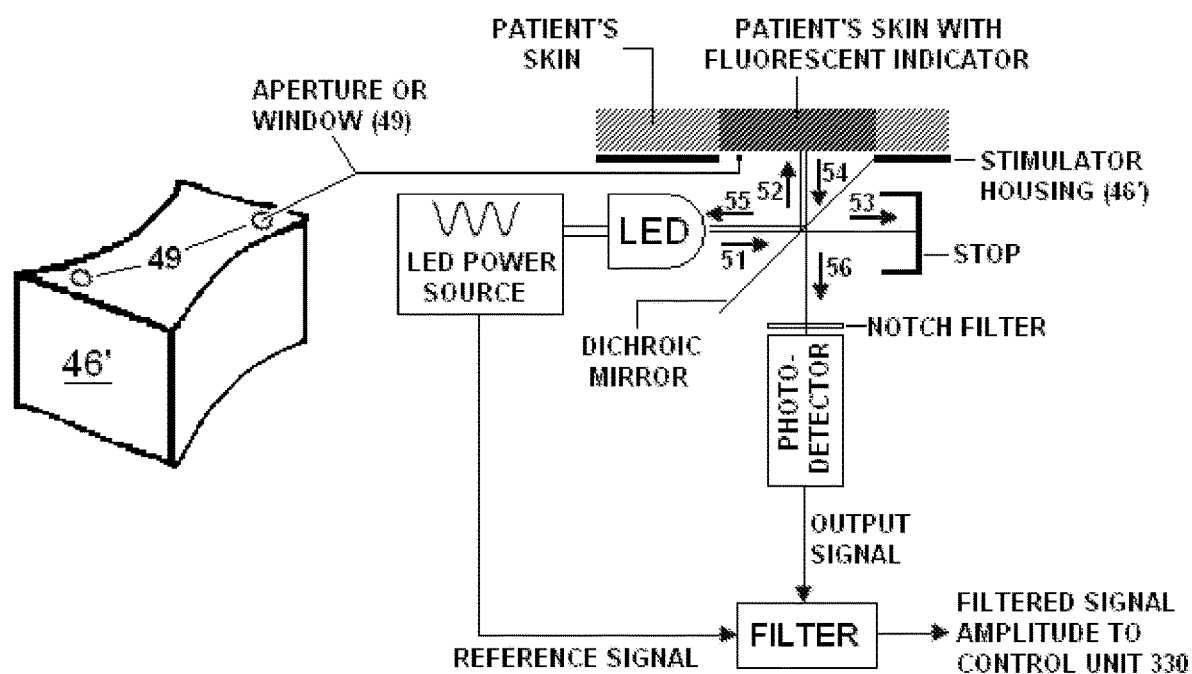
FIG. 3D illustrates a monitoring system for non-invasive vagal nerve stimulation according to the present invention.
Figure 4A:
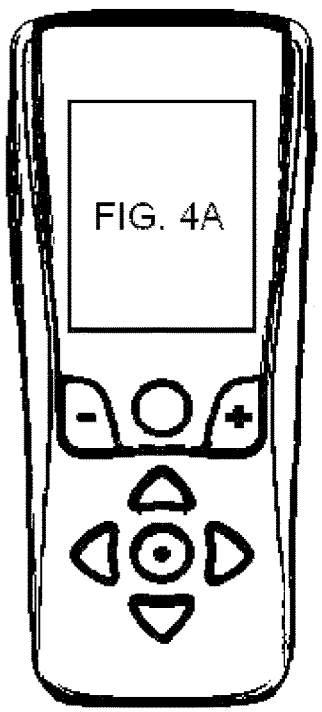
FIG. 4A illustrates a remote control device for communicating with the docking station of FIG. 3C.
Figure 4B:
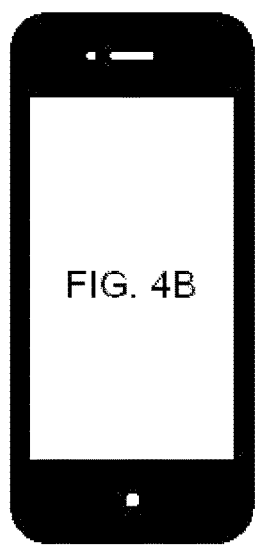
FIG. 4B illustrates a mobile phone for communicating with the docking station of FIG. 3C.
Figure 4C:
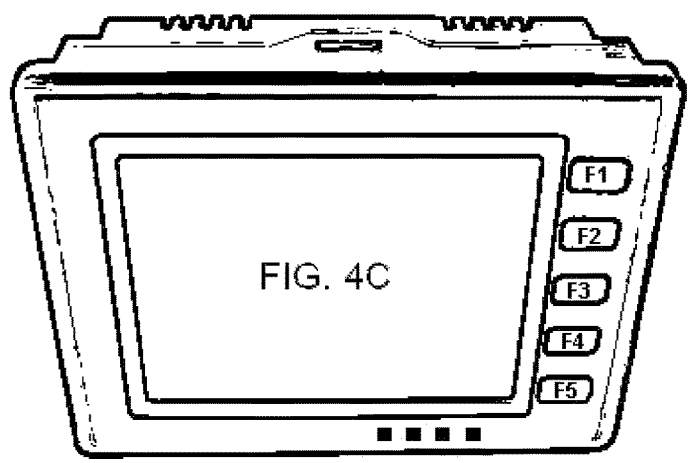
FIG. 4C illustrates a touchscreen device for communicating with the docking station of FIG. 3C.
Figure 4D:
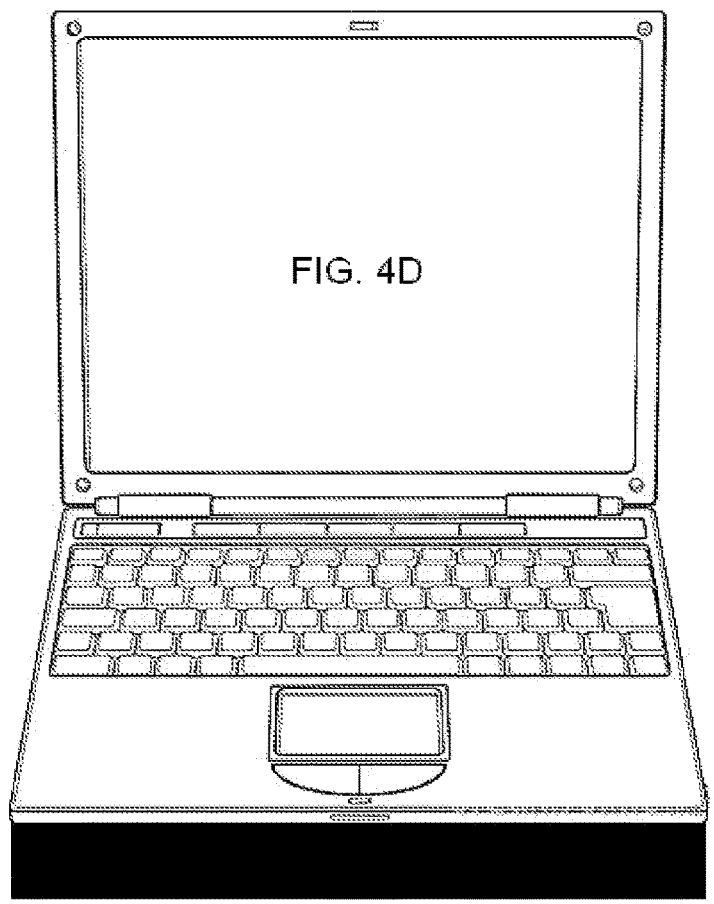
FIG. 4D illustrates a laptop computer for communicating with the docking station of FIG. 3C.

Stimulators containing a second version of the centerpiece 46' are used after the patient's skin has been marked with spots of dye that show the optimal stimulator location. The second centerpiece version is shown in FIG. 3D. As seen there, the centerpiece 46' does not contain an ultrasound transducer/probe. Furthermore, it does not contain any "wormhole" duct as described above in connection with the centerpiece 46. It does, however, contain apertures 49 that have the same positions and registration as the exit ports 49 that were shown in FIG. 3A. The centerpiece 46' also contains optical elements that cause the fluorescent spots on the patient's skin to fluoresce, when the apertures 49 in FIG. 3D align with the spots on the patient's skin (i.e., when the stimulator is in its optimal position). Operation of the optical elements shown in FIG. 3D are described below in connection with a more complete disclosure of methods for applying the stimulator to the patient's neck.

Embodiment of the Vagus Nerve Stimulator with a Docking Station

In some embodiments of the nerve stimulator, all of its components reside in a single hand-held housing. In other embodiments, significant portions of the control of the vagus nerve stimulator may reside in controller components that are physically separate from the housing for the stimulator heads. Thus, some physically separate components of the controller and stimulator housing may generally communicate with one another wirelessly, thereby avoiding the inconvenience and distance limitations of interconnecting cables.

A preferred embodiment of the invention with physically separate components includes a docking station (40 in FIG. 3C) that may be used as a recharging power supply for the stimulator housing (30 in FIG. 3), that may send/receive data to/from the stimulator housing, and that may send/receive data to/from databases and other components of the system, including those that are accessible via the internet. Thus, prior to any particular stimulation session, the docking station may load into the stimulator parameters of the session, including waveform parameters. See FIGS. 2A and 2B and below for criteria used to select the parameters. In a preferred embodiment, the docking station also limits the amount of stimulation energy that may be consumed by the patient in the session by charging the stimulator's rechargable battery with only a specified amount of releasable electrical energy, which is different than setting a parameter to restrict the duration of a stimulation session. As a practical matter, the stimulator housing may therefore use two batteries, one for stimulating the patient (the charge of which may be limited by the docking station) and the other for performing other functions such as data transmission. Methods for evaluating a battery's charge or releasable energy are known in the art, for example, in U.S. Pat. No. 7,751,891, entitled Power supply monitoring for an implantable device, to ARMSTRONG et al. Alternatively, control components within the stimulator housing may monitor the amount of stimulation energy that has been consumed during a stimulation session and stop the stimulation session when a limit has been reached, irrespective of the time when the limit has been reached.

The docking station is shown as item 40 in FIG. 3. The stimulator housing 30 and docking station 40 can be connect to one another by inserting the connector 36 near the center of the base 38 of the stimulator housing 30 into a mated connector 42 of the docking station 40. As shown in FIG. 3, the docking station 30 has an indentation or aperture 41 that allows the base 38 of the stimulator housing 30 to be seated securely into the docking station. The connector 36 of the stimulator housing is recessed in an aperture 37 of the base of the stimulator housing 30 that may be covered by a detachable or hinged cover when the stimulator housing is not attached to the docking station (not shown).

The mated connectors 36 and 42 have a set of contacts that have specific functions for the transfer of power to charge a rechargable battery in the stimulator housing 30 and to transfer data bidirectionally between the stimulator housing and docking station. As a safety feature, the contacts at the two ends of the mated connector are connected to one another within the stimulator housing and within the docking station, such that if physical connection is not made at those end contacts, all the other contacts are disabled via active switches. Also, the connectors 36 and 42 are offset from the center of the base 38 of the stimulator housing 30 and from the center of the indentation or aperture 41 of the docking station 40, so that the stimulator housing can be inserted in only one way into the docking station. That is to say, when the stimulator housing 30 is attached to the docking station 40, the front of the stimulator housing 30 must be on the front side of the docking station 40. As shown, the back side of the docking station has an on/off switch 44 and a power cord 43 that attaches to a wall outlet. The docking station 40 also has ports (e.g., USB ports) for connecting to other devices, one of which 45 is shown on the side of the station, and others of which are located on the front of the station (not shown). The front of the docking station has colored lights to indicatate whether the docking station has not (red) or has (green) charged the stimulator so as to be ready for a stimulation session.

Through cables to the communication port 45, the docking station 40 can communicate with the different types of devices, such as those illustrated in FIG. 4. Handheld devices may resemble conventional remote controls with a display screen (FIG. 4A) or mobile phones (FIG. 4B). Other type of devices with which the docking station may communicate are touchscreen devices (FIG. 4C) and laptop computers (FIG. 4D).

Figure 5:
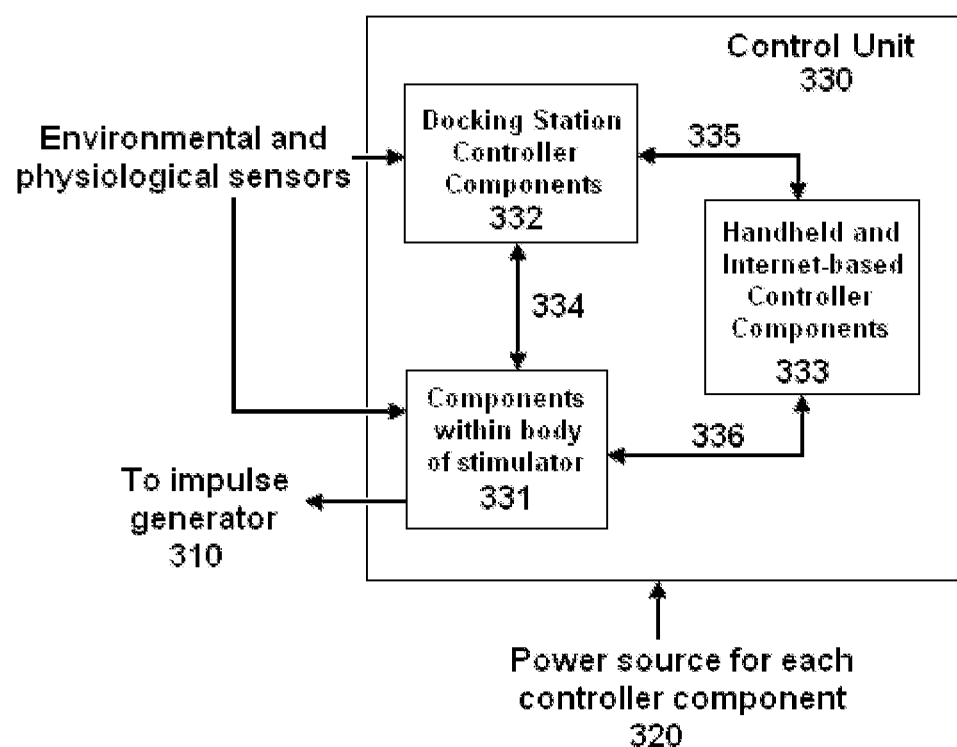
FIG. 5 shows an expanded diagram of the control unit shown in FIG. 1, separating components of the control unit into those within the body of the stimulator, those within the docking station, and those within hand-held and internet-based devices, also showing communication paths between such components.

The communication connections between different components of the stimulator's controller are shown in FIG. 5, which is an expanded representation of the control unit 330 in FIG. 1. Connection between the docking station controller components 332 and components within the stimulator housing 331 is denoted in FIG. 5 as 334. For example, that connection is made when the stimulator housing is connected to the docking station as described above. Connection between the docking station controller components 332 and devices 333 such as those shown in FIG. 4 (generally internet-based components) is denoted as 335. Connection between the components within the stimulator housing 331 and devices 333 such as those shown in FIG. 4 (generally internet-based components) is denoted as 336. Different embodiments of the invention may lack one or more of the connections. For example, if the connection between the stimulator housing and the devices 333 is only through the docking station controller components, then in that embodiment of the invention, only connections 334 and 335 would be present.

The connections 334, 335 and 336 in FIG. 5 may be wired or wireless. For example, if the controller component 333 is the mobile phone shown in FIG. 4B, the connection 335 to a docking station port (45 in FIG. 3) could be made with a cable to the phone's own docking port. Similarly, if the controller component 333 is the laptop computer shown in FIG. 4D, the connection 335 to a docking station port (45 in FIG. 3) could be made with a cable to a USB port on the computer. However, the preferred connections 334, 335, and 336 will be wireless.

Although infrared or ultrasound wireless control might be used to communicate between components of the controller, they are not preferred because of line-of-sight limitations. Instead, in the present disclosure, the communication between devices preferably makes use of radio communication within unlicensed ISM frequency bands (260-470 MHz, 902-928 MHz, 2.400-2.4835 GHz). Components of the radio frequency system in devices in 331, 332, and 333 typically comprise a system-on-chip transciever with an integrated microcontroller; a crystal; associated balun & matching circuitry, and an antenna [Dag GRINI. RF Basics, RF for Non-RF Engineers. Texas Instruments, Post Office Box 655303, Dallas, Tex. 75265, 2006].

Transceivers based on 2.4 GHz offer high data rates (greater than 1 Mbps) and a smaller antenna than those operating at lower frequencies, which makes them suitable for with short-range devices. Furthermore, a 2.4 GHz wireless standard (Bluetooth, Wi-Fi, and ZigBee) may be used as the protocol for transmission between devices. Although the ZigBee wireless standard operates at 2.4 GHz in most jurisdictions worldwide, it also operates in the ISM frequencies 868 MHz in Europe, and 915 MHz in the USA and Australia. Data transmission rates vary from 20 to 250 kilobits/second with that standard. Because many commercially available health-related sensors may operate using ZigBee, its use may be recommended for applications in which the controller uses feedback and feedforward methods to adjust the patient's vagus nerve stimulation based on the sensors' values, as described below in connection with FIG. 9 [ZigBee Wireless Sensor Applications for Health, Wellness and Fitness. ZigBee Alliance 2400 Camino Ramon Suite 375 San Ramon, Calif. 94583].

A 2.4 GHz radio has higher power consumption than radios operating at lower frequencies, due to reduced circuit efficiencies. Furthermore, the 2.4 GHz spectrum is crowded and subject to significant interference from microwave ovens, cordless phones, 802.11b/g wireless local area networks, Bluetooth devices, etc. Sub-GHz radios enable lower power consumption and can operate for years on a single battery. These factors, combined with lower system cost, make sub-GHz transceivers ideal for low data rate applications that need maximum range and multi-year operating life.

The antenna length needed for operating at different frequencies is 17.3 cm at 433 MHz, 8.2 cm at 915 MHz, and 3 cm at 2.4 GHz. Therefore, unless the antenna is included in a neck collar that supports the device shown in FIG. 3A, the antenna length may be a disadvantage for 433 MHz transmission. The 2.4 GHz band has the advantage of enabling one device to serve in all major markets worldwide since the 2.4 GHz band is a global spectrum. However, 433 MHz is a viable alternative to 2.4 GHz for most of the world, and designs based on 868 and 915 MHz radios can serve the US and European markets with a single product.

Range is determined by the sensitivity of the transceiver and its output power. A primary factor affecting radio sensitivity is the data rate. Higher data rates reduce sensitivity, leading to a need for higher output power to achieve sufficient range. For many applications that require only a low data rate, the preferred rate is 40 Kbps where the transceiver can still use a standard off-the-shelf 20 parts per million crystal.

A typical signal waveform that might be transmitted wirelessly to the stimulator housing (30 in FIG. 3) was shown in FIGS. 2B and 2C. As seen there, individual sinusoidal pulses have a period of tau, and a burst consists of N such pulses. This is followed by a period with no signal (the inter-burst period). The pattern of a burst followed by silent inter-burst period repeats itself with a period of T. For example, the sinusoidal period tau may be 200 microseconds; the number of pulses per burst may be N=5; and the whole pattern of burst followed by silent inter-burst period may have a period of T=40000 microseconds, which is comparable to 25 Hz stimulation (a much smaller value of T is shown in FIG. 2C to make the bursts discernable). When these exemplary values are used for T and tau, the waveform contains significant Fourier components at higher frequencies (1/200 microseconds=5000/sec). Such a signal may be easily transmitted using 40 Kbps radio transmission. Compression of the signal is also possible, by transmitting only the signal parameters tau, N, T, $E_{max}$, etc., but in that case the stimulator housing's control electronics would then have to construct the waveform from the transmitted parameters, which would add to the complexity of components of the stimulator housing (30 in FIG. 3).

However, because it is contemplated that sensors attached to the stimulator housing may also be transmitting information, such as accelerometers that are used to detect motion of the stimulator relative to the vagus nerve, the data transfer requirements may be substantially greater than what is required only to transmit the signal shown in FIG. 2A-2C. Electromyographic and electroglottographic data may also need to be transmitted, as described below. Therefore, the present invention may make use of any frequency band, not limited to the ISM frequency bands, as well as techniques known in the art to suppress or avoid noise and interferences in radio transmission, such as frequency hopping and direct sequence spread spectrum.

Application of the Stimulator to the Neck of the Patient

Selected nerve fibers are stimulated in different embodiments of methods that make use of the disclosed electrical stimulation devices, including stimulation of the vagus nerve at a location in the patient's neck. At that location, the vagus nerve is situated within the carotid sheath, near the carotid artery and the interior jugular vein. The carotid sheath is located at the lateral boundary of the retopharyngeal space on each side of the neck and deep to the sternocleidomastoid muscle. The left vagus nerve is sometimes selected for stimulation because stimulation of the right vagus nerve may produce undesired effects on the heart, but depending on the application, the right vagus nerve or both right and left vagus nerves may be stimulated instead.

The three major structures within the carotid sheath are the common carotid artery, the internal jugular vein and the vagus nerve. The carotid artery lies medial to the internal jugular vein, and the vagus nerve is situated posteriorly between the two vessels. Typically, the location of the carotid sheath or interior jugular vein in a patient (and therefore the location of the vagus nerve) will be ascertained in any manner known in the art, e.g., by feel or ultrasound imaging. Proceeding from the skin of the neck above the sternocleidomastoid muscle to the vagus nerve, a line may pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein might be preferred for non-invasive stimulation of the vagus nerve. The magnetic stimulator coil may be centered on such a point, at the level of about the fifth to sixth cervical vertebra.

Figure 6A:
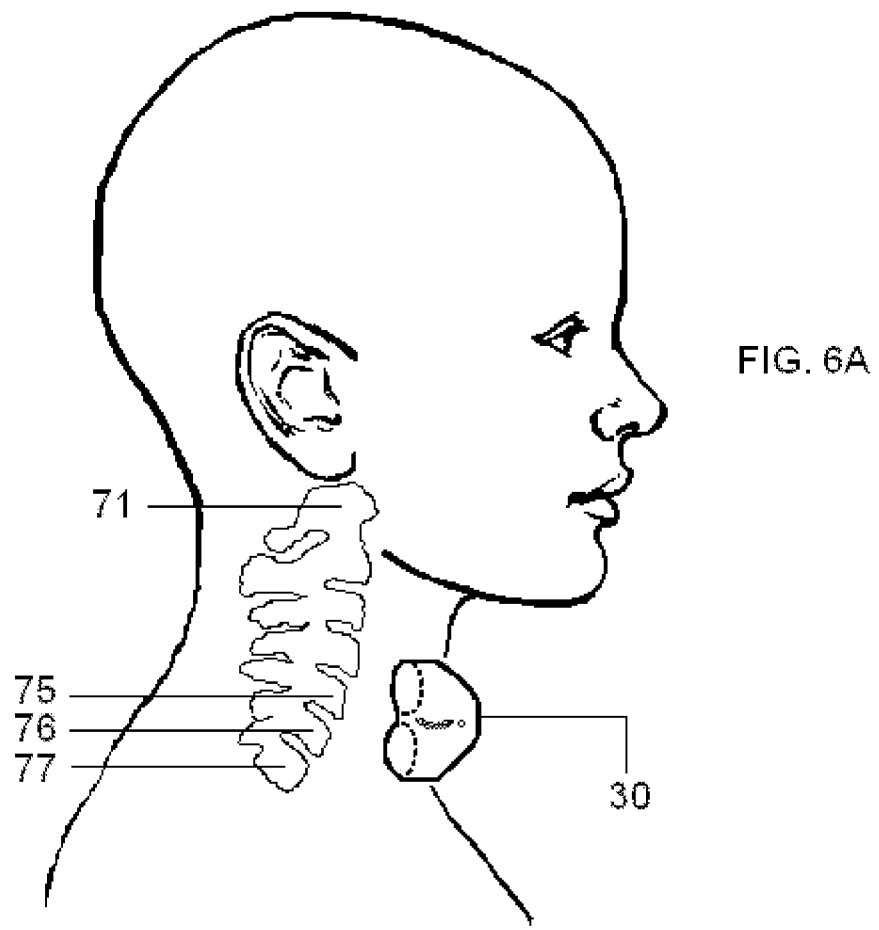
FIG. 6A illustrates the approximate position of the housing of the stimulator according to one embodiment of the present invention when used to stimulate the right vagus nerve in the neck of an adult patient.

FIG. 6A illustrates use of the device 30 shown in FIG. 3 to stimulate the vagus nerve at that location in the neck, in which the stimulator device 30 is shown to be applied to the target location on the patient's neck as described above. For reference, FIG. 6A shows the locations of the following vertebrae: first cervical vertebra 71, the fifth cervical vertebra 75, the sixth cervical vertebra 76, and the seventh cervical vertebra 77.

Figure 6B:
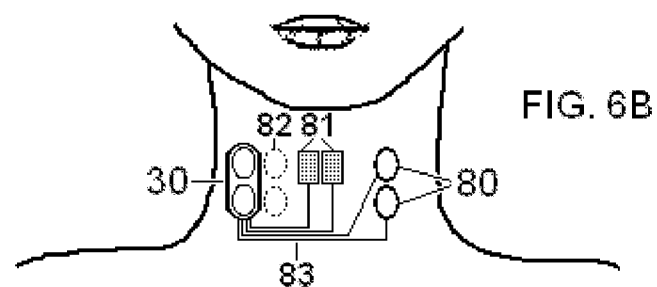
FIG. 6B illustrates the positions of an electrode array according to the present invention for monitoring vagal nerve stimulation via laryngeal electromyography and electroglottography.

FIG. 6B shows the locations of additional electrodes that may be placed on the surface of the neck. The approximate location of a pair of electrodes 80 that may be used for electroglottography is shown, as well as a pair of electrode arrays 81 that may be used for laryngeal electromyography (L-EMG). Use of these additional electrodes is discussed in paragraphs below. Because electroglottography uses electrodes on both sides of the neck, the outer surface of heads of the vagus nerve stimulator 31 may serve as electroglottographic electrodes on the right side of the neck as shown, or separate electrodes 82 may be used for that purpose. Electronics for the electroglottographic and L-EMG methods are housed within the vagus nerve stimulator 30, so lead wires 83 connect the electrodes 80, 81 and 82 (if present) to the stimulator 30. Sinusoidal signals applied to the electroglottograpic electrodes are typically in the range 300 kHz to 5 MHz. This frequency is sufficiently high that the current capacitively bypasses the less conductive skin layer, without the need for using conductive electrode gel or paste. Dry electrodes may also be used for the electromyography [MERLETTI R, Botter A, Troiano A, Merlo E, Minetto M A. Technology and instrumentation for detection and conditioning of the surface electromyographic signal: state of the art. Clin Biomech (Bristol, Avon) 24(2, 2009)122-134].

The additional electrodes and their lead wires may be attached skin-side-up to the inner surface of a collar, so as to help maintain them in their correct position. FIG. 7 shows the stimulator 30 applied to the neck of a child, which is partially immobilized with a foam cervical collar 78 that is similar to ones used for neck injuries and neck pain. The collar is tightened with a strap 79, and the stimulator is inserted through a hole in the collar to reach the child's neck surface. As shown, the stimulator is turned on and off with a control knob, and the amplitude of stimulation may also be adjusted with the control knob that is located on the stimulator. In other models, the control knob is absent or disabled, and the stimulator may be turned on and off remotely, using a wireless controller that may be used to adjust the stimulation parameters of the controller (e.g., on/off, stimulation amplitude, frequency, etc.).

Figure 8:
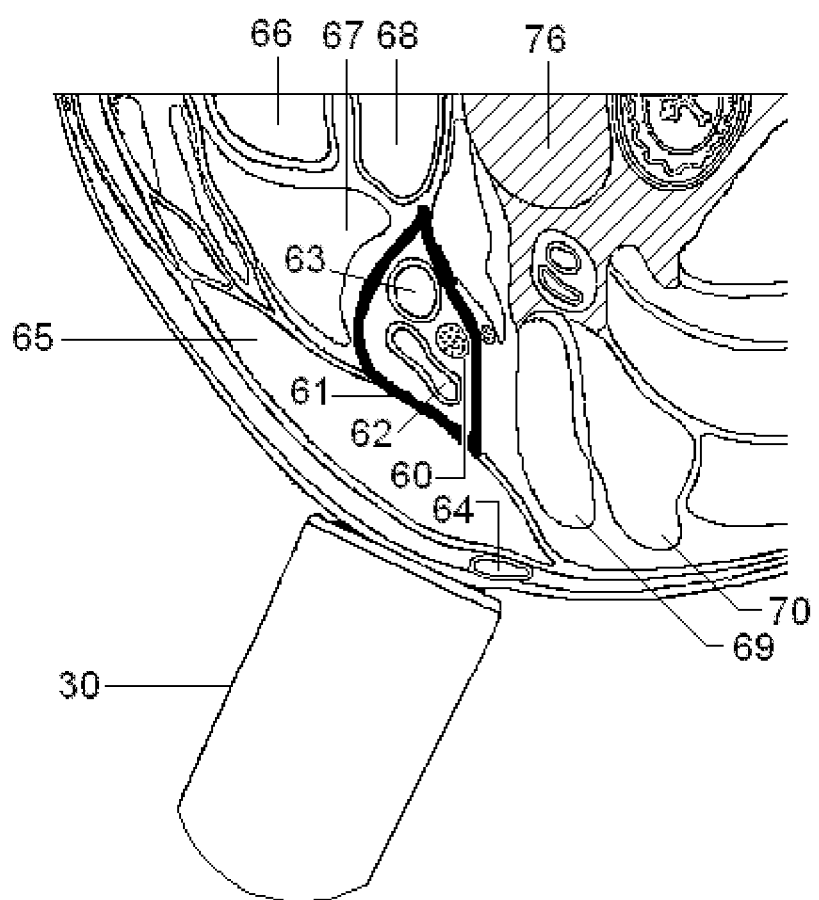
FIG. 8 illustrates the housing of the stimulator according one embodiment of the present invention, when positioned to stimulate a vagus nerve in the patient's neck, wherein the stimulator is applied to the surface of the neck in the vicinity of the identified anatomical structures.

FIG. 8 provides a more detailed view of use of the electrical stimulator 30, when positioned to stimulate the vagus nerve at the neck location that is indicated in FIG. 6. The vagus nerve 60 is identified in FIG. 8, along with the carotid sheath 61 that is identified there in bold peripheral outline. The carotid sheath encloses not only the vagus nerve, but also the internal jugular vein 62 and the common carotid artery 63. Features that may be identified near the surface of the neck include the external jugular vein 64 and the sternocleidomastoid muscle 65. Additional organs in the vicinity of the vagus nerve include the trachea 66, thyroid gland 67, esophagus 68, scalenus anterior muscle 69, and scalenus medius muscle 70. The sixth cervical vertebra 76 is also shown in FIG. 8, with bony structure indicated by hatching marks.

Methods of treating a patient comprise stimulating the vagus nerve as indicated in FIGS. 6 and 7, using the electrical stimulation devices that are disclosed here. Before stimulation is performed, the neck is cleaned but not abraded, and depending on the individual, hair may have been previously removed by conventional epilation methods (e.g., waxing or electrology). Stimulation may be performed on the left or right vagus nerve or on both of them simultaneously or alternately. The location of a vagus nerve underlying the stimulator may be determined preliminarily by imaging with the ultrasound probe 47 in FIGS. 3A and 3B [KNAPPERTZ V A, Tegeler C H, Hardin S J, McKinney W M. Vagus nerve imaging with ultrasound: anatomic and in vivo validation. Otolaryngol Head Neck Surg 118(1, 1998): 82-85; GIOVAGNORIO F and Martinoli C. Sonography of the cervical vagus nerve: normal appearance and abnormal findings. AJR Am J Roentgenol 176(3, 2001):745-749]. On transverse scans, the vagus nerve has a honeycomb appearance with 2 to 4 hypoechoic rounded fascicles surrounded by a hyperechoic epineurium. To the extent that there is variation in the distance between the skin and vagus nerve as a function of position up and down the neck, the stimulator should be positioned in such a way that the distance is minimized.

The stimulator should also be positioned in such a way that the nerve is located in the center of the ultrasound image, taking into account the fact that in approximately 5 percent of individuals, the vagus nerve has an unusual anatomical course that is possibly associated with abnormal thyroid gland anatomy. Also, the vagus nerve of approximately 25% of individuals has an atypical position within the carotid sheath [GIBSON A. Bilateral abnormal relationship of the vagus nerve in its cervical portion. J Anat Physiol 49 (1915):389-392; TUBBS R S, Loukas M, Shoja M M, Blevins D, Humphrey R, Chua G D, Kelly D R, Oakes W J. An unreported variation of the cervical vagus nerve: anatomical and histological observations. Folia Morphol (Warsz) 66(2, 2007):155-157; PARK J K, Jeong S Y, Lee J H, Lim G C, Chang J W. Variations in the course of the cervical vagus nerve on thyroid ultrasonography. AJNR Am J Neuroradiol 32(7, 2011):1178-1181; DIONIGI G, Chiang F Y, Rausei S, Wu C W, Boni L, Lee K W, Rovera F, Cantone G, Bacuzzi A. Surgical anatomy and neurophysiology of the vagus nerve (VN) for standardized intraoperative neuromonitoring (IONM) of the inferior laryngeal nerve (ILN) during thyroidectomy. Langenbecks Arch Surg 395(7, 2010):893-899]. In addition to an unusual anatomical course of the vagus nerve, the ultrasound imaging may also reveal potential problems such as inflammation of the nerve that may contraindicate the use of vagus nerve stimulation [Einar P V WILDER-SMITH. Nerve Ultrasound: Ready for clinical practice? Neurology Asia 17(1, 2012):1-4].

As part of the preliminary protocol, the patient is instructed or helped to perform neck movements, to breathe deeply so as to contract the sternocleidomastoid muscle, and generally to simulate possible motion that may accompany prolonged stimulation with the stimulator. The stimulator is maintained firmly in place against the neck as the movements are made, such that the stimulator will also experience some movement. Straps, harnesses, collars, or frames may be used to maintain the stimulator in position. The movement of the stimulator is monitored using miniature three-axis accelerometers (possibly with combined gyroscopes) that are embedded in the body of the stimulator (for example, Model LSM330DL from STMicroelectronics, 750 Canyon Dr #300 Coppell, Tex. 75019). Such an accelerometer is situated in each of the two simulator heads (31 in FIG. 3), and another accelerometer is situated in the vicinity of the bottom of the stimulator (38 in FIG. 3). While these movements are being performed, the accelerometers are acquiring position information, and the corresponding location of the vagus nerve is determined from the ultrasound image. With these preliminary data, it is then possible to infer the location of the vagus nerve relative to the stimulator, given only the accelerometer data during a stimulation session, by interpolating between the previously acquired vagus nerve position data as a function of accelerometer position data.

Actual nerve stimulation is then performed with a sinusoidal burst waveform like that shown in FIGS. 2A-2C. The pattern of a burst followed by silent inter-burst period repeats itself with a period of T. For example, the sinusoidal period $\tau$ may be 200 microseconds; the number of pulses per burst may be N=5; and the whole pattern of burst followed by silent inter-burst period may have a period of T=40000 microseconds, which is comparable to 25 Hz stimulation. More generally, there may be 1 to 20 pulses per burst, preferably five pulses. Each pulse within a burst has a duration of 1 to 1000 microseconds (i.e., about 1 to 10 KHz), preferably 200 microseconds (about 5 KHz). A burst followed by a silent inter-burst interval repeats at 1 to 5000 bursts per second (bps), preferably at 5-50 bps, and even more preferably 10-25 bps stimulation (10-25 Hz). The preferred shape of each pulse is a full sinusoidal wave, although triangular or other shapes may be used as well.

The amplitude of the stimulation is initially increased until the patient first perceives stimulation when current is passed through the stimulator electrodes. The applied current is increased gradually, to a level wherein the patient feels constant sensation from the stimulation. The power may then be increased even more, but is set to a level that is less than one at which the patient first indicates any discomfort. The stimulator signal may have a frequency and other parameters that are selected to produce a therapeutic result in the patient, i.e., stimulation parameters for each patient are adjusted on an individualized basis. Ordinarily, the amplitude of the stimulation signal is set to the maximum that is comfortable for the patient, and then the other stimulation parameters are adjusted. Preferably, ultrasound imaging of the nerve is also performed when the nerve is preliminarily stimulated electrically, because the stimulation may also cause contraction of nearby muscle (e.g., sternocleidomastoid muscle), which may necessitate some repositioning of the stimulator in order to maintain the nerve in the center of the ultrasound image [IRIARTE J, Artieda J, Alegre M, Schlumberger E, Urrestarazu E, Pastor M A, Viteri C. Spasm of the sternocleidomastoid muscle induced by vagal nerve stimulation. Neurology 57(12, 2001):2319-2320].

Methods and Devices for Evaluating whether the Vagus Nerve is Being Stimulated

The question then arises as to whether the sensation that the patient experiences is due to stimulation of the vagus nerve at a given stimulation amplitude, or whether much of the sensation is due primarily to the stimulation of tissue closer to the skin, such as muscle and skin itself. If the latter were the case, then any therapeutic results from using the vagus nerve stimulator would likely be attributable only to a placebo effect [R WENNBERG. Short term benefit of battery depletion in vagus nerve stimulation for epilepsy. J Neurol Neurosurg Psychiatry 75(6, 2004): 939]. Therefore, tests are performed to determine whether the vagus nerve is in fact being stimulated, one of which is as follows. The human vagus nerve is supplied by a distinct vagal artery and vein that lie on the anterior aspect of the nerve [FERNANDO D A, Lord R S. The blood supply of vagus nerve in the human: its implication in carotid endarterectomy, thyroidectomy and carotid arch aneurectomy. Ann Anat 176(4, 1994):333-337]. When the vagus nerve is electrically stimulated, its metabolic needs increase, such that there is reflex-increased blood flow within the vagal artery and its associated arterioles. Thus, one test for whether the vagus nerve is being stimulated is to measure blood flow in the vagal artery and compare it with the flow when the vagus nerve is not being stimulated. KNAPPERTZ et al (cited above) were unable to delineate the vagal artery with color flow Doppler ultrasound imaging. However, conventional Doppler-based imaging techniques are unable to detect low velocity blood flow in smaller vessels, the chief difficulty being that blood is a weak reflector of ultrasound. One method to overcome this difficulty is to inject brighter ultrasound reflectors than blood into the vascular system. Gas filled microbubbles are one such reflector or contrast agent. Therefore, according to the present invention, one method for demonstrating stimulation of a vagus nerve is to measure an increased (or conceivably decreased) vagal artery blood flow, preferably using ultrasound contrast agents [Matthew BRUCE, Mike Averkiou, and Jeff Powers. Ultrasound contrast in general imaging research. (2007). Philips Medical Systems, Global Information Center, P.O. Box 1286, 5602 BG Eindhoven, The Netherlands, pp. 1-19].

The stimulation vs. non-stimulation issue has also been raised by other investigators in connection with implanted vagus nerve stimulators, but to date there is no agreed upon method for verifying stimulation of the vagus nerve. Furthermore, the methods that have been proposed for verifying the stimulation of an implanted stimulator may not be relevant to the present invention involving non-invasive stimulation. For example, operation of an implanted vagus nerve stimulator may be verified by placing measurement electrodes on the patient's skin above the implant [U.S. Pat. No. 7,228,167, entitled Method and apparatus for detecting vagus nerve stimulation, to KARA et al]. However, in the present invention there are already electrodes placed on the skin above the vagus nerve to perform the stimulation noninvasively, in lieu of stimulating at an internal site. Therefore, in the present invention, subsurface electrical properties within the patient's tissue following a skin-surface electrical stimulation pulse would have to be inferred from skin-surface electrical measurements by estimating currents under the skin, using electrical impedance tomography, electrical resistivity tomography, induced polarization, spectral induced polarization and related electrical pulse-response methods. Field equations that may be used for that purpose were disclosed in co-pending, commonly assigned application Ser. No. 13/075,746, entitled DEVICES AND METHODS FOR NON-INVASIVE ELECTRICAL STIMULATION AND THEIR USE FOR VAGAL NERVE STIMULATION ON THE NECK OF A PATIENT, to SIMON et al, which is hereby incorporated by reference. The use of such methods for demonstrating altered subsurface electrical properties (including electrical changes at a vagus nerve) requires the solution of inverse mathematical equations, which is greatly aided by the availability of a priori anatomical information that is provided by ultrasound imaging, performed as described above.

Other methods for verifying and monitoring stimulation of the vagus nerve are described in paragraphs that follow. In general, they rely on the stimulated vagus nerve causing some physiological response that can be measured, such as some change in the autonomic nervous system, an evoked potential, changes in the chemistry of the blood, or changes in blood flow within the brain that can be measured using PET or functional magnetic resonance imaging [HENRY T R. Therapeutic mechanisms of vagus nerve stimulation. Neurology 59(6 Suppl 4, 2002):53-514]. Preferably, the measured physiological response is one that is mechanistically related to the disease that is being treated. For example, if the patient is a migraine sufferer, the physiological signal may be one related to asymmetric responses of the autonomic nervous system, as evidenced by differences such as left versus right eye pupil responses [HARLE D E, Wolffsohn J S, Evans B J. The pupillary light reflex in migraine. Ophthalmic Physiol Opt 25(3, 2005):240-245].

However, more generally, disease-related responses to vagus nerve stimulation may be slow to occur, and if the patient is being treated with vagus nerve stimulation as a prophylaxis, such responses might be indistinguishable from those experienced by a normal individual. Consequently, when the initial goal is to demonstrate simply that the vagus nerve is in fact being stimulated with a particular stimulation amplitude and other stimulation parameters, usefulness of the test may be evaluated primarily on the basis of the sensitivity of the test-physiological system to vagus nerve stimulation. In devising such a sensitive test, one may look to the physiological systems that are most often perturbed as side effects of vagus nerve stimulation. For implanted vagus nerve stimulators, side-effects that are unrelated to the implantation surgery itself (e.g., incision pain) occur with the following frequency, as reported by a stimulator device manufacturer: voice alteration (33%), pharyngitis (inflammation of the throat) (13%), dysphagia (difficulty swallowing) (11%), hypesthesia (numbness) (11%), nausea (9%), dyspnea (shortness of breath) (9%), headache (8%), neck pain (7%), increased cough (6%), paresthesia (6%) [Depression Patient's Manual for Vagus Nerve Stimulation with the VNS Therapy System. Document REF 26-0005-6000/1, 2004. Cyberonics Inc. 100 Cyberonics Boulevard, Houston, Tex. U.S.A. 77058]. Other investigators report similar findings, except that 55 percent of the patients experienced voice alteration, and a significant number of patients experience arrhythmias as well, possibly because of more relaxed patient exclusion criteria [SACKEIM H A, Rush A J, George M S, Marangell L B, Husain M M, Nahas Z, Johnson C R, Seidman S, Giller C, Haines S, Simpson R K Jr, Goodman R R. Vagus nerve stimulation (VNS) for treatment-resistant depression: efficacy, side effects, and predictors of outcome. Neuropsychopharmacology 25(5, 2001):713-728]. Other investigators report even higher percentages of side-effects related to the patient's voice and larynx. SANTOS reported that 66 percent of patients undergoing invasive vagus nerve stimulation therapy exhibit changes to their vocal fold (vocal cord) functioning, even though not all such patients sense that there has been voice change [SANTOS P M. Evaluation of laryngeal function after implantation of the vagus nerve stimulation device. Otolaryngol Head Neck Surg 129(3, 2003):269-273]. CHAROUS et al found that 95 percent of patients undergoing invasive vagus nerve stimulation have voice changes when the stimulator is first activated [CHAROUS S J, Kempster G, Manders E, Ristanovic R. The effect of vagal nerve stimulation on voice. Laryngoscope 111(11 Pt 1, 2001):2028-2031]. ZALVAN et al found that 100% of such patients exhibit laryngeal dysfunction [ZALVAN C, Sulica L, Wolf S, Cohen J, Gonzalez-Yanes O, Blitzer A. Laryngopharyngeal dysfunction from the implant vagal nerve stimulator. Laryngoscope 113(2, 2003):221-225]. In fact, voice alteration in patients with implanted vagus nerve stimulators is so common that devices have been disclosed that turn off the stimulator when the patient is speaking [U.S. Pat. No. 5,205,285, entitled Voice suppression of vagal stimulation, to BAKER, Jr.].

In view of these data, voice alteration is by far the most common side-effect of vagus nerve stimulation, suggesting that tests of the patient's voice are likely to demonstrate that the vagus nerve is being stimulated. Physiologically, this is understandable because the recurrent laryngeal nerve, a branch of the vagus nerve, enervates muscles of the focal folds (vocal cords) of the larynx and would be expected to be stimulated as a component of the cervical vagus nerve.

Accordingly, the first tests for vagus nerve stimulation that are disclosed below are voice-related. Note, however, that some of the laryngeal side-effects that have accompanied vagus nerve stimulation with implanted stimulators may be due to the fact that the types of patients undergoing the treatment (e.g., epileptics) are also treated with certain drugs that appear to cause dysfunction of the larynx even before the vagus nerve stimulator is implanted [SHAW G Y, Sechtem P, Searl J, Dowdy E S. Predictors of laryngeal complications in patients implanted with the Cyberonics vagal nerve stimulator. Ann Otol Rhinol Laryngol 115(4, 2006): 260-267]. Furthermore, vagus nerve stimulator implantation may damage the vagus nerve, through mishandling of the nerve during the implantation and through electrode migration, inflammatory reaction to a foreign body, and the nature of electrical stimulation from the implanted electrode itself. Therefore, the effects on the larynx from invasive stimulation of the vagus nerve, particularly in patients without epilepsy, would not necessarily correspond to the effects on the larynx found in patients whose vagus nerve is stimulated noninvasively [TRAN Y, Shah A K, Mittal S. Lead breakage and vocal cord paralysis following blunt neck trauma in a patient with vagal nerve stimulator. J Neurol Sci 304(1-2, 2011):132-135].

Some details concerning the effects on the larynx from invasive vagus nerve stimulation have been identified, through use of general methods that are used by otolaryngologists and speech pathologists to evaluate voice pathology. Understanding of those methods and their results requires some background concerning the physiology of the larynx and vocal folds, as follows. The function of the larynx is to modulate the flow and pressure of air entering and leaving the lungs and lower airway. Within the larynx, the glottis is the primary area of control, consisting of the vocal folds (vocal cords or plicae vocals) and the variable gap between them (the rima glottidis). Airflow is regulated differently by the glottis during respiration, coughing, swallowing, and vocalization.

Mechanical support for the larynx (voicebox) at the top of the trachea consists of several cartilaginous structures, including the thyroid, cricoid, arytenoid, cuneiform, corniculate, and epiglottis cartilages. The vocal folds (vocal cords) consist of a pair of infoldings of mucous membrane stretched horizontally across the larynx, attached posteriorly to the arytenoid cartilages, and anteriorly to the thyroid cartilage. When the vocal folds are juxtaposed to one another (adducted), they can vibrate as air is expelled from the lungs, producing speech sounds. During inhalation, they are open (abducted) to allow the free passage of air. Adduction and abduction of the vocal folds are controlled by laryngeal muscles [C. A. ROSEN and C. B. Simpson. Anatomy and physiology of the larynx. Chapter 1 (pp. 3-8). In: C Blake Simpson and Clark A Rosen, Operative Techniques in Laryngology. Berlin: Springer, 2008; SATALOFF R T, Heman-Ackah Y D, Hawkshaw M J. Clinical anatomy and physiology of the voice. Otolaryngol Clin North Am 40(5, 2007):909-929].

Nuanced control of the laryngeal muscles, ultimately by higher centers of the brain that also control respiration, the lips, and tongue, results in coherent speech [BROWN S, Ngan E, Liotti M. A larynx area in the human motor cortex. Cereb Cortex 18(4, 2008):837-845]. That central control of the laryngeal muscles involves not only feedback from sensory nerves within the larynx, tongue, and other airway structures, but also feedback involving the sounds that the speaker hears from his or her own speech [LUDLOW C L. Central nervous system control of the laryngeal muscles in humans. Respir Physiol Neurobiol 147(2-3, 2005):205-222; VANDAELE D J, Cassell M D. Multiple forebrain systems converge on motor neurons innervating the thyroarytenoid muscle. Neuroscience 162(2, 2009):501-524; CHANG E F, Niziolek C A, Knight R T, Nagarajan S S, Houde J F. Human cortical sensorimotor network underlying feedback control of vocal pitch. Proc Natl Acad Sci USA. 110(7, 2013):2653-2658; Sayako MASUDA, Naomi Sakai and Koichi Mori. Neural basis underlying vocal and speech control using auditory feedback. Chapter 11 (pp. 115-125) In: Shigeru Watanabe (ed). CARLS Series of Advanced Study of Logic and Sensibility, Volume 2. Tokyo: Keio University Press (2008); SUSSMAN H M. What the tongue tells the brain. Psychol Bull 77(4, 1972):262-272].

The muscles of the larynx are classified as either intrinsic (confined to the larynx) or extrinsic (attaching the larynx to other structures within the head and neck). Vocal fold movements produced by these muscles may be described as adductor (vocal fold closing) and abductor (opening). Intrinsic laryngeal muscles are usually classified as having either an adductor action (thyroarytenoid, lateral cricoarytenoid and interarytenoid muscles) or abductor function (posterior cricoarytenoid muscle). The cricothyroid muscle, on the other hand, is an intrinsic muscle that serves a different function, namely, to elongate the vocal folds. In addition to the intrinsic muscles, there are also several extrinsic laryngeal muscles that act in concert to provide laryngeal stabilization, but they only indirectly affect the position of the vocal folds.

These intrinsic laryngeal muscles are controlled by the right and left vagus nerves, each of which descends in a carotid sheath giving off three major branches: the pharyngeal branch, the superior laryngeal nerve (SLN), and the recurrent laryngeal nerve (RLN). The RLN arises from the vagus nerve in the upper chest and loops under the aortic arch (left) or subclavian artery (right), and ascends back into the neck, entering the larynx posteriorly. The RLN innervates the ipsilateral posterior cricoarytenoid muscle, the interarytenoid muscle, and the lateral cricoarytenoid muscle, and terminates in the thyroarytenoid muscle. Thus, the RLN supplies all of the intrinsic laryngeal muscles with the exception of the cricothyroid muscle. Muscle innervation is unilateral, except for the interarytenoid muscle, which receives contributions from both left and right RLNs. Consequently, stimulation of a cervical vagus nerve, which branches into the RLN below the site of stimulation, can be expected primarily to modulate the activity of these muscles ipsilaterally, which in turn influences activity of the corresponding vocal fold. To limit the possibility of stimulating the vocal folds, one could stimulate the vagus nerve distal to the RLN far below the neck, but even then the vocal folds might be stimulated indirectly via afferent vagal nerves that send signals to the brainstem and then to the laryngeal center of the brain [Publication US20110301658, entitled Spatially selective vagus nerve stimulation, to YOO et al]. Otherwise, minimizing the effect of vagus nerve stimulation on the larynx would rely on selecting the stimulation parameters with that goal in mind [Publication 20110301659, entitled Vagus nerve stimulation with target effects controlled by adjusting temporal parameters, to YOO et al; YOO P B, Hincapie J G, Hamann J J, Ruble S B, Wolf P D, Grill W M. Selective control of physiological responses by temporally-patterned electrical stimulation of the canine vagus nerve. Conf Proc IEEE Eng Med Biol Soc. 2011; 2011:3107-3110].

The SLN supplies sensation to the larynx, as well as motor input to the cricothyroid muscle, which controls vocal fold lengthening and pitch. Whereas invasive vagus nerve stimulation would not be expected to stimulate the SLN, because the SLN has branched from the vagus nerve at the level of the C1 and C2 vertebra before reaching the site of the implanted electrode, the less localized noninvasive vagus nerve stimulation could conceivably stimulate a branch of the SLN as it descends to the vicinity of the thyroid gland. The anatomical course of the SLN is variable, and damage to the SLN (as well as the RLN) is a major risk factor in thyroid surgery. Considering that the thyroid gland (67 in FIG. 8) is relatively close to the vagus nerve (60 in FIG. 8), which may itself occupy an abnormal location within the carotid sheath, direct noninvasive stimulation of the SLN might occur in some patients [FRIEDMAN M, LoSavio P, Ibrahim H. Superior laryngeal nerve identification and preservation in thyroidectomy. Arch Otolaryngol Head Neck Surg 128(3, 2002):296-303]. However, both invasive and noninvasive vagus nerve stimulation might also result in an indirect stimulation of the SLN, as well as stimulation of a contralateral laryngeal nerve. This is because the electrical stimulation might result in afferent vagal signals that reach the brainstem and brain, which in turn result in the production of SLN motor signals, as well as contralateral RLN motor signals [LUDLOW C L. Central nervous system control of the laryngeal muscles in humans. Respir Physiol Neurobiol 147(2-3, 2005):205-222; ORDELMAN S C, Kornet L, Cornelussen R, Buschman H P, Veltink P H. An indirect component in the evoked compound action potential of the vagal nerve. J Neural Eng 7(6, 2010): 066001: pp 1-9]. However, such laryngeal reflex signals have been sought, but have not yet been observed [Y00 PB, Lubock N B, Hincapie J G, Ruble S B, Hamann J J, Grill W M. High-resolution measurement of electrically-evoked vagus nerve activity in the anesthetized dog. J Neural Eng 10(2, 2013):026003: pp. 1-9].

Damage to the RLN and/or SLN may result in vocal paralysis or paresis. Such damage is not uncommon in patients who have implanted vagus nerve stimulators [SHAFFER M J, Jackson C E, Szabo C A, Simpson C B. Vagal nerve stimulation: clinical and electrophysiological effects on vocal fold function. Ann Otol Rhinol Laryngol 114(1 Pt 1, 2005):7-14; SHAW G Y, Sechtem P, Searl J, Dowdy E S. Predictors of laryngeal complications in patients implanted with the Cyberonics vagal nerve stimulator. Ann Otol Rhinol Laryngol 115(4, 2006):260-267; GHANEM T, Early S V. Vagal nerve stimulator implantation: an otolaryngologist's perspective. Otolaryngol Head Neck Surg 135(1, 2006):46-51; ZALVAN C, Sulica L, Wolf S, Cohen J, Gonzalez-Yanes O, Blitzer A. Laryngopharyngeal dysfunction from the implant vagal nerve stimulator. Laryngoscope 113(2, 2003):221-225; HOERTH M, Drazkowski J, Sirven J, Hinni M, Smith B, Labiner D. Vocal cord paralysis after vagus nerve stimulator battery replacement successfully treated with medialization thyroplasty. Clin Neurol Neurosurg 109(9, 2007):788-790; KALKANIS J G, Krishna P, Espinosa J A, Naritoku D K. Self-inflicted vocal cord paralysis in patients with vagus nerve stimulators. Report of two cases. J Neurosurg 96(5, 2002):949-951]. Vocal fold paralysis implies vocal fold immobility due to neurologic injury. Vocal fold paresis implies vocal fold hypomobility due to neurologic injury and may result from weak muscular stimulation by the RLN, SLN, or both. Vocal fold paresis may present as dysphonia, loss of the upper register of the voice, hoarseness, breathiness, throat pain, choking episodes, or decreased vocal stamina. Clinically, unilateral RLN injury presents as a breathy voice. After a few weeks, the contralateral vocal fold may compensate by adducting further to improve vocal quality and aspiration. Injury to an SLN manifests itself most clearly as a change in voice range. In SLN paresis and paralysis, the loss of function may lead to lowered pitch, a more monotone voice, and poor vocal performance at higher pitches. SLN paresis and paralysis may also cause vocal fatigue, hoarseness, impairment of volume, loss of upper range, loss of projection, and breathiness [RUBIN A D, Sataloff R T. Vocal fold paresis and paralysis. Otolaryngol Clin North Am 40(5, 2007):1109-1131; SULICA L, Blitzer A. Vocal fold paresis: evidence and controversies. Curr Opin Otolaryngol Head Neck Surg 15(3, 2007):159-162; KOUFMAN J A, Postma G N, Cummins M M, Blalock P D. Vocal fold paresis. Otolaryngol Head Neck Surg 122(4, 2000):537-541].

In view of the fact that vocal paralysis or paresis may be caused by an implanted vagus nerve stimulator, U.S. Pat. Nos. 7,801,603 and 8,290,584, both entitled Method and apparatus for optimizing vagal nerve stimulation using laryngeal activity, to WESTLUND et al. appear to be limited in their application, as now explained. Their disclosure includes "an activity indicative of laryngeal activity" and "a neural stimulation input indicative of stimulation of a vagus nerve". A rationale of their disclosure is that "vagal nerve stimulation causes vibration of the larynx through the recurrent laryngeal nerves . . . . Thus, laryngeal activity, including the magnitude and frequency of the vibration of the larynx, provides for an indication of whether the vagus nerve is activated by the neural stimulation. This allows for optimization of therapy without the need to monitor and analyze the target response (such as cardiac remodeling) of the vagal nerve stimulation". "The activity sensor . . . is placed on the neck over the larynx to sense a signal indicative of laryngeal activity," which is said to be an accelerometer. An application of the system is said to be "optimization of electrode placement", which presumably takes place during the surgical implantation of a vagus nerve stimulator while the patient is anesthetized. In fact, nowhere in the disclosure does it indicate that the patient voluntarily participates in activating the larynx, for example, through vocalization, which may be an advantage during surgery. It is possible that the larynx may vibrate as a consequence of the vagus nerve stimulation, as disclosed by WESTLUND et al, and this effect is used in devices that stimulate the vagus nerve to treat voice problems [e.g., U.S. Pat. No. 7,069,082, entitled Pacemaker for bilateral vocal cord autoparalysis, to LINDENTHALER; U.S. Pat. No. 7,840,280, entitled Cranial nerve stimulation to treat a vocal cord disorder, to PARNIS et al]. However, the above-cited references concerning vocal paralysis and paresis resulting from vagus nerve stimulation demonstrate that such stimulation may also inhibit rather than activate vibration of the larynx. Therefore, WESTLUND et al have not disclosed a general method for detecting whether the vagus nerve is being sufficiently stimulated "for optimization of therapy without the need to monitor and analyze the target response." The same critique applies to devices that use implanted or external mechanical sensors other than an accelerometer, such as a microphone or pressure sensor [Publication US20120172741, entitled Systems and methods for using sensed pressure for neurocardiac therapy, to ARCOT-KRISHNAMURTHY et al].

Systems that replace such a mechanical sensor with an electrical sensor of laryngeal muscle activity (essentially laryngeal electromyography, or L-EMG) may work more reliably in detecting activity of the vagus nerve [U.S. Pat. No. 5,111,814, entitled Laryngeal pacemaker, to GOLDFARB; Publication US20110313483 entitled Methods and apparatus for controlling neurostimulation using evoked responses, to HINCAPIE-ORDONEZ et al.;

US20130053926, entitled Systems to detect vagus capture, to HINCAPIE-ORDONEZ et al; SHAFFER M J, Jackson C E, Szabo C A, Simpson C B. Vagal nerve stimulation: clinical and electrophysiological effects on vocal fold function. Ann Otol Rhinol Laryngol 114(1 Pt 1, 2005):7-14; ARDESCH J J, Sikken J R, Veltink P H, van der Aa H E, Hageman G, Buschman H P. Vagus nerve stimulation for epilepsy activates the vocal folds maximally at therapeutic levels. Epilepsy Res 89(2-3, 2010):227-231]. In practice they are similar to conventional LEMG methods, except that a vagus nerve is stimulated invasively, rather than the standard LEMG method of stimulating the spinal accessory nerve. They are also similar to methods used during thyroid and brainstem surgery to monitor the integrity of a vagus nerve, using EMG of a laryngeal muscle as a safety indicator, some of which place the EMG electrode on an endotracheal tube [SEVERTSON M A, Leonetti J P, Jarocki D. Vagal nerve monitoring: a comparison of techniques in a canine model. Am J Otol 18(3, 1997):398-400; FRIEDRICH C, Ulmer C, Rieber F, Kern E, Kohler A, Schymik K, Thon K P, Lamade W. Safety analysis of vagal nerve stimulation for continuous nerve monitoring during thyroid surgery. Laryngoscope 122(9, 2012):1979-1987; DIONIGI G, Chiang F Y, Rausei S, Wu C W, Boni L, Lee K W, Rovera F, Cantone G, Bacuzzi A. Surgical anatomy and neurophysiology of the vagus nerve (VN) for standardized intraoperative neuromonitoring (IONM) of the inferior laryngeal nerve (ILN) during thyroidectomy. Langenbecks Arch Surg 395(7, 2010):893-899; PHELAN E, Potenza A, Slough C, Zurakowski D, Kamani D, Randolph G. Recurrent laryngeal nerve monitoring during thyroid surgery: normative vagal and recurrent laryngeal nerve electrophysiological data. Otolaryngol Head Neck Surg 147(4, 2012):640-646; SINGH R, Husain A M. Neurophysiologic intraoperative monitoring of the glossopharyngeal and vagus nerves. J Clin Neurophysiol. 2011 December; 28(6, 2011):582-586].

However, these EMG methods suffer from the disadvantage that in order to work best, they require the invasive placement of an electrode into a laryngeal muscle [HEMAN-ACKAH Y D, Sataloff R T. Laryngeal EMG: Basic Concepts and Clinical Uses. Journal of Singing 2002; 58(3): 233-238]. Interpretation of such laryngeal EMG signals is also problematic, because virtually every author to address the subject of vocal paresis has remarked on the discrepancy of clinical observations and electromyographic findings [SULICA L, Blitzer A. Vocal fold paresis: evidence and controversies. Curr Opin Otolaryngol Head Neck Surg 15(3, 2007):159-162]. For example, it is not uncommon for paresis to be strongly suggested by visual laryngeal examination, but the electromyographic signals are normal in all muscles tested. The discrepancy may be because each electrode track gives only a limited picture of the activity of the whole muscle, such that the electromyographic electrode would have to be placed at multiple locations within the muscle in order to obtain an accurate representation of nerve-muscle interaction. Furthermore, the signals are influenced by many different confounding activities (e.g., phonating, sniffing, breathing, or swallowing).

According to the present invention, there is a better way to use electromyographic measurements in order to demonstrate that the vagus nerve is being stimulated. The disclosed method relies not on electromyographic measurement per se, but instead relies upon the fact that the electromographic signals should be asymmetric when comparing left versus right muscles. This is because the vagus nerve stimulation is being performed on one side of the neck, so there should be altered laryngeal muscle activity primarily on the ipsilateral side but not on the contralateral side, when the vagus nerve is stimulated. With this in mind, one may use surface electromyographic recordings instead of invasive (intramuscular) recordings, in which the surface EMG electrodes need not be attached to a tracheal tube. Rather than attempt to obtain EMG recordings from separate laryngeal muscles, surface electrodes are placed symmetrically on both sides of the larynx, possibly overlying multiple laryngeal muscles [neck surface locations are illustrated by HIRANO M, Ohala J. Use of hooked-wire electrodes for electromyography of the intrinsic laryngeal muscles. J Speech Hear Res 12(2, 1969):362-373]. Preferably electrode arrays are used. For example, a pair of electromyographic electrode arrays 81 is shown in FIG. 6B. Before the vagus nerve is stimulated electrically, when speech is performed (see HIRANO), the signals across the two arrays behave in a symmetric manner, so as to be able to make correspondence between particular array elements in the two arrays [MERLETTI R, Botter A, Troiano A, Merlo E, Minetto M A. Technology and instrumentation for detection and conditioning of the surface electromyographic signal: state of the art. Clin Biomech (Bristol, Avon) 24(2, 2009):122-134]. Then, as vagus stimulation is applied and its amplitude is increased, the signals from corresponding array elements in the two arrays should become increasingly dissimilar or asymmetric during speech or other laryngeal activity, by virtue of the fact the vagus nerve stimulation is affecting laryngeal muscles primarily or preferentially on the ipsilateral side of the larynx. Thus, in the present invention it is the magnitude of the asymmetry of the EMG signals that is used as an indication of vagus nerve stimulation, rather than the EMG signals per se, even in the presence of confounding simultaneous activity (e.g., phonating, sniffing, breathing, or swallowing). For example, for corresponding left (L) and right (R) array element electromyographic measurement values, the differences with and without nerve stimulation at voltage V may be calculated (Lv−Lo and Rv−Ro), and an asymmetry index for that element may be constructed, such as [(Lv−Lo)/(Lv+Lo)]−[(Rv−Ro)/(Rv+Ro)]. An overall asymmetry index may be calculate from the individual array indices, such as the array element index having the greatest absolute value or the average of all array element indices.

Laryngeal electromyography is one of many techniques that are used to assess or diagnose voice or larynx disorders [Ronald J BAKEN and Robert F Orlikoff. Clinical measurement of speech and voice. Second edition. Clifton Park, N.Y.: Delmar Cengage Learning, 2010; DEJONCKERE P H, Bradley P, Clemente P, et al. A basic protocol for functional assessment of voice pathology, especially for investigating the efficacy of (phonosurgical) treatments and evaluating new assessment techniques. Guideline elaborated by the Committee on Phoniatrics of the European Laryngological Society (ELS). Eur Arch Otorhinolaryngol 258(2, 2001):77-82]. The techniques include performing a spectral analysis of the patient's speech or otherwise performing a time-series analysis of spoken audio signals, laryngoscopic visualization of the vocal folds including high speed cinematography, stroboscopy of the vocal folds, optical measurement of glottis opening, electrical measurement of glottis opening (electroglottography), the measurement of air pressure in regions of the vocal tract, the measurement of airflow as it relates to the aerodynamics of sound generation, and measurements involving the nose, pharynx, and tongue-palate.

The time series analysis of spoken acoustic signals often presupposes that the signal is stationary and periodic, resulting from phonation of a sustained vowel at a constant pitch and intensity level. However, other voice types also exist, namely bifurcating, chaotic and stochastic types [Alicia SPRECHER, Aleksandra Olszewski, and Jack J. Jiang. Updating signal typing in voice: Addition of type 4 signals. J Acoust Soc Am 127(6, 2010): 3710-3716]. To produce periodic acoustic voice signals, the patient is placed in a quiet room, an omnidirectional microphone is placed at a fixed distance from the patient's mouth (e.g. 16 cm), and the patient produces a sustained vowel such as /a/ or /i/ at a loudness and pitch that is comfortable at approximately conversational level. The patient may be provided with earplugs to prevent auditory feedback from influencing the speech. The signal from the microphone is digitized at about 20 to 40 kHz at 16 bits and is then analyzed by computer to calculate acoustic indices. Traditional measurements include FO (the fundamental frequency or pitch of vocal oscillation), absolute sound pressure level (indicating the relative loudness of speech), jitter (the extent of variation in speech F0 from vocal cycle to vocal cycle), shimmer (the extent of variation in speech amplitude from cycle to cycle), and noise-to-harmonics ratios (the amplitude of noise relative to tonal components in the speech) [Will STYLER. Using Praat for Linguistic Research. Boulder, Colo.: University of Colorado at Boulder Phonetics Lab, University of Colorado Linguistics Department, 295 UCB, Boulder Colo. 80309, 2103. pp. 1-70]. In addition to these classical acoustic characterizations of voice, nonlinear dynamical indices have also been calculated, such as the correlation dimension and Lyapunov exponent [Max A. LITTLE, Declan A. E. Costello, and Meredydd L. Harries. Objective dysphonia quantification in vocal fold paralysis: comparing nonlinear with classical measures. J Voice 25(1, 2011): 21-31; Max A LITTLE, Patrick E McSharry, Stephen J Roberts, Declan A E Costello, and Irene M Moroz. Exploiting nonlinear recurrence and fractal scaling properties for voice disorder detection. Biomed Eng Online. 2007; 6: 23. pp. 1-35].

Such classical, but not nonlinear, acoustic indices have been measured from the voices of patients stimulated by an implanted vagus nerve stimulator. However, for reasons described above, it is not clear that these results would apply also to noninvasive vagus nerve stimulation. LUNDY et al found that the indices vary as a function of the vagus nerve stimulation frequency. However, LUNDY et al did not vary the amplitude of the nerve stimulation systematically, so it is not clear how sensitive the indices are to detecting the onset of laryngeal effects. They also measured cardiorespiratory variables but apparently found no significant effects on heartrate or other cardiorespiratory indices [LUNDY D S, Casiano R R, Landy H J, Gallo J, Gallo B, Ramsey R E. Effects of vagal nerve stimulation on laryngeal function. J Voice 7(4, 1993):359-364]. CHAROUS et al reported changes in classical acoustic parameters when the vagus nerve was stimulated, but they did not indicate any of nerve stimulation parameters such as nerve stimulation frequency [CHAROUS S J, Kempster G, Manders E, Ristanovic R. The effect of vagal nerve stimulation on voice. Laryngoscope 111(11 Pt 1, 2001):2028-2031]. KERSING et al also reported changes in classical acoustic parameters when the vagus nerve was stimulated. The stimulation was performed at 30 Hz, and the amplitude of stimulation was increased very slowly over the course of many weeks, during which time the larynx would be adapting to the increased amplitude [KERSING W, Dejonckere P H, van der Aa H E, Buschman H P. Laryngeal and vocal changes during vagus nerve stimulation in epileptic patients. J Voice 16(2, 2002): 251-257].

Because KERSING et al increased the amplitude so gradually, it is not clear how sensitive any of the acoustic indices would be in detecting the onset of laryngeal effects when the vagus nerve stimulation is first applied. ZUMSTEG et al reported that in some patients, laryngeal effects can be detected even at very small vagus nerve stimulation amplitudes, but those effects were observed visually, not through use of any acoustic measurement [ZUMSTEG D, Jenny D, Wieser H G. Vocal cord adduction during vagus nerve stimulation for treatment of epilepsy. Neurology 54(6, 2000)1388-1389]. In view of the limitations of the data that have been reported to date, what is needed is a demonstratively sensitive acoustic method for detecting laryngeal effects from very low-amplitude vagus nerve stimulation, even before any effect becomes clearly noticeable by the patient or bystander. LITTLE et al reported that nonlinear acoustic indices perform at least as well as the classical acoustic indices, but they have not been calculated using voice signals of patients treated with invasive vagus nerve stimulation [Max A. LITTLE, Declan A. E. Costello, and Meredydd L. Harries. Objective dysphonia quantification in vocal fold paralysis: comparing nonlinear with classical measures. J Voice 25(1, 2011):21-31].

In the present context, use of the above-mentioned classical and nonlinear acoustic indices to infer vagus nerve stimulation suffers from two deficiencies. The first is that they make no use of a priori information concerning the asymmetry of vocal fold stimulation, namely, that the vagus nerve stimulation is affecting laryngeal muscles primarily or preferentially on the ipsilateral side of the larynx. The second is that they are limited to situations in which the spoken sound is stationary and periodic, i.e., the patient produces a sustained vowel, which derives from a bias on the part of laryngologists that they would also like to be able to view the vocal folds under a condition suitable for stroboscopic viewing. To address these deficiencies, in the present invention, the patient is also instructed to perform a monotonous pitch raise, wherein the patient phonates a vowel such as /a/ from a low pitch up to a much higher one. Such a maneuver has been used in connection with visualization of the vocal folds, but has apparently never been performed purely for acoustic voice analysis [WURZBACHER T, Schwarz R, Dollinger M, Hoppe U, Eysholdt U, Lohscheller J. Model-based classification of nonstationary vocal fold vibrations. J Acoust Soc Am 120(2, 2006): 1012-1027]. Under such a monotonous pitch raise speech pattern, the effects of laryngeal asymmetries are much more likely to be pronounced, and at some places in the pitch rise, significant deviations from regular periodicity may become apparent, such as biphonation or subharmonic oscillation [EYSHOLDT U, Rosanowski F, Hoppe U. Vocal fold vibration irregularities caused by different types of laryngeal asymmetry. Eur Arch Otorhinolaryngol 260(8, 2003):412-417; MAUNSELL R, Ouaknine M, Giovanni A, Crespo A. Vibratory pattern of vocal folds under tension asymmetry. Otolaryngol Head Neck Surg 135(3, 2006):438-444; SIMPSON C B, May L S, Green J K, Eller R L, Jackson C E. Vibratory asymmetry in mobile vocal folds: is it predictive of vocal fold paresis? Ann Otol Rhinol Laryngol 120(4, 2011):239-242; STEINECKE I, Herzel H. Bifurcations in an asymmetric vocal-fold model. J Acoust Soc Am 97(3, 1995): 1874-1884; XUE Q, Mittal R, Zheng X, Bielamowicz S. A computational study of the effect of vocal-fold asymmetry on phonation. J Acoust Soc Am 128(2, 2010):818-827].

To analyze such a monotonous pitch raise speech pattern (continuous glissando), and optionally a subsequent monotonous pitch decrease speech pattern, the speech is digitized as described above for a sustained vowel; the time-series is broken into many time segments; and the above-described classical and nonlinear speech indices are calculated for each of them. Less common measurements are also made, particularly estimation of the relative power in the first five individual harmonic frequencies, as a complement to the more traditional harmonics-to-noise ratio measurement. Preferably the acoustic signal is nearly stationary within each segment, but if it is not, then either shorter time-segments are used, or the data are detrended within the segment before performing the index calculations. Therefore, the method produces a set of sequences of classical and nonlinear acoustic parameters, which may be interpolated to produce a set of continuous acoustic parameters as a function of time.

The objective in acquiring these monotonous pitch raise (and optionally descending) data is to develop a method that can distinguish between situations in which the noninvasive vagus nerve stimulator is actually stimulating a vagus nerve, versus situations in which it is not. To that end, the procedure described in the previous paragraph is performed with the stimulator applied to the patient's neck, but with different stimulation amplitudes, starting with the control of no stimulation. Thus, one acquires sets of data with which to train a classifier which, after it is trained, can attempt to predict whether an unknown set of data was acquired when nerve stimulation was applied using some non-zero stimulation amplitude. If the classification (stimulation vs. no stimulation) can be made correctly more than some specified percentage of the time (say, 95%), then the data plus the classifier constitute a reliable method for evaluating whether the vagus nerve is being stimulated. The preferred classifier is a support vector machine (SVM), which is an algorithmic approach to the problem of classification within the larger context of supervised learning. A number of classification problems whose solutions in the past have been solved by multi-layer back-propagation neural networks, or more complicated methods, have been found to be more easily solvable by SVMs [Christopher J. C. BURGES. A tutorial on support vector machines for pattern recognition. Data Mining and Knowledge Discovery 2 (1998), 121-167; J. A. K. SUYKENS, J. Vandewalle, B. De Moor. Optimal Control by Least Squares Support Vector Machines. Neural Networks 14 (2001):23-35; SAPANKEVYCH, N. and Sankar, R. Time Series Prediction Using Support Vector Machines: A Survey. IEEE Computational Intelligence Magazine 4(2, 2009): 24-38; PRESS, W H; Teukolsky, S A; Vetterling, W T; Flannery, B P (2007). Section 16.5. Support Vector Machines. In: Numerical Recipes: The Art of Scientific Computing (3rd ed.). New York: Cambridge University Press]. Preferably, the training of the SVM is performed using data from the patient for whom the stimulation decision is to be ultimately made, but training of the SVM may also be attempted using acoustic data obtained from multiple patients.

The set of acoustic data may also be supplemented with simultaneously acquired electroglottographic data as follows, so as to improve the accuracy and sensitivity of the SVM classification (stimulation vs. no stimulation). Electroglottography (EGG) provides information about the closure of vocal folds by measuring the electrical impedance between two (or more) electrodes, placed on the surface of the neck on opposite sides of the larynx [U.S. Pat. No. 4,139,732, entitled Apparatus for speech pattern derivation, to FOURCIN; Adrian FOURCIN. Precision stroboscopy, voice quality and electrolaryngography. Chapter 13 in: Kent R. D. and Ball M. J. (eds) Voice Quality Measurement' (2000) San Diego: Singular Publishing Group, pp 1-32]. The approximate location on one side of the neck of a pair of electrodes 80 that may be used for electroglottography is shown in FIG. 6B. In this embodiment, two pairs of electrodes are used, as described by ROTHENBERG [U.S. Pat. No. 4,909,261, entitled Tracking multielectrode electroglottograph, to ROTHENBERG; Martin ROTHENBERG. A Multichannel Electroglottograph. Journal of Voice 6(1, 1992):36-43]. Because electroglottography needs electrodes on both sides of the neck, the outer surface of electrodes within heads of the vagus nerve stimulator 31 in FIG. 6B may serve as electroglottographic electrodes on the right side of the neck as shown, or separate electrodes 82 may be used for that purpose. Electronics for the electroglottography are housed within the vagus nerve stimulator 30, so lead wires 83 connect the electrodes 80 and 82 (if present) to the stimulator 30. Sinusoidal signals applied to the electroglottograpic electrodes produced by the stimulator 30 are typically in the range 300 kHz to 5 MHz. This frequency is sufficiently high that the current capacitively bypasses the less conductive skin layer, without the need for using conductive electrode gel or paste. Those high frequency, very low amplitude signals are superimposed upon signals that are used for the vagus nerve stimulation itself. Exemplary circuits for measuring the impedance are described by SARVAIYA et al [SARVAIYA J N, Pandey P C, Pandey V K. An impedance detector for glottography. IETE J Res 55 (2009):100-105].

The impedance varies as the space in between the vocal folds (the rima glottidis) opens (increased impedance) and closes (decreased impedance) during each vocal cycle. Alteration of other structures of the larynx in relation to one another will also cause the impedance to fluctuate, for example, as the entire larynx is raised, lowered, and tilted. The EGG data may be acquired as a time series by digitizing at 20 to 40 kHz at 16 bits, then processed with computer programs to extract information about laryngeal function. EGG calculations typically estimate the contact phase of the vibratory cycle, such as the contact quotient (CQ), or evaluate the geometry of the waveform itself [TITZE I R. Parameterization of the glottal area, glottal flow, and vocal fold contact area. J Acoust Soc Am 75(2, 1984):570-580]. Indices that are used for acoustic waveforms may also be calculated with EGG data (e.g., jitter, shimmer) [Nathalie HENRICH, Cedric Gendrot and Alexis Michaud. Tools for Electroglottographic Analysis: Software, Documentation and Databases. Web page archived by the WayBack Machine at the domain voiceresearch.free.fr under the subdomain/egg, pp. 1-4; Martin ROTHENBERG and James J. Mashie. Monitoring vocal fold abduction through vocal fold contact area. Journal of Speech and Hearing Research 31 (1988): 338-351]. Abnormal EGGs are characterized by patterns resembling sine waves that may have a superimposed short (contact) peak and may be used to predict whether laryngeal electromyograms will be abnormal as well [MAYES R W, Jackson-Menaldi C, Dejonckere P H, Moyer C A, Rubin A D. Laryngeal electroglottography as a predictor of laryngeal electromyography. J Voice 22(6, 2008):756-759].

In the present application involving the support vector machine classification of signals involving monotonous pitch raise (and optional subsequent pitch lowering), the entire signal is broken into segments as with the acoustic signal, and parameters are calculated for each segment. Therefore, the method produces a set of sequences of EGG parameters, which may be interpolated to produce a set of continuous EGG parameters as a function of time. These time series are provided to the SVM for training and eventually classification, along with the acoustic data. As the patient changes his or her pitch, the EGG data should be particularly useful for detecting transitions between different forms of phonation, the details of which may be sensitive to the presence of vagus nerve stimulation. Thus, as the patient raises his or her pitch slowly, the larynx shifts from one vocal mode to another at particular frequencies, analogous to an automobile shifting gears, and according to the present invention, the frequencies at which those transitions occur may change depending on the amplitude of vagus nerve stimulation [Nathalie HENRICH, Bernard Roubeau and Michele Castellengo. On the use of electroglottography for characterization of the laryngeal mechanism. Proceedings of the Stockholm Music Acoustics Conference, Aug. 6-9, 2003 (SMAC 03), Stockholm, Sweden, pp. 1-4].

Laryngeal electromyographic L-EMG data as a function of time may also be provided to the support vector machine classifier along with the other data, acquired using electrode arrays 81 shown in FIG. 6B. As described above, the L-EMG data will be in the form of indices of asymmetry between corresponding left and right array elements. Although it is not specifically related to laryngeal function, time-series data describing the respiratory cycle may also be provided to the classifier, because respiration is a part of phonation. The acquisition of a respiratory signal is described below in connection with the use of control-theory methods.

Many other measurements have been suggested for monitoring the effects of stimulating the vagus nerve. For example, FRIEDRICH et al decided that in addition to measurement of laryngeal EMG, heart rate variability and TNF-alpha blood concentration measurements were also to be made, as an indication of effects of the vagus nerve stimulation on the autonomic nervous system and on immunomodulation, respectively [FRIEDRICH C, Ulmer C, Rieber F, Kern E, Kohler A, Schymik K, Thon K P, Lamade W. Safety analysis of vagal nerve stimulation for continuous nerve monitoring during thyroid surgery. Laryngoscope 122 (9, 2012):1979-1987]. The present invention may also make use of autonomic nervous system measurement, which may be used individually or as part of the set of data that are provided to a support vector machine for deciding whether the vagus nerve is being stimulated. The rationale for using autonomic indices is that a primary proximate effect of stimulating a vagus nerve is to alter parasympathetic tone, and alteration of sympathetic tone will follow as a consequence. As described below, the autonomic indices that are preferably measured involve electrodermal responses, heart rate variability and responses related to the control of pupil diameter and blood flow to the eye.

Electrodermal activity (EDA) is due to sweat that is secreted by eccrine sweat glands and excreted through sweat ducts. Secretion by sweat glands is under the control of sympathetic nerves, and consequently, EDA serves as a surrogate of the activity of the sympathetic nervous system, as influenced by central nervous system components [Wolfram BOUCSEIN. Electrodermal activity, 2nd Ed., New York: Springer, 2012, pp. 1-618; Hugo D. CRITCHLEY. Electrodermal responses: what happens in the brain. Neuroscientist 8(2, 2002):132-142; Michael E. DAWSON, Anne M. Schell and Diane L. Filion. The electrodermal system. In: John T. Cacioppo, Louis G. Tassinary and Gary G. Berntson, eds. Handbook of Psychophysiology, 2nd. Ed., Cambridge, UK: Cambridge University press, 2000, Chapter 8, pp. 200-223; FREDRIKSON M, Furmark T, Olsson M T, Fischer H, Andersson J, Langstrom B. Functional neuroanatomical correlates of electrodermal activity: a positron emission tomographic study. Psychophysiology 35(2, 1998):179-85; Henrique SEQUEIRA, Pascal Hot, Laetitia Silvert, Sylvain Delplanque. Electrical autonomic correlates of emotion. International Journal of Psychophysiology 71 (2009): 50-56].

Ordinarily, electrodermal measurement is made on the palm, volar side of a finger, or feet of a patient, although measurement at other sites such as the shoulder may be useful as well [Marieke van DOOREN, J. J. G. (Gert-Jan) de Vries, Joris H. Janssen. Emotional sweating across the body: Comparing 16 different skin conductance measurement locations. Physiology & Behavior 106 (2012): 298-304]. Since 1981, a particular skin conductance method has been the international standard technique to record and analyze electrodermal activity (EDA) [Wolfram BOUCSEIN. Electrodermal activity, 2nd Ed., New York: Springer, 2012, pp. 1-618]. In the present application of determining whether the vagus nerve has been stimulated, the EDA response is measured immediately before, during, and following the nerve stimulation. Miniature electrodermal sensors have become available for use in ambulatory monitoring, which are particularly useful when used in conjunction with an accelerometer [Ming-Zher P O H, Nicholas C. Swenson, and Rosalind W. Picard. A wearable sensor for unobtrusive, long-term assessment of electrodermal activity. IEEE Transactions on Biomedical Engieering 57(5, 2010):1243-1252; Ming-Zher P O H, Tobias Loddenkemper, Nicholas C. Swenson, Shubhi Goyal, Joseph R. Madsen and Rosalind W. Picard. Continuous monitoring of electrodermal activity during epileptic seizures using a wearable sensor. 32nd Annual International Conference of the IEEE EMBS, Buenos Aires, Argentina, Aug. 31-Sep. 4, 2010, pp. 4415-4418; Ming-Zher P O H, Tobias Loddenkemper, Claus Reinsberger, Nicholas C. Swenson, Shubhi Goyal, Mangwe C. Sabtala, Joseph R. Madsen, and Rosalind W. Picard. Convulsive seizure detection using a wrist-worn electrodermal activity and accelerometry biosensor. Epilepsia 53(5, 2012): e93-e97]. Preferably, the electrodermal activity is measured on both sides of the body, so that indices of asymmetry may be calculated as described above in connection with the laryngeal electromyography data.

Several non-invasive measurements other than electrodermal activity can also be used to assess sympathetic activity in a patient, and they may provide an indication of parasympathetic activity as well [MENDES, W. B. Assessing the autonomic nervous system. Chapter 7 In: E. Harmon-Jones and J. Beer (Eds.) Methods in Social Neuroscience. New York: Guilford Press, 2009, pp. 118-147]. One such measurement involves heart rate variability, which may be understood from the fact that both heart rate and electrodermal activity are controlled in part by neural pathways involving, for example, the anterior cingulate cortex [Hugo D. CRITCHLEY, Christopher J. Mathias, Oliver Josephs, et al. Human cingulate cortex and autonomic control: converging neuroimaging and clinical evidence. Brain 126 (2003): 2139-2152; Hugo D. CRITCHLEY. Electrodermal responses: what happens in the brain. Neuroscientist 8(2, 2002)132-142].

Heart rate variability is conventionally assessed by examining the Fourier spectrum of successive heart rate intervals that are extracted from an electrocardiogram (RR-intervals). Typically, a high-frequency respiratory component (0.15 to 0.4 Hz, centered around about 0.25 Hz, and varying with respiration) and a slower, low frequency component (from about 0.04 to 0.13 Hz) due primarily to baroreceptor-mediated regulation of blood pressure related to Mayer waves, are found in the power spectrum of the heart rate. Even slower rhythms (<0.04 Hz), thought to reflect temperature, blood volume, renin-angiotensin regulation, as well as circadian rhythms, may also be present. The high frequency respiratory component is primarily mediated by vagal activity, and consequently, high frequency spectral power is often used as an index of cardiac parasympathetic tone. Low-frequency power can be a valid indicator of cardiac sympathetic activity under certain conditions, with the understanding that baroreceptor regulation of blood pressure can be achieved through both sympathetic and parasympathetic pathways. However, more elaborate indices of sympathetic and parasympathetic activity may also be extracted from the variation in successive heart rate intervals [U. Rajendra ACHARYA, K. Paul Joseph, N. Kannathal, Choo Min Lim and Jasjit S. Suri. Heart rate variability: a review. Medical and Biological Engineering and Computing 44(12, 2006), 1031-1051]. Considering that neither electrodermal nor heart rate variability indices of sympathetic activity unambiguously characterize sympathetic activity within the central nervous system, it is preferred that they both be measured. In fact, additional noninvasive measures of sympathetic activity, such as variability of QT intervals, are preferably measured as well [BOETTGER S, Puta C, Yeragani V K, Donath L, Muller H J, Gabriel H H, Bar K J. Heart rate variability, QT variability, and electrodermal activity during exercise. Med Sci Sports Exerc 42(3, 2010): 443-448].

Most investigations concerning the effect of vagus nerve stimulation on heart rate variability are concerned with long-term effect on particular categories of patients, rather than on acute effects [e.g., RONKAINEN E, Korpelainen J T, Heikkinen E, Myllyla V V, Huikuri H V, Isojarvi J I. Cardiac autonomic control in patients with refractory epilepsy before and during vagus nerve stimulation treatment: a one-year follow-up study. Epilepsia 47(3, 2006):556-562; JANSEN K, Vandeput S, Milosevic M, Ceulemans B, Van Huffel S, Brown L, Penders J, Lagae L. Autonomic effects of refractory epilepsy on heart rate variability in children: influence of intermittent vagus nerve stimulation. Dev Med Child Neurol 53(12, 2011):1143-1149]. Nevertheless, there have been several investigations concerning the acute effects of vagus nerve stimulation on heart rate variability, which demonstrate that heart rate variability could be used as an index of whether the vagus nerve is in fact being stimulated. Most such studies demonstrate unambiguous heart rate variability effects [KAMATH M V, Upton A R, Talalla A, Fallen E L. Effect of vagal nerve electrostimulation on the power spectrum of heart rate variability in man. Pacing Clin Electrophysiol 15(2, 1992):235-243; FREI M G, Osorio I. Left vagus nerve stimulation with the neurocybernetic prosthesis has complex effects on heart rate and on its variability in humans. Epilepsia 42(8, 2001):1007-1016; STEMPER B, Devinsky O, Haendl T, Welsch G, Hilz M J. Effects of vagus nerve stimulation on cardiovascular regulation in patients with epilepsy. Acta Neurol Scand 117(4, 2008):231-236]. However, some investigators have also reported that vagus nerve stimulation has no effect on heart rate variability, which FREI et al attributed to methodological issues [SETTY A B, Vaughn B V, Quint S R, Robertson K R, Messenheimer J A. Heart period variability during vagal nerve stimulation. Seizure 7(3, 1998):213-217].

The diameter of the pupil of the eye is controlled by the autonomic nervous system [John L. BARBUR Learning from the pupil—studies of basic mechanisms and clinical applications. In: L. M. Chalupa and J. S. Werner, Eds. The Visual Neurosciences. Cambridge, Mass.: MIT Press, 2004, Vol. 1, pp. 641-656]. It may cause pupil dilation or constriction not only in response to variations in ambient light, but also in response to other situations, such as an increased level of arousal or alertness. Electrical stimulation of the vagus nerve by itself may cause the pupil to dilate through inhibition of parasympathetic outflow [BIANCA R, Komisaruk B R. Pupil dilatation in response to vagal afferent electrical stimulation is mediated by inhibition of parasympathetic outflow in the rat. Brain Res 1177 (2007):29-36]. However, normal individuals are reported not to have unusual pupil responses, at least to one form of vagus nerve stimulation [Daniela HUBER, Andrea Fischenich, Nadine Wolf, and Jens Ellrich. Transcutaneous vagus nerve stimulation has no impact on the pupillary light reflex in healthy volunteers. Annual Meeting of the Society for Neuroscience, Neuroscience 2012, 13-17 Oct. 2012, New Orleans, La., USA. Society for Neuroscience, 2012. p. No. 657.11/04].

Nevertheless, patients with autonomic dysfunction are often reported as having abnormal pupil responses, and they are likely to be candidates for treatment with vagus nerve stimulation. In particular, patients with migraine, who may also have autonomic dysfunction, are also reported to have pupil response abnormalities, particularly with regard to differences between left and right eyes. Furthermore, the pupils of headache-free migraineurs dilate after a topical application of 1% phenylephrine, whereas this low concentration has at most a minor effect on the pupil diameters of normal individuals [HARLE D E, Wolffsohn J S, Evans B J. The pupillary light reflex in migraine. Ophthalmic Physiol Opt 25(3, 2005):240-245; PEROUTKA S J. Migraine: a chronic sympathetic nervous system disorder. Headache 44(1, 2004):53-64; HORD E D, Evans M S, Mueed S, Adamolekun B, Naritoku D K. The effect of vagus nerve stimulation on migraines. J Pain 4(9, 2003):530-534; BREMNER F D, Smith S E. Pupil abnormalities in selected autonomic neuropathies. J Neuroophthalmol 26(3, 2006): 209-219; MOSEK A, Novak V, Opfer-Gehrking T L, Swanson J W, Low P A. Autonomic dysfunction in migraineurs. Headache 39(2, 1999)108-117]. Even in individuals who do not exhibit initial left-right eye functional asymmetries, such asymmetry may be induced by forcing the individual to breathe only through the left or through the right nostril [BACKON J, Matamoros N, Ramirez M, Sanchez R M, Ferrer J, Brown A, Ticho U. A functional vagotomy induced by unilateral forced right nostril breathing decreases intraocular pressure in open and closed angle glaucoma. Br J Ophthalmol 74(10, 1990):607-609].

Therefore, pupil response in left versus right eyes (e.g., diameter and latency), as a function of left versus right vagus nerve stimulation amplitude and other parameters, left versus right nostril breathing, as a function of ambient light, and as a function of combinations of these, may distinguish whether the left or right vagus nerve is being stimulated at a particular stimulation amplitude. Experimentally, the pupil diameter measurements are preferably performed using infrared cameras, as described by HARLE et al., so as to be able to perform the measurements when the ambient lighting is very low. For example, viewing an infrared image of the pupil can be accomplished with a conventional digital camera after removing the camera's IR-blocking filter and placing a gel filter that blocks visible light in front of the lens. Variations in the pupil measurement procedures, for example those described by BARBUR involving flicker, spatially structured patterns, coherent motion, multi-colored stimuli, situations involving different levels of patient wakefulness, alertness or attention, and transcorneal drug interventions may also be performed in an attempt to find the most sensitive pupillometric test for determining whether a vagus nerve is being electrically stimulated in any particular individual.

The choroid is the vascular layer of the eye, lying between the retina and the sclera. Almost the entire blood supply of the eye comes from the choroidal vessels, which originate from the ophthalmic arteries. The left and right ophthalmic arteries arise as the first major branch of the internal carotid artery. The choroid is vascularized by two separate arterial systems: the short posterior ciliary arteries, which supply the posterior choroid; and the long posterior ciliary arteries, which supply the anterior portion of the choroid, as well as the iris and ciliary body. [B. ANAND-APTE and J. G. Hollyfield. Developmental Anatomy of the Retinal and Choroidal Vasculature In: Joseph C. Besharse, Dean Bok eds. The Retina and Its Disorders, 2011 San Diego, Calif.: Academic Press, pp. 179-185].

The choroid contains dense sympathetic innervation originating in the ipsilateral superior cervical ganglion. Stimulation of the cervical sympathetic trunk, which provides preganglionic innervation to the superior cervical ganglion, diminishes choroidal blood flow. The choroid also receives parasympathetic innervation from the ipsilateral pterygopalatine ganglion, which is vasodilatory. Therefore, the choroid contains sympathetic vasoconstrictor and parasympathetic vasodilator nerves whose activity and interactions determine the level of choroidal perfusion. The sympathetic control is exercised throughout the choroid, and parasympathetic control is more selectively localized [STEINLE J J, Krizsan-Agbas D, Smith P G. Regional regulation of choroidal blood flow by autonomic innervation in the rat. Am J Physiol Regul lntegr Comp Physiol 279(1, 2000):R202-209; BILL A, Sperber G O. Control of retinal and choroidal blood flow. Eye (Lond) 4 (Pt. 2, 1990):319-325]

Choroidal blood flow responds to interventions that cause readjustment of the autonomic nervous system, such as a change of posture, in order to maintain a reflex constancy of perfusion to the eye and also to maintain a constant retinal temperature [KHAYI H, Pepin J L, Geiser M H, Tonini M, Tamisier R, Renard E, Baguet J P, Levy P, Romanet J P, Chiquet C. Choroidal blood flow regulation after posture change or isometric exercise in men with obstructive sleep apnea syndrome. Invest Ophthalmol Vis Sci 52(13, 2011): 9489-9496]. According to the present invention, when the vagus nerve is stimulated, there will also be such a readjustment of the sympathetic and parasympathetic branches of the autonomic nervous system, such that the stimulation will be accompanied by a change in choroidal blood flow. Measurement of that flow may be performed using devices known in the art. For example, KHAYI et al use a laser Doppler method and a confocal optical system with indirect detection of the Doppler shifted light. The instrument uses a coherent near-infrared probing beam (785 nm, 90 microwatt at the cornea). The beam is focused at the fovea, and the subject is asked to look directly at the beam. Light backscattered by the tissue in the sampled volume is collected by a bundle of optic fibers and guided to an avalanche photodiode, the photo-current from which is used to calculate choroidal blood flow [RIVA C E, Geiser M, Petrig B L. Ocular blood flow assessment using continuous laser Doppler flowmetry. Acta Ophthalmol 88(6, 2010):622-629; POLSKA E, Polak K, Luksch A, Fuchsjager-Mayrl G, Petternel V, Findl O, Schmetterer L. Twelve hour reproducibility of choroidal blood flow parameters in healthy subjects. Br J Ophthalmol 88(4, 2004):533-537]. For the pupil diameter and ocular blood flow measurement, the data may be considered separately for each eye, or indices of asymmetry may be calculated as described above in connection with the laryngeal electromyographic data. These data, along with electrodermal and/or heart rate variability data may be presented to the same support vector machine that is used to in connection with the laryngeal data when all such data are collected simultaneously, or otherwise they may be presented to a separate support vector machine for training and prediction of whether a vagus nerve is being stimulated.

During and after vagus nerve stimulation, changes in blood flow near the surface of the skin may also be measured with laser Doppler flow meters. Changes found in most of the skin surface usually reflect changes in sympathetic tone (e.g., blushing or pallor of the face) that is indirectly modulated by the vagus nerve stimulation and may best be monitored by spectral analysis in conjunction with heart rate and respiration variability analysis [SODERSTROM T, Stefanovska A, Veber M, Svensson H. Involvement of sympathetic nerve activity in skin blood flow oscillations in humans. Am J Physiol Heart Circ Physiol 284(5, 2003): H1638-46 BERNARDI L, Rossi M, Fratino P, Finardi G, Mevio E, Orlandi C. Relationship between phasic changes in human skin blood flow and autonomic tone. Microvasc Res 37(1, 1989)16-27]. However, changes of blood flow to specialized surfaces such as the nasal mucosa, lips, mouth, palms of the hand and outer ear canal may have control that reflects additional control by parasympathetic as well as sympathetic arms of the autonomic nervous system. Consequently, changes in blood flow there may be better suited to the inference that vagus nerve stimulation has occurred [MEVIO E, Bernardi L. Phasic changes in human nasal and skin blood flow: relationship with autonomic tone. Ann Otol Rhinol Laryngol 103(10, 1994):789-795; IZUMI H, Karita K. Reflex vasodilatation in the cat lip evoked by stimulation of vagal afferents. J Auton Nery Syst 42(3.1993):215-223]. For paired structures such as the nostrils, differences between flow in the contralateral and ipsilateral sides, relative to the site of vagus nerve stimulation, may also give an indication of whether a vagus nerve has been stimulated.

Although the electrodermal and heart rate variability measurements, along with pupil diameter and blood flow measurements, provide the preferred data concerning autonomic effects demonstrating vagus nerve stimulation, many other autonomic tests may be performed to provide complementary or confirmatory information. It should be noted that there may be significant variation between individuals with regard to evoked autonomic reflexes, and a battery of tests may be useful for those individuals in whom the preferred measurements give equivocal results.

First, consideration may be given to the genetic information about the individual if it is available. Patients at large are known to be particularly polymorphic with respect to their beta-2-adrenergic receptors, which cause significant variation in blood pressure control, vascular responses, and the responses to interventions in diseases such as asthma. Such polymorphism data may be available for an individual in connection with predicting his or her responses to drugs that modulate the autonomic nervous system, some of which may also be used as part of the battery of autonomic tests that are described below [Shelli L. KIRSTEIN and Paul A. Insel. Autonomic nervous system pharmacogenomics: a progress report. Pharmacological Reviews 56(1, 2004):31-52]. Similarly, if the patient is being treated with vagus nerve stimulation for migraine headaches, variable responsiveness among individuals to the stimulation may be attributable in part to genetic factors. Relevant genetic contributions may have already been ascertained in connection with evaluating responsiveness to drugs that the patient has or will receive as previous or concurrent treatment, or at least genetic contributions may be inferred from the fact that the patient responds better to some drugs than others [Maria PAINE, Patrizia Lulli, Ivano Farinelli, Simona Simeoni, Sergio De Filippis, Francesca Romana Patacchioli, and Paolo Martelletti. Genetics of migraine and pharmacogenomics: some considerations. J Headache Pain 8(6, 2007): 334-339].

Second, patients treated with vagus nerve stimulation who suffer from migraine headaches and other disorders may already be known to exhibit autonomic dysfunction [C. MATHIAS. Autonomic diseases: clinical features and laboratory evaluation. J Neurol Neurosurg Psychiatry 74(Suppl 3, 2003): iii31-iii41]. Standard tests that may have been used to evaluate their autonomic function also show considerable inter-patient variability, such that a battery of tests is needed to evaluate autonomic status. The tests ordinarily include the analysis of heart rate variability, as described above. A more complete heart rate variability test is provided by simultaneously measuring heart rate and blood pressure (e.g., with a wrist tonometer), in which beat-to-beat fluctuations in heart rate and blood pressure are correlated. In another common test, the sympathetic skin response test to measure sudomotor function, the patient is subjected to an unexpected stimulus, such as electrical stimulation of the ulnar nerve at the elbow (or in the present application, the vagus nerve), a request for rapid and deep inspiration, a loud noise (hands clapped unexpectedly), or touching to the body unexpectedly. Galvanic skin response is then recorded. Thus, in the present invention, the preferred tests for demonstrating stimulation of the vagus nerve include two tests that are often performed by neurologists when they assess autonomic function in a patient, namely heart rate variability and sympathetic skin response.

Additional autonomic tests that may be performed before, during, and after vagus nerve stimulation are as follows. A valsalva maneuver evaluates the baroreflex arc, in which the patient breathes into a special mouthpiece and maintains an expiratory pressure of 40 mg for 15 to 20 seconds. Heart rate (and optionally beat-to-beat blood pressure, e.g., with a wrist tonometric device) is monitored, and their time course gives an indication of sympathetic and parasympathetic function. Deep metronomic breathing testing at 6 breaths per minute assesses respiratory sinus arrhythmia through an analysis of the corresponding heart rate.

In the sustained handgrip test to test sympathetic activity, the patient presses a handgrip dynamometer at full strength, and then maintains a grip for 3 to 5 minutes at one-third of the maximum. The time course of heart rate and beat-to-beat blood pressure gives an indication of early vagal withdrawal followed by sympathetic activation. In the cold pressor test, e.g., to evaluate sympathetic efferent nerves, one hand and arm are placed in ice water for 40 to 180 seconds. Heart rate, blood pressure, and peripheral blood flow (by laser Doppler flowmetry) are measured. In the cold face test, cold compresses (1.degree. C. to 2.degree. C.) are applied to the forehead and maxillary region of the subject's face for a period of 1 to 3 minutes. Heart rate and beat-to-beat blood pressure responses are then measured, such that a disturbance in the trigeminal-brainstem-vagal reflex arc would produce an abnormal response.

In orthostatic challenge maneuvers, the patient is initially in a recumbent position, and then assumes an upright position, either by actively standing or by being passively rotated to typically 60 or 70 degrees on a table that tilts. The responses in heart rate and blood pressure responses are then monitored. In a mental arithmetic test, the patient is asked to count backwards from 100 subtracting 7 or 13 each time, and changes in systolic blood pressure are recorded.

In pharmacological baroreflex testing, pressor or depressor drugs are infused to increase or decrease the blood pressure, and the heart rate and blood pressure responses are monitored. In neck chamber baroreflex testing, positive or negative pressure is applied to a collar around the neck. The heart rate and blood pressure responses are then recorded. In a lower body negative pressure test, a similar device is applied to the lower portion of the patient's body.

In a thermoregulatory sweat test, the patient is placed in a chamber in which humidity (35-40%) and temperature (45-50 degrees C.) are regulated. Body areas having abnormal sweating patterns are then documented, from which it is inferred that certain axons may be functioning abnormally. In the quantitative sudomotor axon reflex test (QSART) to measure the autonomic nerves that control sweating, electrical stimulation on the skin (iontophoresis), allows acetylcholine to stimulate sweat glands. The QSART measures the volume of sweat produced by this stimulation [Safwan S. JARADEH, Thomas E. Prieto. Evaluation of the autonomic nervous system. Phys Med Rehabil Clin N Am 14 (2003) 287-305; HILZ M J, Dutsch M. Quantitative studies of autonomic function. Muscle Nerve 33(1, 2006):6-20; Agnieszka ZYGMUNT and Jerzy Stanczyk. Methods of evaluation of autonomic nervous system function. Arch Med Sci 6(1, 2010): 11-18; Heinz LAHRMANN, Isabel Rocha, Walter Struhal, Roland D Thijs, and Max Hilz. Diagnosing Autonomic Nervous System Disorders-Existing Guidelines and Future Perspectives. European Neurological Review 6(1, 2011):52-56; H TANAKA and H Tamai. Recent advances in autonomic function tests of the cardiovascular system in children. Medical Principles and Practice 7 (1998):157-171; ILLIGENS B M, Gibbons C H. Sweat testing to evaluate autonomic function. Clin Auton Res 19 (2, 2009):79-87; KUCERA P, Goldenberg Z, Kurca E. Sympathetic skin response: review of the method and its clinical use. Bratisl Lek Listy 105(3, 2004)108-116]. WEIMER gives a more complete list of autonomic tests, noting that pupillometry is considered to be investigational [WEIMER L H. Autonomic testing: common techniques and clinical applications. Neurologist 16(4, 2010):215-222].

The most detailed investigations of blood flow changes following vagus nerve stimulation have dealt with flow changes within the brain itself. Transcranial Doppler flow meters have been used unsuccessfully in an attempt to measure changes in cerebral blood flow [NEU P, Heuser I, Bajbouj M. Cerebral blood flow during vagus nerve stimulation—a transcranial Doppler study. Neuropsychobiology 51(4, 2005):265-268]. However, three imaging methods have demonstrated changes in cerebral blood flow after vagus nerve stimulation, namely: positron emission tomography (e.g., PET with oxygen-15 labeled water), functional magnetic resonance imaging (fMRI), and single-photon emission computed tomography (SPECT, e.g. with 99 mTc-ethyl cysteinate dimer).

Examples of PET imaging during vagus nerve stimulation are given by HENRY et al and by CONWAY et al [HENRY T R, Votaw J R, Pennell P B, Epstein C M, Bakay R A, Faber T L, Grafton S T, Hoffman J M. Acute blood flow changes and efficacy of vagus nerve stimulation in partial epilepsy. Neurology 52(6, 1999):1166-1173; CONWAY C R, Sheline Y I, Chibnall J T, George M S, Fletcher J W, Mintun M A. Cerebral blood flow changes during vagus nerve stimulation for depression. Psychiatry Res. 146(2, 2006)179-184].

Examples of fMRI imaging during vagus nerve stimulation are given by NARAYANAN et al, LIU et al, and KRAUS et al [NARAYANAN J T, Watts R, Haddad N, Labar D R, Li P M, Filippi C G. Cerebral activation during vagus nerve stimulation: A functional MR study. Epilepsia. 43 (2002):1509-1514; W-C LIU, K Mosier, A J Kalnin, D Marks. BOLD fMRI activation induced by vagus nerve stimulation in seizure patients. J Neurol Neurosurg Psychiatry 74 (2003):811-813; KRAUS T, Hosl K, Kiess O, Schanze A, Kornhuber J, Forster C. BOLD fMRI deactivation of limbic and temporal brain structures and mood enhancing effect by transcutaneous vagus nerve stimulation. J Neural Transm 114(11, 2007)1485-1493].

An example of SPECT imaging during vagus nerve stimulation is given by VAN LAERE et al [VAN LAERE K, Vonck K, Boon P, Brans B, Vandekerckhove T, Dierckx R. Vagus nerve stimulation in refractory epilepsy: SPECT activation study. J Nucl Med 41(7, 2000)1145-1154]. The objective of these investigations was to determine which brain structures are activated or deactivated during vagus nerve stimulation. However, in the present context, the finding that there are any differences in cerebral blood flow as the result of vagus nerve stimulation would constitute evidence that the vagus nerve was in fact stimulated. The different imaging studies were reviewed by CHAE et al. and by BARI et al., which indicate that imaging by these methods often gives inconsistent and even contradictory results regarding the particular brain structures that are activated [CHAE J H, Nahas Z, Lomarev M, Denslow S, Lorberbaum J P, Bohning D E, George M S. A review of functional neuroimaging studies of vagus nerve stimulation (VNS). J Psychiatry Res. 37(6, 2003):443-55; Ausaf A. BARI and Nader Pouratian. Brain imaging correlates of peripheral nerve stimulation. Surg Neurol Int 3(Suppl 4, 2012): S260-S268].

Additional tests of whether the vagus nerve is being stimulated may involve the measurement of evoked potentials, as now described. An evoked potential or evoked response is an electrical potential recorded from the nervous system following presentation of a stimulus, as distinct from spontaneous potentials detected by electroencephalography (EEG) or other electrophysiological recording methods. Usually the term "evoked potential" is reserved for responses involving either recording from, or stimulation of, central nervous system structures. An "event-related potential" is the measured brain response that is the direct result of a specific sensory, cognitive, or motor event. The stimulus event in the present context is vagus nerve stimulation, but other stimuli may also be presented to the patient (e.g., visual or auditory). Event-related potentials are measured with electroencephalography (EEG) or more generally with scalp sensors CASSON A, Yates D, Smith S, Duncan J, Rodriguez-Villegas E. Wearable electroencephalography. What is it, why is it needed, and what does it entail? IEEE Eng Med Biol Mag. 29(3, 2010):44-56; ATSUMORI H, Kiguchi M, Obata A, Sato H, Katura T, Funane T, Maki A. Development of wearable optical topography system for mapping the prefrontal cortex activation. Rev Sci Instrum. 2009 April; 80(4):043704, pp. 1-6]. Signal processing methods, comprising not only the application of conventional linear filters to the raw EEG data, but also the nearly real-time extraction of non-linear signal features from the data, may be considered to be a part of the EEG recording [D. Puthankattil SUBHA, Paul K. Joseph, Rajendra Acharya U, and Choo Min Lim. EEG signal analysis: A survey. J Med Syst 34 (2010)195-212]. The magnetoencephalography (MEG) equivalent of event-related potential is the event-related field.

The effects of vagus nerve stimulation on surface EEG waveforms may be difficult to detect [Michael BEWERNITZ, Georges Ghacibeh, Onur Seref, Panos M. Pardalos, Chang-Chia Liu, and Basim Uthman. Quantification of the impact of vagus nerve stimulation parameters on electroencephalographic measures. AIP Conf. Proc. DATA MINING, SYSTEMS ANALYSIS AND OPTIMIZATION IN BIOMEDICINE; Nov. 5, 2007, Volume 953, pp. 206-219; Michael Andrew BEWERNITZ. Data mining and time series analysis of brain dynamical behavior with applications in epilepsy. PhD. Dissertation. Gainesville, Fla.: University of Florida. 2008. pp: 1-246]. However, they may exist nevertheless [KOO B. EEG changes with vagus nerve stimulation. J Clin Neurophysiol. 18(5, 2001):434-41; KUBA R, Guzaninova M, Brazdil M, Novak Z, Chrastina J, Rektor I. Effect of vagal nerve stimulation on interictal epileptiform discharges: a scalp EEG study. Epilepsia. 43(10, 2002):1181-8; RIZZO P, Beelke M, De Carli F, Canovaro P, Nobili L, Robert A, Formaro P, Tanganelli P, Regesta G, Ferrillo F. Modifications of sleep EEG induced by chronic vagus nerve stimulation in patients affected by refractory epilepsy. Clin Neurophysiol. 115(3, 2004):658-64]. By including the analysis of ECG data with EEG data, the diagnostic value of the EEG may be improved [M. VALDERRAMA, S. Nikolopoulos, C. Adam, Vincent Navarro and M. Le Van Quyen. Patient-specific seizure prediction using a multi-feature and multi-modal EEG-ECG classification. XII Mediterranean Conference on Medical and Biological Engineering and Computing 2010, IFMBE Proceedings, 2010, Volume 29, Part 1, 77-80]. In addition, the use of a wavelet transform of the EEG data may enable the detection of effects on different spectral components [Zhaoyang CHEN, Hongwei Hao, Luming Li, Jie Dong. Wavelet Transform for Rabbit EEG with Vagus Nerve Electric Stimulation. Proceedings of the 28th IEEE EMBS Annual International Conference New York City, USA, Aug. 30-Sep. 3, 2006 pp. 1715-1718].

HENRY reviewed the effects of vagus nerve stimulation on evoked potentials and noted that investigators have obtained contradictory results [HENRY TR. Therapeutic mechanisms of vagus nerve stimulation. Neurology 59(6 Suppl 4, 2002):53-514]. BRAZDIL found that vagus nerve stimulation has no effect on auditory evoked potentials but found some effect on visual evoked potentials [BRAZDIL M, Chadim P, Daniel P, Kuba R, Rektor I, Novak Z, Chrastina J. Effect of vagal nerve stimulation on auditory and visual event-related potentials. Eur J Neurol 8(5, 2001): 457-461]. CONTE et al found that for patients undergoing vagus nerve stimulation, Fourier analysis of responses to stimuli identifies alterations in visual evoked potentials that are not found with standard analysis of latencies and amplitude response [Mary M. CONTE and Jonathan D. Victor. VEP indices of cortical lateral interactions in epilepsy treatment. Vision Res 49(9, 2009): 898-906]. POLAK and colleagues found that auricular vagus nerve stimulation resulted in somatosensory-evoked potentials that were characterized by significantly longer latencies as compared to controls [POLAK T, Ehlis A C, Langer J B, Plichta M M, Metzger F, Ringel T M, Fallgatter A J. Non-invasive measurement of vagus activity in the brainstem—a methodological progress towards earlier diagnosis of dementias? J Neural Transm. 2007; 114(5, 2007):613-619; POLAK T, Markulin F, Ehlis A C, Langer J B, Ringel T M, Fallgatter A J. Far field potentials from brain stem after transcutaneous vagus nerve stimulation: optimization of stimulation and recording parameters. J Neural Transm 116(10, 2009):1237-1242]. USAMI et al found that evoked potentials from vagus nerve stimulation are most likely generated by vagal afferents at the jugular foramen near the entrance to the cranium, but some components are due to excitation of laryngeal muscles [USAMI K, Kawai K, Sonoo M, Saito N. Scalp-recorded evoked potentials as a marker for afferent nerve impulse in clinical vagus nerve stimulation. Brain Stimul. 2012 Oct. 11. pii: 51935-861X(12)00161-1, pp. 1-9].

Reported effects of vagus nerve stimulation on physiological variables measured as vital signs have been contradictory, such as effects on absolute heart rate (as opposed to heart rate variability), respiratory frequency, and blood pressure. Differences in the reported effects most likely reflect differences in which nerve fibers are stimulated, which are a function of the amplitude and other parameters of the vagus nerve stimulation. For example, BINKS et al reported that vagus nerve stimulation has no cardiorespiratory effects, provided that no C fibers are stimulated [BINKS A P, Paydarfar D, Schachter S C, Guz A, Banzett R B. High strength stimulation of the vagus nerve in awake humans: a lack of cardiorespiratory effects. Respir Physiol 127(2-3, 2001):125-133]. On the other hand, ZAAIMI et al reported that vagus nerve stimulation has a pronounced effect on respiration; HASHIBA reported that vagus nerve stimulation can induce bradycardia and bronchoconstriction if C fibers are activated; YOO et al reported that vagus nerve stimulation can induce bradycardia; FREI et al reported complex effects such as bradycardia followed by tachycardia; PLACHTA et al demonstrated that it is possible to use vagus nerve stimulation to modulate blood pressure without changing heart rate or respiration rate [ZAAIMI B, Heberle C, Berquin P, Pruvost M, Grebe R, Wallois F. Vagus nerve stimulation induces concomitant respiratory alterations and a decrease in SaO2 in children. Epilepsia. 2005 November; 46(11, 2005):1802-1809; HASHIBA E, Hirota K, Suzuki K, Matsuki A. Effects of propofol on bronchoconstriction and bradycardia induced by vagal nerve stimulation. Acta Anaesthesiol Scand. 2003 October; 47(9, 2003):1059-1063; YOO P B, Hincapie J G, Hamann J J, Ruble S B, Wolf P D, Grill W M. Selective control of physiological responses by temporally-patterned electrical stimulation of the canine vagus nerve. Conf Proc IEEE Eng Med Biol Soc. 2011; 2011:3107-3110; FREI MG, Osorio I. Left vagus nerve stimulation with the neurocybernetic prosthesis has complex effects on heart rate and on its variability in humans. Epilepsia 42(8, 2001):1007-1016; Dennis T. T. PLACHTA, Oscar Cota, Nayeli Espinosa, Thomas Stieglitz, and Mortimer Gierthmuehlen. Selective stimulation of the vagus nerve controls the blood pressure and simultaneously avoids significant side effects of bradycardia and bradypnea. Proceedings of Technically Assisted Rehabilitation (TAR 2013), 4th European Conference, Mar. 14-15, 2013 in Berlin, Session 9, Event 2: pp. 1-4]. This is to say that changes in vital signs that accompany vagus nerve stimulation may serve to demonstrate that the nerve is being stimulated, but also that the parameters of the stimulation may not be optimal if such side effects occur.

Other tests for whether the vagus nerve is being stimulated include changes in pain threshold, changes in balance or sway, and changes in the chemistry of blood or other bodily fluids. NESS et al found that vagus nerve stimulation produces a change in the threshold for pain, which was measured by a thermode applied to the skin of the forearm [NESS T J, Fillingim R B, Randich A, Backensto E M, Faught E. Low intensity vagal nerve stimulation lowers human thermal pain thresholds. Pain 86(1-2, 2000):81-85]. CLARKE et al found that vagus nerve stimulation has no significant effects on bodily sway with eyes open and closed, although limitations to the study were noted by the investigators [CLARKE B M, Upton A R, Kamath M, Griffin H M. Electrostimulation effects of the vagus nerve on balance in epilepsy. Pacing Clin Electrophysiol 15(10 Pt 2, 1992): 1614-1630]. For patients who experience tremor or gait problems, comparing balance tests before and after vagus nerve stimulation, as well as electromyography during effort and standard tests of gait (e.g., Rhomberg test), may be used to demonstrate that the vagus nerve is being simulated.

Vagus nerve stimulation does not cause significant changes in hematology or common blood chemistry values over an extended period of time, but acute changes have apparently not been investigated [SCHACHTER S C, Saper C B. Vagus nerve stimulation. Epilepsia 39(7, 1998):677-686; HANDFORTH A, DeGiorgio C M, Schachter S C, et al. Vagus nerve stimulation therapy for partial-onset seizures: a randomized active-control trial. Neurology 51(1, 1998):48-55]. A general blood marker of vagus nerve stimulation is the circulating level of TNF-alpha compared before/after stimulation. Alternatively, cytokines such as IL-1B, IL-6, IL-8 and IL-10 or other markers for inflammation may be used as a biomarker for vagus nerve stimulation [CORCORAN C, Connor T J, O'Keane V, Garland MR. The effects of vagus nerve stimulation on pro- and anti-inflammatory cytokines in humans: a preliminary report. Neuroimmunomodulation 12(5, 2005):307-309; SLOAN R P, McCreath H, Tracey K J, Sidney S, Liu K, Seeman T. RR interval variability is inversely related to inflammatory markers: the CARDIA study. Mol Med 13(3-4, 2007)178-184].

One may also use other blood-borne chemicals as biomarkers for vagus nerve stimulation, especially if they are relevant to the disease being treated. For example, circulating serotonin has many cardiovascular effects that might be useful therapeutically or that may cause side effects. Release of serotonin from the enterochromaffin cells of the gut is regulated by the vagus nerve, and its release into the portal circulation is controlled by vagal efferent adrenergic nerve fibers [GRONSTAD K O, Zinner M J, Nilsson O, Dahlstrom A, Jaffe B M, Ahlman H. Vagal release of serotonin into gut lumen and portal circulation via separate control mechanisms. J Surg Res 44(2, 1988):146-151; PETTERSSON G. The neural control of the serotonin content in mammalian enterochromaffin cells. Acta Physiol Scand Suppl 470 (1979):1-30]. Another example is the blood level of gastrin in a fasting individual, before versus after vagus nerve stimulation [H. T. DEBAS and S. H. Carvajal. Vagal regulation of acid secretion and gastrin release. Yale J Biol Med 67(3-4, 1994): 145-151]. Another example is the circulating level of noradrenaline in the supine versus standing positions.

Studies on the long-term effect of vagus nerve stimulation on the composition of cerebrospinal fluid (CSF) have also been performed, but apparently no studies concerning acute stimulation effects have been performed [HENRY TR. Therapeutic mechanisms of vagus nerve stimulation. Neurology 59(6 Suppl 4, 2002):53-514]. Considering that collecting such acute data would involve performing a lumbar puncture, it would be difficult to justify using CSF composition as a biomarker for acute vagus stimulation. The chemical composition of urine (e.g., noradrenaline level), sweat, and/or saliva may also show slight changes following vagus nerve stimulation, but a greater effect of the stimulation is likely to be on the volume of their production, through mechanisms involving the autonomic nervous system, tests for which were described in previous paragraphs.

Vagus Nerve Self-Stimulation by the Patient

When a patient is using the stimulation device to perform self-stimulation therapy, e.g., at home or at a workplace, he or she will follow the steps that are now described. In the following description, it is assumed that the stimulator (30 in FIG. 3) has been placed in a docking station (40 in FIG. 3), where it would ordinarily be placed between stimulation sessions for protection and safekeeping. The previous stimulation session will ordinarily have discharged the rechargeable batteries of the stimulator housing, and between sessions, the docking station will have recharged the stimulator at most only up to a minimum level. If the stimulator's batteries had charge remaining from the previous stimulation session, the docking station will have discharged the stimulator to a minimum level that will not support stimulation of the patient.

The patient will then interact with the mated docking station and stimulator via one of the handheld or internet-based devices (333 in FIG. 5), to which the docking station can be connected wirelessly or through a cable. For example, the patient can initiate the stimulation session using a mobile phone (FIG. 4B) or laptop computer (FIG. 4D) by invoking a computer program (on the laptop computer or through an app on the mobile phone) that is designed to initiate use of the stimulator. For security reasons, the program would begin with the request for a user name and a password, and that user's demographic information and any data from previous stimulator experiences would already be associated with it in the login account. If the patient's physician has not authorized further treatments, the docking station will not charge the stimulator's batteries, and instead, the computer program will call or otherwise communicate with the physician's computer requesting authorization. After authorization by the physician is received, the computer program (on the laptop computer or through an app on the mobile phone) may also query a database that is ordinarily located somewhere on the internet to verify that the patient's account is in order. If it is not in order, the program may then request prepayment for one or more stimulation sessions, which would be paid by the patient using a credit card, debit card, PayPal or the like. The computer program will also query its internal database or that of the docking station to determine that sufficient time has elapsed between when the stimulator was last placed in the docking station and the present time, to verify that any required wait-time has elapsed.

Having received authorization to perform a nerve stimulation session, the patient interface computer program will then ask the patient questions that are relevant to the selection of parameters that the docking station will use to make the stimulator ready for the stimulation session. The questions that the computer program asks are dependent on the condition for which the patient is being treated, which for present purposes is considered to be treatment for a migraine headache. That headache may in principle be in any of the headache phases (prodrome, aura, headache pain, postdrome, and interictal period), which would be ascertained through the computer program's questions. The questions may be things like (1) is this an acute or prophylactic treatment? (2) if acute, then how severe is your headache, how long have you had it, (3) has anything unusual or noteworthy occurred since the last stimulation?, etc. In general, the types of posed questions are ones that would be placed in a headache diary [TASSORELLI C, Sances G, Allena M, Ghiotto N, Bendtsen L, Olesen J, Nappi G, Jensen R. The usefulness and applicability of a basic headache diary before first consultation: results of a pilot study conducted in two centers. Cephalalgia 28(10, 2008):1023-1030].

After having received such preliminary information from the patient, the computer program will then send data to the docking station, giving it the instructions needed to perform instrument diagnostic tests of the stimulator and docking station and to make the stimulator ready for the stimulation session. In general, the algorithm for setting the stimulator parameters will have been decided by the physician and will include the extent to which the stimulator batteries should be charged, which the vagus nerve should be stimulated (right or left), and the time that the patient must wait after the stimulation session is ended until initiation of a subsequent stimulation session. The computer will query the physician's computer to ascertain whether there have been any updates to the algorithm, and if not, will use the existing algorithm. The patient will also be advised of the stimulation session parameter values by the interface computer program, so as to know what to expect.

Once the docking station has rapidly charged the stimulator's batteries to the requisite charge, a light will turn on (e.g., green) on the front of the docking station. At that point, the patient may remove the stimulator from the docking station to begin the vagus nerve stimulation, as shown in FIG. 6. The present invention discloses methods to assure that the patient places the stimulator at an optimal position on the neck, the position having been determined previously by a healthcare provider using ultrasound imaging and/or an evaluation of the neck location at which the vagus nerve stimulation produces an optimal physiological response. As described above, the preferred stimulation position on the patient's neck can be marked by the healthcare provider by inserting a dye-soaked cotton swab through "wormhole" ducts within the centerpiece (46 in FIG. 3A) of a stimulator. The swab enters through an entrance port (48 in FIG. 3A) and eventually reaches the patient's skin at an exit port (49 in FIG. 3A), where it stains the patient's skin.

The preferred type of dye is a fluorophore that is only visible or detectable as a spot on the patient's neck when one shines non-visible light upon it, e.g., ultraviolet light ("blacklight") or infrared light. This is because the patient is thereby spared the embarrassment of explaining why there would otherwise be a visible spot marks on his or her neck, and also because such a dye is suitable for showing where to place the stimulator irrespective of whether the patient is dark-skinned or light-skinned. Another method, which is to attempt to match the color of the dye to the patient's flesh color, would be generally impractical. Marking with a fluorescent dye (e.g., from ordinary highlighting pens) has also been performed by surgeons and radiologists to outline where a procedure is to be performed. However, the marking in the present invention is different in that it is intended to be used repeatedly by a patient alone for device-positioning at small discrete spots, and fluorescence from the marked spots is actually measured here by the stimulator, rather than being simply imaged or viewed [DAVID, J. E., Castle, S. K. B., and Mossi, K. M. Localization tattoos: an alternative method using fluorescent inks. Radiation Therapist 15 (2006):1-5; WATANABE M, Tsunoda A, Narita K, Kusano M, Miwa M. Colonic tattooing using fluorescence imaging with light-emitting diode-activated indocyanine green: a feasibility study. Surg Today 39(3, 2009):214-218].

Once the position-indicating spots have been made on the patient's skin as described above, they will fade and eventually disappear as the stained outer surface of the patient's skin exfoliates. The exfoliation will occur naturally as the patient washes his or her neck and may be accelerated by mechanical (e.g., abrasive) or chemical methods that are routinely used by cosmetologists. Before the spot disappears, the patient or a family member may reapply the dye/fluorophor to the same spot while observing it with ultraviolet or infrared light (as the case may be), by masking the skin outside the spot and then applying new dye solution directly with a cotton swab. Viewing of the fluorescence from ultraviolet light can be done with the naked eye, and viewing of fluorescence from infrared light can be done with a conventional digital camera after removing the camera's IR-blocking filter. Some of the infrared fluorescent dyes may also be faintly visible to the naked eye even under room light, depending on their concentration (e.g., indocyanine green).

Alternatively, a semi-permanent or permanent tattooing method of re-marking the spots may be used by a licensed professional tattooer, by injecting the dye/fluorophor into an outer skin layer or deeper into the skin, respectively [Maria Luisa Perez-COTAPOS, Christa De Cuyper, and Laura Cossio. Tattooing and scarring: techniques and complications. In: Christa de Cuyper and Maria Luisa Cotapos (Eds.). Dermatologic Complications with Body Art: Tattoos, Piercings and Permanent Make-Up. Berlin and London: Springer, 2009, pp. 31-32]. Many dyes can be used for the ultraviolet marking, but the most convenient ones for skin-surface marking are those that are commercially available to hand-stamp attendees of events. For tattooing applications, ultraviolet-absorbing injectable fluorophores are commercially available that are encapsulated within microspheres [Technical sheet for Opticz UV Blacklight Reactive Blue Invisible Ink. 2013. Blacklight.com, 26735 W Commerce Dr Step 705, Volo, Ill. 60073-9658; Richard P. HAUGLAND. Fluorophores excited with UV light. Section 1.7 In: The Molecular Probes Handbook: A Guide to Fluorescent Probes and Labeling Technologies, 11th Edition, 2010. Molecular Probes/Life Technologies. 4849 Pitchford Ave., Eugene, Oreg. 97402. pp. 66-73; Technical sheet for BIOMATRIX System. 2013. NEWWEST Technologies, Santa Rosa Calif. 95407-0286].

Many dyes can also be used for the infrared marking, their major advantage being that autofluorescence from human skin or tissue generally does not interfere with detection of their fluorescence. In fact, they may be imaged two centimeters under the skin. Examples of such dyes are indocyanine green and Alexa Fluor 790. Quantum dots may also be used to generate infrared fluorescence, advantages of which are that they are very stable and very brightly fluorescent. They may also be encapsulated in microspheres for purposes of tattooing. Quantum dots may also be electroluminescent, such that the electric field and currents produced by the stimulator might alone induce the emission of infrared light from the quantum dots. They might be imaged even if the quantum dots were deep in the vicinity of the vagus nerve, owing to the lack of bodily autofluorescence in infrared windows. For example, if they were injected into the circulation, electroluminescence from the vagal artery may be imaged, provided that the electric field from the vagus nerve stimulator penetrates to that depth, and their electroluminescent intensity should be proportional to the amplitude of the stimulation electric field. Alternatively, the quantum dots may be injected into the skin to the vicinity of the vagus nerve, whereupon their electroluminescence would demonstrate an electric field that penetrated to that depth [Richard P. HAUGLAND. Alexa Fluor Dyes Spanning the Visible and Infrared Spectrum—Section 1.3; and Qdot Nanocrystals—Section 6.6. In: The Molecular Probes Handbook: A Guide to Fluorescent Probes and Labeling Technologies, 11th Edition, 2010. Molecular Probes/Life Technologies. 4849 Pitchford Ave., Eugene, Oreg. 97402; GRAVIER J, Navarro F P, Delmas T, Mittler F, Couffin A C, Vinet F, Texier I. Lipidots: competitive organic alternative to quantum dots for in vivo fluorescence imaging. J Biomed Opt. 16(9, 2011):096013; ROMOSER A, Ritter D, Majitha R, Meissner K E, McShane M, Sayes C M. Mitigation of quantum dot cytotoxicity by microencapsulation. PLoS One. 6(7, 2011):e22079:pp. 1-7; Andrew M. SMITH, Michael C. Mancini, and Shuming Nie. Second window for in vivo imaging. Nat Nanotechnol 4(11, 2009): 710-711].

Once the patient is ready to apply the stimulator as shown in FIG. 6, he or she will place the stimulator at a position thought to be approximately correct, then move it across the surface of the neck in an attempt to align positions of the apertures or windows 49 in FIG. 3D with the positions of the stained or tattooed spots on the his or her skin. The stimulator will sense when the alignment is correct, as shown in FIG. 3D, using a light source, dichroic mirror, filter, and photodetector. The light source is preferably a light emitting diode (LED) with integral lens that emits light that causes the fluorescent dye/fluorophore to fluoresce. For example, if ultraviolet light causes the dye to fluoresce blue light, the LED may be selected to emit light in the near ultraviolet at a wavelength between 375 to 395 nm. If infrared light causes the dye (e.g., indocyanine green) to fluoresce at a wavelength greater than 820 nm, the LED may be selected to emit light at a wavelength or 760 or 785 nm. The light emitted from the LED is indicated in FIG. 3D as 51. As shown, time-varying power to the LED causes the light amplitude to oscillate at a frequency that is determined by the LED power source. For example, the frequency could be that illustrated in FIG. 2B. The emitted light 51 then encounters a dichroic mirror that mostly reflects light below a certain wavelength and passes light having longer wavelengths. For example, if the LED emits light in the near ultraviolet, the reflected light should also be in the near ultraviolet. Accordingly, the dichroic mirror could be selected to reflect light with a wavelength less than 410 nm and pass longer wavelengths (e.g., blue light at 450 nm). If the LED emits light at a wavelength of 785 nm or less, the dichroic mirror could be selected to reflect light with a wavelength less than 820 nm and pass longer wavelengths. The reflected light is shown in FIG. 3D as 52. That light will then pass through the aperture 49. Note that a window may have been placed within the aperture 49 to keep the system clean, in which case the window will have been selected to pass all relevant wavelengths of light and be essentially non-reflective. A small percentage of the light emitted by the LED 51 will unavoidably pass through the dichroic mirror, which is indicated as 53 in FIG. 3D. That light is absorbed by a stop, as shown in the figure.

Once the light passes through the aperture 49, it encounters the patient's skin. If the aperture has not been aligned with the fluorophore-containing spot on the patient's skin, the unstained skin itself may emit autofluorescence, which would be more of an issue with the ultraviolet illumination than with the infrared illumination. But when the aperture does align with the spot, the dye in the spot should fluoresce intensely. In either case, some of the light from the LED will also be backscattered through the aperture, i.e., the light emerging from the patient's skin will be a combination of backscatter (no change of wavelength) plus fluorescence (light having a longer wavelength than that from the LED). The light emanating from the patient's skin is indicated as 54 in FIG. 3D. The backscattered light within 54 will be reflected by the dichroic mirror towards the LED (55 in FIG.

3D). The remaining light will pass through the dichroic mirror towards a photodetector (56 in FIG. 3D). The relatively small portion of light 56 that is backscatter is filtered out using a notch filter, selected to remove light having a wavelength at or near that produced by the LED. Thus, the light that impinges on the photodetector is almost entirely the longer wavelength fluorescence, consisting of fluorescence from the dye, along with any autofluorescence emanating from the patient's skin.

The photodetector may be any detector known in the art to be responsive to light at the fluorescence wavelengths, such as a silicon photodiode. The photodetector then converts the fluorescent light signal into either a current or voltage signal, depending upon the mode of operation. Because the current or voltage signal will also have superimposed noise, it is filtered at the same frequency as the modulation frequency of the LED light emission, thereby removing noise that generally has frequency content different than the light modulation frequency. If the signal is particularly noisy, lock-in amplifier (phase-sensitive detector) methods may also be used to extract the amplitude of the fluorescence signal. When the aperture (49 in FIG. 3D) is eventually aligned with the spot on the patient's skin, the fluorescence signal will then increase significantly, relative to the signal produced when the aperture is adjacent only to skin that has not been stained (i.e., autofluorescence). Subtraction of the autofluorescence signal from the total signal provides a final signal, the value of which should increase as the skin-spot and aperture become better aligned. If there are more than one apertures (49 in FIG. 3D), each of them may have their own LED, dichroic mirror, filter, and photodetector, in which case, the sum of the electronically-detected signals corresponding to the different spots' fluorescence indicates whether all the skin-spots and apertures have been aligned. Alternatively, a single LED, dichroic mirror, filter, and photodetector may be used, in which case a Y-shaped optical fiber may be used to join two external apertures (top of the Y) to form a single window (bottom of the Y).

As shown in FIG. 3D, the fluorescence signal is provided to the control unit 330 in FIG. 1 and FIG. 5. The control unit may then use that signal to display within the patient interface computer program the extent to which the stimulator has been optimally positioned. The control unit may also be configured to disable stimulation of the vagus nerve unless alignment of the skin-spots and apertures has been detected. For example, use of the fluorescent spot alignment signal is one method to test whether the patient is attempting to stimulate the vagus nerve on the intended side of the neck. It is understood, however, that the fluorescence alignment method described above may not be suitable for all patients, particularly patients having necks that are wrinkled or that contain large amounts of fatty tissue.

Another method for testing whether the patient is attempting to stimulate the vagus nerve on the intended side of the neck makes use of miniature three-axis accelerometers (possibly with combined gyroscopes) that are embedded in the body of the stimulator (for example, Model LSM330DL from STMicroelectronics, 750 Canyon Dr #300 Coppell, Tex. 75019). Such an accelerometer is situated in each of the two simulator heads (31 in FIG. 3), and another accelerometer is situated in the vicinity of the bottom of the stimulator (38 in FIG. 3). The accelerometers will be providing positional data even when the stimulator is attached to the docking station, so that the orientation of the stimulator with respect to gravity is known from that data, and initial positions of the accelerometers with respect to one another are also known from the structure of the stimulator. Inferences that may be made, as described below, may then be made by a computer program that is implemented by a microprocessor that is situated within the stimulator housing. The patient will be facing the docking station when he or she removes the stimulator from the docking station, thereby defining directions left and right as viewed by the patient. As the patient holds the stimulator in a hand and even walks about the room, relative positions of the stimulator heads retain their left and right aspects because the stimulator housing and patient with the stimulator in hand move together. Thus, by integrating the accelerations provided by the accelerometers to infer the present location of the accelerometers, the directions left and right may also be inferred, after translocation and rotation of the initial accelerometer axes into the present axes. So when the patient begins the stimulation as indicated by rotation of the amplitude thumbwheel (34 in FIG. 3), it may be determined that the stimulator heads with respect to the base of the stimulator are pointing generally in the leftward direction (i.e., right vagus nerve stimulated is being attempted) or generally in the rightward direction (i.e., left vagus nerve stimulation is being attempted).

The left versus right inference described in the previous paragraph may be confirmed by the stimulator's computer program, by examining the positions of the stimulator heads with respect to one another, as indicated by the accelerometer data. The stimulator shown in FIG. 3A has a thumbwheel that could be rotated by either the left or right hand thumbs. If the wheel is being rotated by the right hand thumb (right vagus nerve stimulated is being attempted), a particular stimulator head will be on top. However, if the wheel is being rotated by the left hand thumb (left vagus nerve stimulated is being attempted), the other stimulator head will be on top. Alternatively, the decision by the stimulator's computer program as to which hand is being used to hold the stimulator may be made by measuring capacitance on the outside of the stimulator body, which may distinguish fingers wrapped around the device versus the ball of a thumb [Raphael WIMMER and Sebastian Boring. HandSense: discriminating different ways of grasping and holding a tangible user interface. Proceedings of the 3rd International Conference on Tangible and Embedded Interaction, pp. 359-362. ACM New York, N.Y., 2009]. If the combined decision of the stimulator is that the patient is attempting to stimulate the wrong vagus nerve, the stimulation will be withheld, and the stimulator may then communicate with the patient via the interface computer program (in the mobile phone or laptop computer) to alert the patient of that fact and possibly allow for overriding that decision.

Assume now that the vagus nerve is being stimulated on the correct side of the neck and that the stimulator position is optimal. The patient may then attempt to adjust the amplitude of the stimulation. If the stimulator is being held in place by hand, it is likely that there may be inadvertent fluctuating movement of the stimulator, due for example to neck movement during respiration. Such relative movements will affect the effectiveness of the stimulation. However, they may be monitored by accelerometers in the stimulator, which may be transmitted as movement data from the stimulator to the patient interface computer program (in the mobile phone or laptop computer). The movements may also be accompanied by fluctuations in the spot-alignment fluorescence signal. By watching a graphical display of the relative movements shown by the patient interface computer program, the patient may use that display in an attempt to deliberately minimize the movements. Otherwise, the patient may attempt to adjust the amplitude of the stimulator as compensation for movement of the stimulator away from its optimum position. In a section that follows, it is described how the stimulator itself may modulate the amplitude of the stimulation in order to make such compensations.

The stimulation waveform may be synthesized within the stimulator housing, or it may be synthesized in the docking station or some other component of the system and transmitted to the stimulator housing. Note that the latter is generally different than the transmission of a pre-recorded waveform signal [U.S. Pat. No. 8,112,154, entitled Systems and methods for neuromodulation using pre-recorded waveforms, to REZAI et al]. During the stimulation session, the patient may also test whether the vagus nerve is in fact being stimulated. Several of the test methods described in previous sections are well suited to implementation within the patient interface device, for example, as a mobile phone app. For the laryngeal tests, the patient will perform the rising vowel test, speaking into the microphone of the mobile phone held at a fixed distance from the patient's mouth. The app will then digitize the speech and process it as disclosed above, or transmit the speech data for processing to the docking station, or to computers on the internet. Similarly, the electroglottographic and/or laryngeal electromyographic data will be transmitted from the stimulator housing for processing, with all test results of the processing transmitted back to the interface device for viewing by the patient.

For the pupil diameter test, the camera of the mobile phone will be focused onto one or both eyes of the patient, the image of which will be processed to determine pupil diameter, latency, and asymmetry indices. Alternatively, the mobile phone is attached by cable to a camera, preferably an infrared camera, images from which may be transferred from the camera to the mobile phone. Images of the patient's pupil(s) from taken by either the mobile phone or auxiliary camera will also be processed within the app or transmitted for processing to the docking station, or to computers on the internet. Again, all results of the processing will be transmitted back to the interface device for viewing by the patient. Such results will also be transmitted to the patient's caregiver for review. As described in the next section, the patient's heart rate may be measured with sensors that do not even require that an ECG electrode be attached to the patient's skin. The sensors may instead be situated within the patient's clothing. In any case, the measured individual heart beats provide the raw data needed to calculate the heart rate variability indices that were described in a previous section. The electrodermal test would, however, require that the electrodermal sensor(s) be attached to the patient's skin. Such sensors may also have built-in wireless transmission capability. The raw electrodermal data will then be transmitted wirelessly to the docking station, which will process the data or transmit the data to some other device for processing. The patient will then view the results of these tests and adjust the amplitude of the stimulator accordingly.

Stimulation by the patient will then continue until the batteries of the stimulator are depleted, or the patient decides to terminate the stimulation session. At that point, the patient will insert the stimulator housing back into the docking station, whereupon the stimulator will transfer to the docking station data that its microprocessor has caused to be stored regarding the stimulation session (e.g., stimulation amplitude as a function of time and information about movements of the device during the session, duration of the stimulation, etc.). Such information will then be transmitted to and displayed by the patient interface computer program (in the mobile phone or laptop computer), which will subsequently ask the patient questions regarding the effectiveness of the stimulation. Such questions may be in regards to the post-stimulation severity of the headache, whether the severity decreased gradually or abruptly during the course of the stimulation, and whether anything unusual or noteworthy occurred during the stimulation. All such post-stimulation data will also be delivered over the internet by the patient interface computer program to the physician's computer for review and possible adjustment of the algorithm that is used to select stimulation parameters and regimens. It is understood that the physician will adjust the algorithm based not only on the experience of each individual patient, but on the experience of all patients collectively so as to improve effectiveness of the stimulator's use, for example, by identifying characteristics of most and least responsive patients.

Before logging off of the interface computer program, the patient may also review database records and summaries about all previous treatment sessions, so as to make his or her own judgment about treatment progress. If the stimulation was part of a prophylactic treatment regimen that was prescribed by the patient's physician, the patient interface computer program will remind the patient about the schedule for the upcoming self-treatment sessions and allow for a rescheduling if necessary.

For some patients, the stimulation may be performed for as little as five minutes, but it may also be for up to 30 minutes or longer. The treatment is generally performed once or twice daily or several times a week, for 12 weeks or longer before a decision is made as to whether to continue the treatment. For patients experiencing intermittent symptoms, the treatment may be performed only when the patient is symptomatic. However, it is understood that parameters of the stimulation protocol may be varied in response to heterogeneity in the pathophysiology of patients. Different stimulation parameters may also be used as the course of the patient's condition changes.

In some embodiments of the invention, pairing of vagus nerve stimulation may be with a additional sensory stimulation. The paired sensory stimulation may be bright light, sound, tactile stimulation, or electrical stimulation of the tongue to simulate odor/taste, e.g., pulsating with the same frequency as the vagus nerve electrical stimulation. The sensory stimulation may be intended for the measurement of an evoked potential. But the rationale for paired sensory stimulation may also be the same as simultaneous, paired stimulation of both left and right vagus nerves, namely, that the pair of signals interacting with one another in the brain may result in the formation of larger and more coherent neural ensembles than the neural ensembles associated with the individual signals, thereby enhancing the therapeutic effect. This pairing may be considered especially when some such corresponding sensory circuit of the brain is thought to be partly responsible for triggering the migraine headache.

Brain imaging methods may be used for reasons other than simply demonstrating that the vagus nerve is being stimulated. Selection of stimulation parameters to preferentially stimulate particular regions of the brain may be done empirically, wherein a set of stimulation parameters are chosen, and the responsive region of the brain is measured using fMRI or a related imaging method [CHAE J H, Nahas Z, Lomarev M, Denslow S, Lorberbaum J P, Bohning D E, George M S. A review of functional neuroimaging studies of vagus nerve stimulation (VNS). J Psychiatr Res. 37(6, 2003):443-455; CONWAY C R, Sheline Y I, Chibnall J T, George M S, Fletcher J W, Mintun M A. Cerebral blood flow changes during vagus nerve stimulation for depression.

Psychiatry Res. 146(2, 2006)179-84]. Thus, by performing the imaging with different sets of stimulation parameters, a database may be constructed, such that the inverse problem of selecting parameters to match a particular brain region may be solved by consulting the database.

The individualized selection of parameters for the nerve stimulation protocol may based on trial and error in order to obtain a beneficial response without the sensation of skin pain or muscle twitches. Alternatively, the selection of parameter values may involve tuning as understood in control theory, as described below. It is understood that parameters may also be varied randomly in order to simulate normal physiological variability, thereby possibly inducing a beneficial response in the patient [Buchman T G. Nonlinear dynamics, complex systems, and the pathobiology of critical illness. Curr Opin Crit Care 10(5, 2004):378-82].

Use of Control Theory Methods to Improve Treatment of Individual Patients

The vagus nerve stimulation may employ methods of control theory (e.g., feedback) in an attempt to compensate for motion of the stimulator relative to the vagus nerve and to avoid potentially dangerous situations such as excessive heart rate. Thus, with these methods, the parameters of the vagus nerve stimulation may be changed automatically, depending on environmental signals or on physiological measurements that are made, in attempt to maintain the values of the physiological signals within predetermined ranges.

When stimulating the vagus nerve, motion variability may often be attributable to the patient's breathing, which involves contraction and associated change in geometry of the sternocleidomastoid muscle that is situated close to the vagus nerve (identified as 65 in FIG. 8). Modulation of the stimulator amplitude to compensate for this variability may be accomplished by measuring the patient's respiratory phase, or more directly by measuring movement of the stimulator, then using controllers (e.g., PID controllers) that are known in the art of control theory, as now described.

FIG. 9 is a control theory representation of the disclosed vagus nerve stimulation methods. The "System" (patient) receives input from the "Environment." For example, the environment would include ambient temperature, light, and sound, all of which may be triggers of a migraine attack. If the "System" is defined to be only a particular physiological component of the patient, the "Environment" may also be considered to include physiological systems of the patient that are not included in the "System". Thus, if some physiological component can influence the behavior of another physiological component of the patient, but not vice versa, the former component could be part of the environment and the latter could be part of the system. On the other hand, if it is intended to control the former component to influence the latter component, then both components should be considered part of the "System."

The System also receives input from the "Controller", which in this case may comprise the vagus nerve stimulation device, as well as electronic components that may be used to select or set parameters for the stimulation protocol (amplitude, frequency, pulse width, burst number, etc.) or alert the patient as to the need to use or adjust the stimulator (i.e., an alarm). For example, the controller may comprise the control unit 330 in FIG. 1. Feedback in the schema shown in FIG. 9 is possible because physiological measurements of the System are made using sensors. Thus, the values of variables of the system that could be measured define the system's state ("the System Output"). As a practical matter, only some of those measurements are actually made, and they represent the "Sensed Physiological Input" to the Controller.

The preferred sensors will include ones ordinarily used for ambulatory monitoring. For example, the sensors may comprise those used in conventional Holter and bedside monitoring applications, for monitoring heart rate and variability, ECG, respiration depth and rate, core temperature, hydration, blood pressure, brain function, oxygenation, skin impedance, and skin temperature. The sensors may be embedded in garments or placed in sports wristwatches, as currently used in programs that monitor the physiological status of soldiers [G. A. SHAW, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington Mass. 1 Nov. 2004, pp. 1-141]. The ECG sensors should be adapted to the automatic extraction and analysis of particular features of the ECG, for example, indices of P-wave morphology, as well as heart rate variability indices of parasympathetic and sympathetic tone. Measurement of respiration using noninvasive inductive plethysmography, mercury in silastic strain gauges or impedance pneumography is particularly advised, in order to account for the effects of respiration on the heart. A noninvasive accelerometer may also be included among the ambulatory sensors, in order to identify motion artifacts. An event marker may also be included in order for the patient to mark relevant circumstances and sensations.

For brain monitoring, the sensors may comprise ambulatory EEG sensors [CASSON A, Yates D, Smith S, Duncan J, Rodriguez-Villegas E. Wearable electroencephalography. What is it, why is it needed, and what does it entail? IEEE Eng Med Biol Mag. 29(3, 2010):44-56] or optical topography systems for mapping prefrontal cortex activation [Atsumori H, Kiguchi M, Obata A, Sato H, Katura T, Funane T, Maki A. Development of wearable optical topography system for mapping the prefrontal cortex activation. Rev Sci Instrum. 2009 April; 80(4):043704]. Signal processing methods, comprising not only the application of conventional linear filters to the raw EEG data, but also the nearly real-time extraction of non-linear signal features from the data, may be considered to be a part of the EEG monitoring [D. Puthankattil SUBHA, Paul K. Joseph, Rajendra Acharya U, and Choo Min Lim. EEG signal analysis: A survey. J Med Syst 34 (2010)195-212]. Such features would include EEG bands (e.g., delta, theta, alpha, beta).

Detection of the phase of respiration may be performed non-invasively by adhering a thermistor or thermocouple probe to the patient's cheek so as to position the probe at the nasal orifice. Strain gauge signals from belts strapped around the chest, as well as inductive plethysmography and impedance pneumography, are also used traditionally to non-invasively generate a signal that rises and falls as a function of the phase of respiration. Respiratory phase may also be inferred from movement of the sternocleidomastoid muscle that also causes movement of the vagus nerve stimulator during breathing, measured using accelerometers attached to the vagus nerve stimulator, as described below. After digitizing such signals, the phase of respiration may be determined using software such as "puka", which is part of PhysioToolkit, a large published library of open source software and user manuals that are used to process and display a wide range of physiological signals [GOLDBERGER A L, Amaral L A N, Glass L, Hausdorff J M, Ivanov P Ch, Mark R G, Mietus J E, Moody G B, Peng C K, Stanley H E. PhysioBank, PhysioToolkit, and PhysioNet:

Components of a New Research Resource for Complex Physiologic Signals. Circulation 101(23, 2000):e215-e220] available from PhysioNet, M.I.T. Room E25-505A, 77 Massachusetts Avenue, Cambridge, Mass. 02139]. In one embodiment of the present invention, the control unit 330 contains an analog-to-digital converter to receive such analog respiratory signals, and software for the analysis of the digitized respiratory waveform resides within the control unit 330. That software extracts turning points within the respiratory waveform, such as end-expiration and end-inspiration, and forecasts future turning-points, based upon the frequency with which waveforms from previous breaths match a partial waveform for the current breath. The control unit 330 then controls the impulse generator 310, for example, to stimulate the selected nerve only during a selected phase of respiration, such as all of inspiration or only the first second of inspiration, or only the expected middle half of inspiration. In other embodiments of the invention, the physiological or environmental signals are transmitted wirelessly to the controller, as shown in FIG. 5. Some such signals may be received by the docking station (e.g., ambient sound signals) and other may be received within the stimulator housing (e.g., motion signals).

It may be therapeutically advantageous to program the control unit 330 to control the impulse generator 310 in such a way as to temporally modulate stimulation by the electrodes, depending on the phase of the patient's respiration. In patent application JP2008/081479A, entitled Vagus nerve stimulation system, to YOSHIHOTO, a system is also described for keeping the heart rate within safe limits. When the heart rate is too high, that system stimulates a patient's vagus nerve, and when the heart rate is too low, that system tries to achieve stabilization of the heart rate by stimulating the heart itself, rather than use different parameters to stimulate the vagus nerve. In that disclosure, vagal stimulation uses an electrode, which is described as either a surface electrode applied to the body surface or an electrode introduced to the vicinity of the vagus nerve via a hypodermic needle. That disclosure is unrelated to the headache problems that are addressed here, but it does consider stimulation during particular phases of the respiratory cycle, for the following reason. Because the vagus nerve is near the phrenic nerve, Yoshihoto indicates that the phrenic nerve will sometimes be electrically stimulated along with the vagus nerve. The present applicants have not experienced this problem, so the problem may be one of a misplaced electrode. In any case, the phrenic nerve controls muscular movement of the diaphragm, so consequently, stimulation of the phrenic nerve causes the patient to hiccup or experience irregular movement of the diaphragm, or otherwise experience discomfort. To minimize the effects of irregular diaphragm movement, Yoshihoto's system is designed to stimulate the phrenic nerve (and possibly co-stimulate the vagus nerve) only during the inspiration phase of the respiratory cycle and not during expiration. Furthermore, the system is designed to gradually increase and then decrease the magnitude of the electrical stimulation during inspiration (notably amplitude and stimulus rate) so as to make stimulation of the phrenic nerve and diaphragm gradual.

Furthermore, as an option in the present invention, parameters of the stimulation may be modulated by the control unit 330 to control the impulse generator 310 in such a way as to temporally modulate stimulation by the electrodes, so as to achieve and maintain the heart rate within safe or desired limits. In that case, the parameters of the stimulation are individually raised or lowered in increments (power, frequency, etc.), and the effect as an increased, unchanged, or decreased heart rate is stored in the memory of the control unit 330. When the heart rate changes to a value outside the specified range, the control unit 330 automatically resets the parameters to values that had been recorded to produce a heart rate within that range, or if no heart rate within that range has yet been achieved, it increases or decreases parameter values in the direction that previously acquired data indicate would change the heart rate in the direction towards a heart rate in the desired range. Similarly, the arterial blood pressure is also recorded non-invasively in an embodiment of the invention, and as described above, the control unit 330 extracts the systolic, diastolic, and mean arterial blood pressure from the blood pressure waveform. The control unit 330 will then control the impulse generator 310 in such a way as to temporally modulate nerve stimulation by the electrodes, in such a way as to achieve and maintain the blood pressure within predetermined safe or desired limits, by the same method that was indicated above for the heart rate.

Let the measured output variables of the system in FIG. 9 be denoted by Yi (i=1 to Q); let the desired (reference or setpoint) values of yi be denoted by ri and let the controller's input to the system consist of variables $u_j$ (j=1 to P). The objective is for a controller to select the input u; in such a way that the output variables (or a subset of them) closely follows the reference signals $r_i$, i.e., the control error $e_i=r_i-y_i$ is small, even if there is environmental input or noise to the system. Consider the error function $e_i=r_i-y_i$ to be the sensed physiological input to the controller in FIG. 9 (i.e., the reference signals are integral to the controller, which subtracts the measured system values from them to construct the control error signal). The controller will also receive a set of measured environmental signals $v_k$ (k=1 to R), which also act upon the system as shown in FIG. 9.

The functional form of the system's input u(t) is constrained to be as shown in FIGS. 2B and 2C. Ordinarily, a parameter that needs adjusting is the one associated with the amplitude of the signal shown in FIG. 2A. As a first example of the use of feedback to control the system, consider the problem of adjusting the input u(t) from the vagus nerve stimulator (i.e., output from the controller) in order to compensate for motion artifacts.

Nerve activation is generally a function of the second spatial derivative of the extracellular potential along the nerve's axon, which would be changing as the position of the stimulator varies relative to the axon [F. RATTAY. The basic mechanism for the electrical stimulation of the nervous system. Neuroscience 89 (2, 1999):335-346]. Such motion artifact can be due to movement by the patient (e.g., neck movement) or movement within the patient (e.g. sternocleidomastoid muscle contraction associated with respiration), or it can be due to movement of the stimulator relative to the body (slippage or drift). Thus, one expects that because of such undesired or unavoidable motion, there will usually be some error (e=r−y) in the intended (r) versus actual (y) nerve stimulation amplitude that needs continuous adjustment.

Accelerometers can be used to detect all these types of movement, using for example, Model LSM330DL from STMicroelectronics, 750 Canyon Dr #300 Coppell, Tex. 75019. In one embodiment, one or more accelerometer is attached to the patient's neck, and one or more accelerometer is attached to the head(s) of the stimulator in the vicinity of where the stimulator contacts the patient. Because the temporally integrated outputs of the accelerometers provide a measurement of the current position of each accelerometer, the combined accelerometer outputs make it possible to measure any movement of the stimulator relative to the underlying tissue.

The location of the vagus nerve underlying the stimulator may be determined preliminarily by placing an ultrasound probe at the location where the center of the stimulator will be placed, as described in a previous section. As part of the preliminary protocol, the patient with accelerometers attached is then instructed or helped to perform neck movements, breathe deeply so as to contract the sternocleidomastoid muscle, and generally simulate possible motion that may accompany prolonged stimulation with the stimulator. This would include possible slippage or movement of the stimulator relative to an initial position on the patient's neck. While these movements are being performed, the accelerometers are acquiring position information, and the corresponding location of the vagus nerve is determined from the ultrasound image. With these preliminary data, it is then possible to infer the location of the vagus nerve relative to the stimulator, given only the accelerometer data during a stimulation session, by interpolating between the previously acquired vagus nerve position data as a function of accelerometer position data.

For any given position of the stimulator relative to the vagus nerve, it is also possible to infer the amplitude of the electric field that it produces in the vicinity of the vagus nerve. This is done by calculation or by measuring the electric field that is produced by the stimulator as a function of depth and position within a phantom that simulates the relevant bodily tissue [Francis Marion MOORE. Electrical Stimulation for pain suppression: mathematical and physical models. Thesis, School of Engineering, Cornell University, 2007; Bartosz SAWICKI, Robert Szmuro, Przemyslaw Ponecki, Jacek Starzy ski, Stanisaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. Thus, in order to compensate for movement, the controller may increase or decrease the amplitude of the output from the stimulator (u) in proportion to the inferred deviation of the amplitude of the electric field in the vicinity of the vagus nerve, relative to its desired value.

For present purposes, no distinction is made between a system output variable and a variable representing the state of the system. Then, a state-space representation, or model, of the system consists of a set of first order differential equations of the form $dy_i/dt=F_i(t,\{y_i\},\{u_j\},\{v_k\};\{r_l\})$, where t is time and where in general, the rate of change of each variable $y_i$ is a function ($F_i$) of many other output variables as well as the input and environmental signals.

Classical control theory is concerned with situations in which the functional form of $F_i$ is as a linear combination of the state and input variables, but in which coefficients of the linear terms are not necessarily known in advance. In this linear case, the differential equations may be solved with linear transform (e.g., Laplace transform) methods, which convert the differential equations into algebraic equations for straightforward solution. Commercial versions of PID controllers are available, and they are used in 90% of all control applications.

Optimal selection of the parameters of the controller could be through calculation, if the coefficients of the corresponding state differential equation were known in advance. However, they are ordinarily not known, so selection of the controller parameters (tuning) is accomplished by experiments in which the error e either is or is not used to form the system input (respectively, closed loop or open loop experiments). In an open loop experiment, the input is increased in a step (or random binary sequence of steps), and the system response is measured. In a closed loop experiment, the integral and derivative gains are set to zero, the proportional gain is increased until the system starts to oscillate, and the period of oscillation is measured. Depending on whether the experiment is open or closed loop, the selection of PID parameter values may then be selected according to rules that were described initially by Ziegler and Nichols. There are also many improved versions of tuning rules, including some that can be implemented automatically by the controller [LI, Y., Ang, K. H. and Chong, G. C. Y. Patents, software and hardware for PID control: an overview and analysis of the current art. IEEE Control Systems Magazine, 26 (1, 2006): 42-54; Karl Johan .ANG-.strom & Richard M. Murray. Feedback Systems: An Introduction for Scientists and Engineers. Princeton N.J.:Princeton University Press, 2008; Finn HAUGEN. Tuning of PID controllers (Chapter 10) In: Basic Dynamics and Control. 2009. ISBN 978-82-91748-13-9. TechTeach, Enggravhogda 45, N-3711 Skien, Norway. http://techteach.no., pp. 129-155; Dingyu XUE, YangQuan Chen, Derek P. Atherton. PID controller design (Chapter 6), In: Linear Feedback Control: Analysis and Design with MATLAB. Society for Industrial and Applied Mathematics (SIAM).3600 Market Street, 6th Floor, Philadelphia, Pa. (2007), pp. 183-235; Jan JANTZEN, Tuning Of Fuzzy PID Controllers, Technical University of Denmark, report 98-H 871, Sep. 30, 1998].

The controller shown in FIG. 9 may also make use of feed-forward methods [Coleman BROSILOW, Babu Joseph. Feedforward Control (Chapter 9) In: Techniques of Model-Based Control. Upper Saddle River, N.J.: Prentice Hall PTR, 2002. pp., 221-240]. Thus, the controller in FIG. 9 may be a type of predictive controller, methods for which have been developed in other contexts as well, such as when a model of the system is used to calculate future outputs of the system, with the objective of choosing among possible inputs so as to optimize a criterion that is based on future values of the system's output variables.

A disclosure of the use of such feedback and feedforward methods to forecast and avert the onset of an imminent migraine attack was made in the co-pending, commonly assigned application U.S. Ser. No. 13/357,010 (publication US 2012/0185020), entitled Nerve stimulation methods for averting imminent onset or episode of a disease, to SIMON et al, which is hereby incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for treating a medical condition of a patient, the method comprising:
   contacting an outer skin surface of a patient with a contact surface of a nerve stimulator;
   generating an electrical impulse;
   transmitting, as the contact surface contacts the outer skin surface, the electrical impulse from the nerve stimulator, non-invasively through the outer skin surface, to a nerve such that the electrical impulse modulates the nerve;

measuring a physiological response of the patient to the nerve being modulated based on the electrical impulse being transmitted to the nerve;

detecting, based on the physiological response, whether a stimulation level of the electrical impulse sufficiently modulates the nerve to treat the medical condition; and adjusting a position of the contact surface on the outer skin surface based on the physiological response being measured.

2. The method of claim 1, wherein the nerve stimulator comprises a housing hosting the contact surface, wherein the electrical impulse is generated within the housing.

3. The method of claim 1, wherein measuring the physiological response comprises measuring a blood flow associated with the nerve.

4. The method of claim 1, wherein the nerve is at least one of a vagus nerve, a cranial nerve, a peripheral nerve, or a spinal nerve.

5. The method of claim 1, wherein measuring the physiological response comprises sensing a level of a biological marker within the patient.

6. The method of claim 1, wherein measuring the physiological response comprises measuring a property of at least one of a voice of the patient, a laryngeal electromyographic signal, or an electroglottographic signal.

7. The method of claim 1, wherein measuring the physiological response comprises measuring a property of an autonomic nervous system of the patient.

8. The method of claim 1, wherein measuring the physiological response comprises measuring at least one of a vagal artery blood flow of the patient or a cerebral blood flow of the patient.

9. The method of claim 1, wherein measuring the physiological response comprises measuring a chemical within a blood of the patient.

10. The method of claim 1, further comprising adjusting a parameter of the electrical impulse based on the physiological response being measured, wherein the parameter comprises at least one of an amplitude of the electrical impulse, a frequency of the electrical impulse, a duration of the electrical impulse, or a waveform of the electrical impulse.

11. The method of claim 1, wherein the electrical impulse comprises bursts of about 2 pulses per burst to about 20 pulses per burst with each of the bursts having a frequency of about 1 burst per second to about 100 bursts per second and each of the pulses having a duration of about 50 microseconds to about 1000 microseconds.

12. A system for treating a medical condition of a patient, the system comprising:

a stimulator including a contact surface that contacts an outer skin surface of a patient;

an energy source that generates an electric field such that an electric current is transmitted non-invasively from the contact surface through the outer skin surface to the nerve;

a sensor for measuring a physiological response of the patient to the nerve being modulated based on the electrical impulse being transmitted to the nerve;

a device that detects a stimulation level of the nerve based on the physiological response; and a controller coupled to the device, wherein the controller adjusts a position of the contact surface on the outer skin surface based on the stimulation level.

13. The system of claim 12, wherein the stimulator comprises a housing hosting the contact surface, wherein the energy source is positioned within the housing.

14. The system of claim 12, wherein the sensor measures a blood flow associated with the nerve.

15. The system of claim 12, wherein the nerve is at least one of a vagus nerve of the patient, a cranial nerve of the patient, a peripheral nerve of the patient, or a spinal nerve of the patient.

16. The system of claim 12, wherein the sensor detects a level of a biological marker within the patient.

17. The system of claim 12, wherein the sensor detects a property of an autonomic nervous system of the patient.

18. The system of claim 12, wherein the controller adjusts at least one of an amplitude of the electric current, a frequency of the electric current, a duration of the electric current, or a waveform of the electric current.

19. The system of claim 12, wherein the electric current comprises bursts of about 2 pulses per burst to about 20 pulses per burst with each of the bursts having a frequency of about 1 burst per second to about 100 bursts per second and each of the pulses having a duration of about 50 microseconds to about 1000 microseconds.

* * * * *